US008350085B2

(12) United States Patent
Childs

(10) Patent No.: US 8,350,085 B2
(45) Date of Patent: Jan. 8, 2013

(54) COCRYSTALLIZATION

(75) Inventor: Scott L. Childs, Atlanta, GA (US)

(73) Assignee: New Form Pharmaceuticals Inc., New York, NY (US)

( * ) Notice: Subject to any disclaimer, the term of this patent is extended or adjusted under 35 U.S.C. 154(b) by 0 days.

(21) Appl. No.: 13/170,701

(22) Filed: Jun. 28, 2011

(65) Prior Publication Data

US 2011/0257430 A1   Oct. 20, 2011

Related U.S. Application Data

(60) Continuation of application No. 12/234,093, filed on Sep. 19, 2008, and a division of application No. 10/763,987, filed on Jan. 21, 2004, now Pat. No. 7,452,555.

(60) Provisional application No. 60/441,557, filed on Jan. 21, 2003, provisional application No. 60/441,561, filed on Jan. 21, 2003.

(51) Int. Cl.
*C07C 63/70* (2006.01)
(52) U.S. Cl. .................. 564/347; 562/405; 424/666
(58) Field of Classification Search .................. None
See application file for complete search history.

(56) References Cited

U.S. PATENT DOCUMENTS

| | | | |
|---|---|---|---|
| 2,665,277 A | 1/1954 | Homeyer et al. | |
| 4,379,177 A | 4/1983 | McCoy et al. | |
| 4,943,632 A | 7/1990 | Robinson | |
| 5,080,832 A | 1/1992 | Etter et al. | |
| 5,847,214 A | 12/1998 | Arosio et al. | |
| 6,316,672 B1 * | 11/2001 | Stowell et al. ............... | 564/347 |
| 6,931,950 B2 | 8/2005 | Malachowski et al. | |
| 2002/0048610 A1 | 4/2002 | Cima et al. | |
| 2003/0224006 A1 | 12/2003 | Zaworotko et al. | |
| 2005/0186285 A1 | 8/2005 | Ray et al. | |
| 2007/0287194 A1 | 12/2007 | Childs et al. | |
| 2011/0251426 A1 | 10/2011 | Childs et al. | |

FOREIGN PATENT DOCUMENTS

| | | |
|---|---|---|
| JP | 01-308284 | 12/1989 |
| JP | 2005-535602 | 11/2005 |
| WO | WO 01/92293 A2 | 12/2001 |
| WO | WO 03/101392 | 12/2003 |
| WO | WO 2004/078161 | 9/2004 |

OTHER PUBLICATIONS

Gavezzotti Acc. Chem. Res. 1994, 27, 309-314.*
U.S. Appl. No. 60/360,768, "Multiple Component Crystalline Phases Containing a Pharmaceutical Component," filed Mar. 1, 2002.
Office Action of Canadian Intellectual Proper:7), Office for Application No. 2,514,092 dated Jan. 4, 2011.
A. J. C. Wilson (ed). International Tables for X-ray Crystallography, vol. C. Kynoch, Academic Publishers, Dordrecht, 1992, Tables 6.1. 1.4 (pp. 500-502) and 4.2.6.8 (pp. 219-222).
Etter, Margaret C., and Daniel A. Adsmond (1990) "The use of cocrystallization as a method of studying hydrogen bond preferences of 2-aminopyridine," J. Chem. Soc., Chem. Commun. 1990 589-591.
Etter, Margaret C., John C. MacDonald, and Joel Bernstein (1990a) "Graph-set analysis of hydrogen-bond patterns in organic crystals," Acta Crystallogr., Sect. B, Struct. Sci., vol. B46; 256-262.
Etter, Margaret C., Zofia Urbanczyk-Lipkowska, Mohammad Zia-Ebrahimi, and Thomas W. Panunto (1990b) "Hydrogen bond directed cocrystallization and molecular recognition properties of diarylureas," J. Am. Chem. Soc. vol. 112, 8415-8426.
Scott L. Childs, "Non bonded Interactions in Molecular Crystal Structures," Emory Univ., USA, available from UMI, Order No. DA3009424 (288 pp.), Dissertation Abstract-Int. Ref. B2001, 62(3), 1394.
International Search Report and Written Opinion, dated Jul. 18, 2005, from International Application No. PCT/US04/01699.
Aakeroy, C. B, Acta Crystallogr. Sect. B-Struct. Sci. 1997, 53, 569-586.
Aakeroy, C. B.; Evans, T. A; Seddon, K. R, Palinko, 1. New J. Chem. 1999, 23, 145-152.
Aullon, G.; Bellamy, D.; Brammer, L.; Barton, E. A; Orpen, A G. Chem. Commun. 1998, 653-654.
Bartoszak-Adamska, E; Wojciechowski, G.; Jaskoiski, M.; Brzezinski, M,; *Journal of Molecular Structure* 595 (2001) 21-28.
Bettinetti, G.; Caira, M. R; Callegari, A; Merli, M.; Sorrenti, M.; Tadini, C. J. Pharm Sci. 2000, 89, 478-489.
Bettis, J. W.; Lach, J. L.; Hood, J. *American Journal of Hospital Pharmacy* 1973, 30, 240-243.
Bilton, c.; Allen, F H.; Shields, G. P.; Howard, J. A K. *Acta Crystallogr. Sect. B-Struct. Sci.* 2000, 56, 849-856.
Braga, D.; Cojazzi, G.; Abati, A; Maini, L.; Polito M.; Scaccianoce, L.; Grepioni, F J. *Chem. Sco.-Dalton Trans.* 2000, 3969-3975.
Braga, D.; Draper S. M.; Champeil E.; Grepioni, F; *Journal of Organometailic Chemistry* 573 (1999) 73-77.
Braga, D.; Maini, L.; Polito, M.; Grepioni, F *Chem. Common.* 2002, 2302-2303.
Cheung, E. Y. et al, J. Am. Chem. Soc., 2003, 25, 14658-59.
Cheung, E. et al. "Direct Structure Determination of a Multicomponent Molecular Crystal Prepared by a Solid-State Grinding Procedure," J. Am. Chem. Soc. XXXX, XXX (2003).
Coe, S.; Kane J. J.; Nguyen, T. L.; Toledo, L, M.; Wininger, E.; Fowler, F W.; Lauher, *J. W. J. Am. Chem. Soc.* 1997, 119, 86-93.
Daihus, B.; Gorbitz, C. H. *Acta Crystallogr. Sect C-Cryst. Street. Commun.* 1999, 33, 1547-1555.
Datta, S,; Grant D. J. W.; *Nature* Jan. 2004. vol. 3, 42-57.
Dega-Szafran ,Z.; Katrusiak,A; Szafran, M., *J. Mol. Struct.* 2001, 570, 165-174.
Deng, J. et al.; Tetrahedron: *Asymmetry* 11 (2000) 1729-1732.
Desiraju, G. R, The Royal Society of Chemistry, 2003, 466-467.

(Continued)

*Primary Examiner* — Yevegeny Valenrod
(74) *Attorney, Agent, or Firm* — J.A. Lindeman & Co., PLLC

(57) ABSTRACT

The present disclosure relates to novel cocrystals and novel methods for cocrystallization. In particular, the disclosure includes cocrystals comprising a salt of an active agent, such as a chloride salt of an active pharmaceutical ingredient. The present disclosure also relates to methods of preparing cocrystals and methods for screening for solid state phases.

15 Claims, 5 Drawing Sheets

OTHER PUBLICATIONS

Dunitz, J.D.; *The Royal Society of Chemistry* 2003, 506.
Edwards, M.R; Jones, W.; Motherwell, W.D.S., *Cryst. Eng.* 2002 ,5, 25-36.
Fleischman, S.C.; Kuduva, S.S.; McMahon, J. A; Moulton, B.; Walsh, R.D.B. Rodriguez-Homedo, N,; Zaworotko, M., *J. Cryst. Growth Des.* 2003, 3, 909-919.
Goldberg, I., *J. Am. Chem. Soc.* 1982, 104, 7077-7084.
Gorbitz, CH.; Hersieth, H. P., *Acta Crystallogr. Sect. B-Struct. Sci.*, 2000, 56, 526-534.
Gorbitz, CH., *Acta Crystallogr. Sect. Cryst. Struct. Commun.*, 2000, 56, 500-502.
Hu. Z-Q et al., *Acta Cryst.*, (2002) C58, o612-o614.
Hubschle C B. et ai., *Acta Cryst.*, (2002) C:58 o540-o542.
Iimura, N.; Ohashi, Y.; Hirata, H. *Bull. Chem. Soc. Jpn.* 2000, 73, 1097-1103.
Karlsson, R, *Acta Cryst*, (1972) B28, 2358.
Kumar, V.S.S.; Nangia, A; Katz, A.K.: Carrell, H.L. *Cryst Growth Des.* 2002, 2, 313-318.
Kuroda, R; Imai, Y.; Tajlma, N. *Chem. Common.* 2002, 2848-2849.
Morgan, T.K. et al.; 1986 American Chemical Society. 1398-1405.
Nangia, A; Desiraju, G.R., *Acta Crystallogr. Sect. A*, 1998, 54, 934-944.
0'Dowd, c.; Kennedy, J.D.; Thornton-Pett, M.J., *Organomet. Chem.*, 2002, 657, 20-39.
Orita, A; Jiang, L.S.; Nakano, T.; Ma, N.C; Otera, *J. Chem. Commun.* 2002, 1362-1363.
Oswald, L.D.H.; Allan D.R.; McGregor, P.; Motherwell, W.D.S.; Parsons, S.; Pulham C.R., *Acta Crystallogr. Sect. B-Struct. Sci*, 2002, 58, 1057-1066.
Pierpont, C,G.; Lang, S.A., *Acta Crystallogr. Sect. C-Cast. Struct. Commun.* 1986,42, 1085-1087.
Rai, U. S.; George, S., *Thermochim. Acta*1994, 243, 17-25.
Reddy, L.S.; Nangia, A; Lynch, V.M., *Crystal Growth & Design*, "Phenyl-Perftuorophenyl Synthon Mediated Cocrystallization of Carboxylic Acids and Amides," XXXX vol. 0, No. 0, 1-6, 2003.
Remenar, J. F et al., *Organic Process Research & Development* 2003, 7, 990-996.
Remenar, J. F; Morissette, S.L.; Peterson, M. L.; Moulton, B.; :MacPhee J.M.; Guzman, H. R,; Almarsson, 0.,*J. Am. Chem. Soc.*, 2003, 125, 8456-8457.
Rothenberg, G.; Downie, A. P.; Raston C. L..; Scott, J. L. *J. Am. Chem. Soc.* 2001, 123, 8701-8708.
Schauer, C.L. et al., *J. Chem. Soc.*, 1997, 119, 10245-10246.
Shan, N.; Toda, F; Jones, W. *Chem. Commun.* 2002, 2372-2373.
Steiner, T., *Acta Ctystallogr. Sect B-Struct. Sci.*, 1998, 54, 456-463.
Steiner, T., *New J. Chem.* 1998, 22, 1099-1103.
Thallapally, P. K.; Nangia, A *Crystengcomm* 2001, art. No.-27.
TransForm Pharmaceuticals, Inc. Press Release, Lexington, MA, Nov. 3, 2003.
Videnova-Adrabinska, V. *Acta Cryst.*, 1996, B52, 1048-1056.
Vishweshwar, P.; Nangia, A. Lynch, V. M., *Cryst. Gmwth Des.* 2003, 3, 783-790.
Vishweshwar, P., Nangia, A; Lynch, V. M., *Crystengcomm* 2003 164-168.
Walsh R,D.B,; Bradner, M.W.; Fleischman, S.; Morales, L. A; Moulton, B.; Rodriguez-Homedo, N.; Zaworotko, M.J., *J. Chem. Commun.* 2003, 186-187.
Wang, K.W.; Pan, Y.J.; Jin, A.M.Z.,*Krist-New Cryst. Struct.* 2002, 217, 435-436.
International Search Report corresponding to international Application Serial No. PCT/US2005/08746, mailed Jul. 7, 2008, 4 pages.
Written Opinion of the International Searching Authority corresponding to International Application Serial No. PCT/US2005/08746, mailed Jul. 7, 2008, 8 pages.
Ratsimba et al., "Sonocrystallization. The End of Empiricism? A review on the fundamental investigations and the industrial developments," KONA 17:38-48 (1999).
McCausland et al., "Use the power of sonocrystallization for improved properties," Chem. Engin. Progress 97(7):56-61 (2001).
McCausland et al., "Sonocrystallization—ultrasonically promoted crystallization for the optimal isolation of drug actives," Drug Delivery Systems & Sciences-accentus.co.uk, http://www.accentus.co.uk/articles/c3_ddss_article/pdf 2002.
Ueno et al., "In Situ Studies of Ultrasound-Stimulated Fat Crystallization Using Synchrotron Radiation," J. Phys. Chem. B 107:4927-4935 (2003).
Li et al., "Rapid sonocrystallization in the salting-out process," J. Cryst. Growth 247:192-198 (2003).
Sep. 23, 2009, Office Action in U.S. Appl. No. 10/592,591.
Feb. 20, 2009, Office Action in U.S. Appl. No. 10/592,591.
Jun. 25, 2008, Office Action in U.S. Appl. No. 10/592,591.

\* cited by examiner

Figure 2
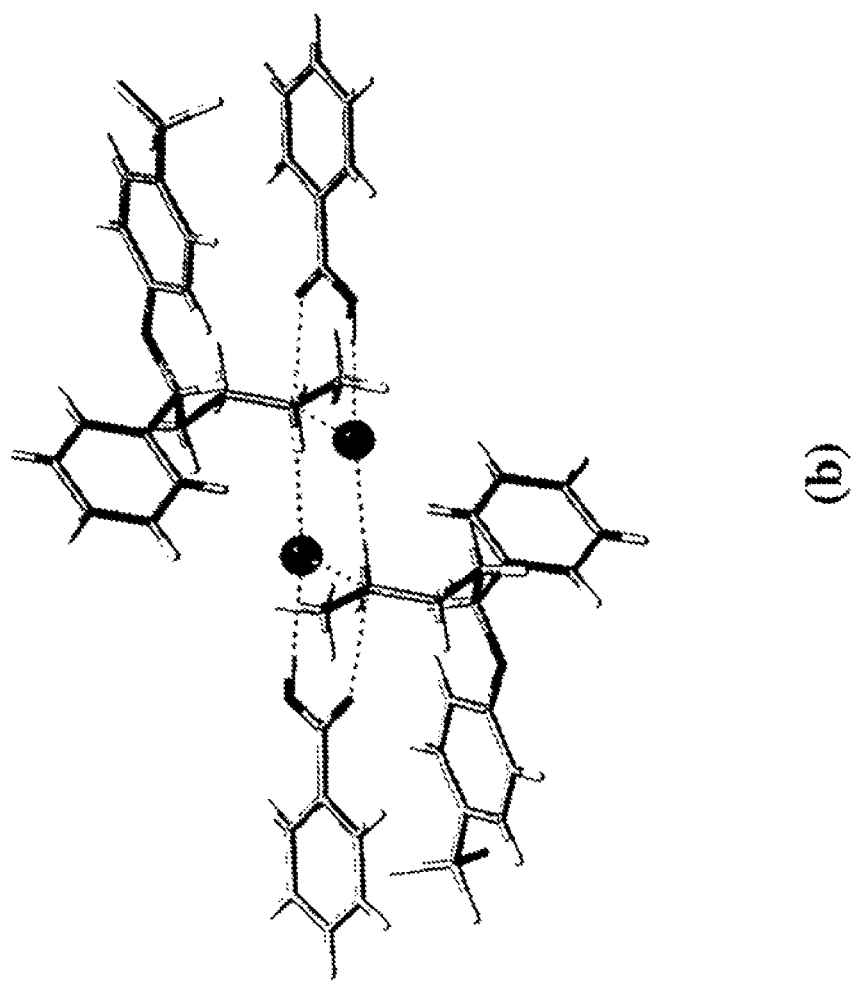
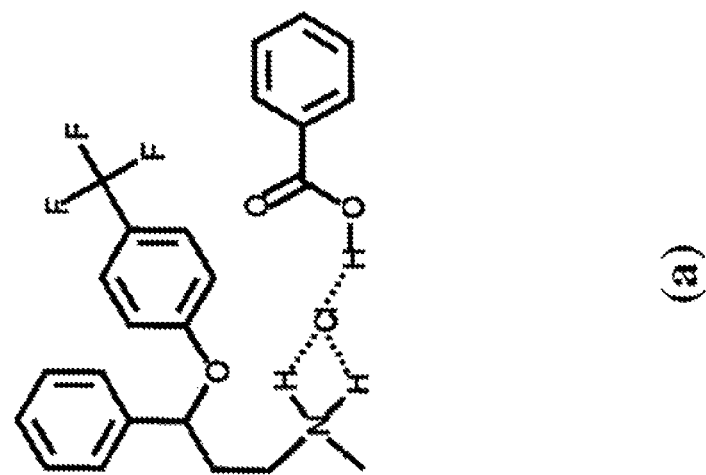

Figure 3
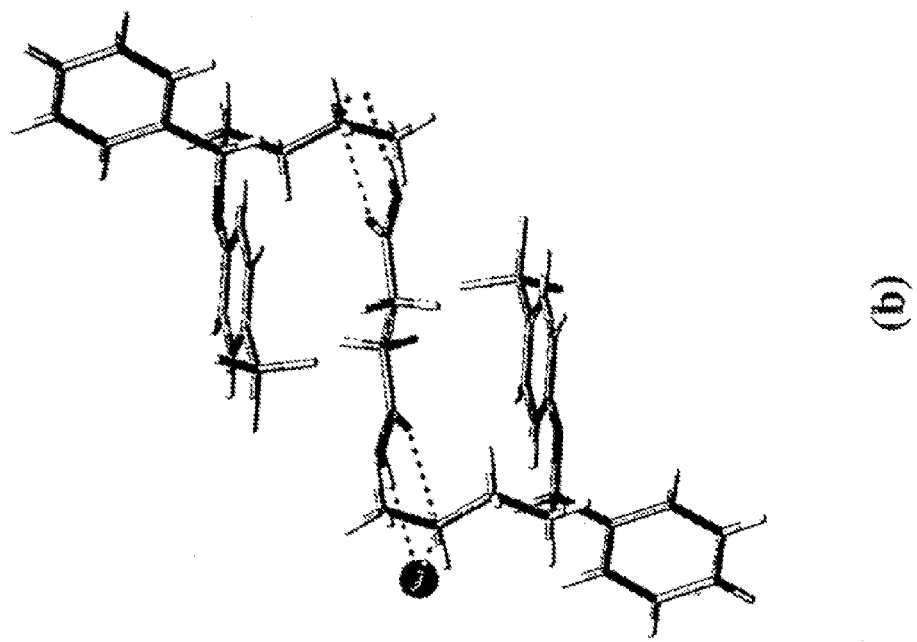
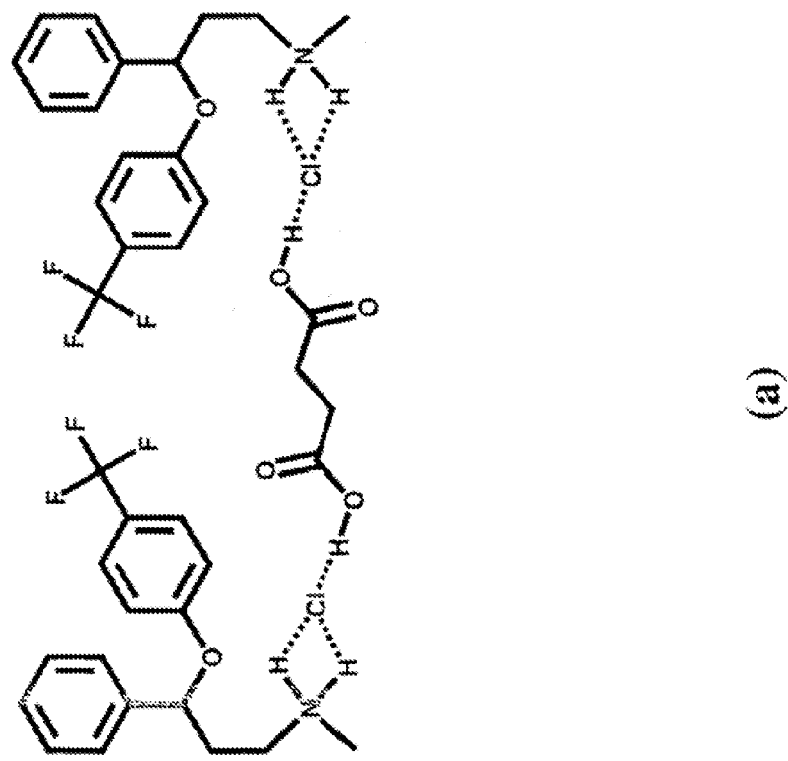
(a)
(b)

Figure 4
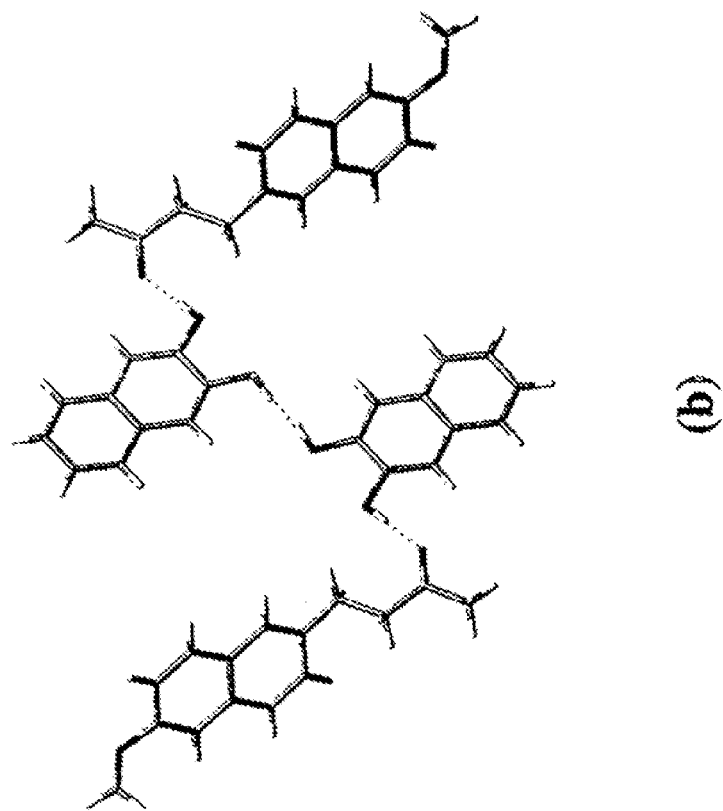
(b)
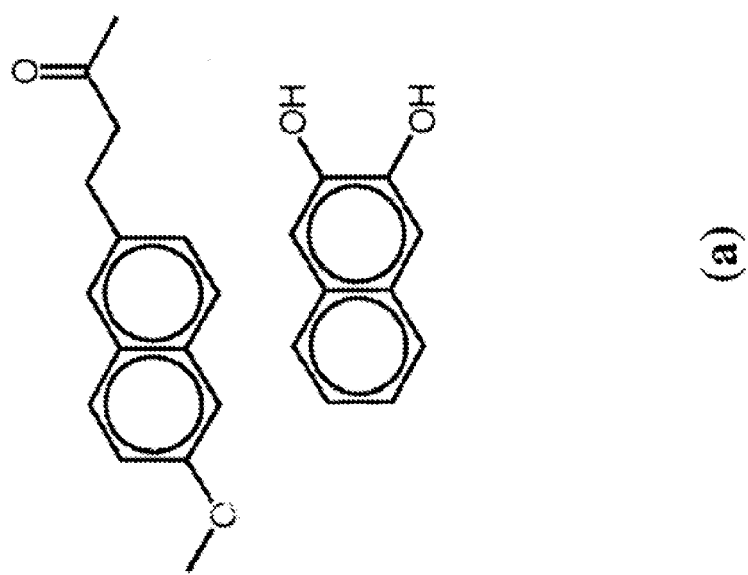
(a)

COCRYSTALLIZATION

CROSS-REFERENCE TO RELATED APPLICATIONS

This application claims the benefit under 35 U.S.C. §119 (e) of U.S. Provisional Application Nos. 60/441,557 and 60/441,561, filed Jan. 21, 2003. These applications are incorporated by reference herein.

FIELD OF THE INVENTION

The present disclosure describes cocrystals comprising active agents, especially active pharmaceutical ingredients (APIs), and methods relating to cocrystals. In particular, novel cocrystals are provided of a salt of an active pharmaceutical ingredient (such as a salt having chloride as the counterion) and a guest that forms a relatively strong interaction with the counterion. Methods are provided for searching for possible solid state phases of a sample and include solidifying the sample as a cocrystal. Methods are also provided for screening a sample for solid state phases and include solidifying the sample as a cocrystal.

BACKGROUND OF THE INVENTION

Cocrystals are crystals that contain two or more non-identical molecules. Examples of cocrystals may be found in the Cambridge Structural Database. Examples of cocrystals may also be found at Etter, Margaret C., and Daniel A. Adsmond (1990) "The use of cocrystallization as a method of studying hydrogen bond preferences of 2-aminopyridine" *J. Chem. Soc., Chem. Commun.* 1990 589-591, Etter, Margaret C., John C. MacDonald, and Joel Bernstein (1990a) "Graph-set analysis of hydrogen-bond patterns in organic crystals" *Acta Crystallogr., Sect. B, Struct. Sci.* B46 256-262, Etter, Margaret C., Zofia Urbańczyk-Lipkowska, Mohammad Zia-Ebrahimi, and Thomas W. Panunto (1990b) "Hydrogen bond directed cocrystallization and molecular recognition properties of diarylureas" *J. Am. Chem. Soc.* 112 8415-8426, which are incorporated herein by reference in their entireties. The following articles are also incorporated herein by reference in their entireties: Carl Henrik Görbotz and Hans-Petter Hersleth, 2000, "On the inclusion of solvent molecules in the crystal structures of organic compounds" Acta Cryst. (2000), B56, 625-534; and V. S. Senthil Kumar, Ashwini Nangia, Amy K. Katz and H. L. Carrell, 2002, "Molecular Complexes of Some Mono- and Dicarboxylic Acids with trans-1,4,-Dithiane-1,4-dioxide" American Chemical Society, Crystal Growth & Design, Vol. 2, No. 4, 2002.

The identification of an optimal composition, formulation, and/or solid state phase is important in the pharmaceutical field, as well as in other fields including nutraceuticals, agricultural chemicals, dyes, explosives, polymer additives, lubricant additives, photographic chemicals, and structural and electronic materials. The new methods described herein may be useful in any of these fields as well as others where solid materials are used.

SUMMARY OF TEE INVENTION

As one aspect, novel cocrystals are provided. The novel cocrystals comprise one or more active agents, particularly of the salts of such active agents.

As another aspect, novel cocrystallization methods are provided which have increased probability of successful cocrystallization. A suitable method of cocrystallization may include identifying a crystal comprising a salt of an active agent, wherein the salt comprises the active agent and a negative counterion. One may identify coordination of the negative counterion (for example, its hydrogen bond interactions within that crystal). One may then select a guest to coordinate more strongly with the negative counterion than the coordination within the crystal. Based upon the evaluation of the nonbonded interactions involving one component of an active agent and/or guest, one selects another molecule or molecules or a salt that will coordinate well, or interact strongly with a hydrogen bond acceptor site that has been identified as being involved in a weak hydrogen bond. If the acceptor site has the ability to interact with stronger hydrogen bond donors, and thus form a more energetically favorable interaction, yet it is presently involved in a weak interaction, then the opportunity exists to replace the weak donor with a Stronger one. For example, if a strong hydrogen bond acceptor is interacting with a weak hydrogen bond donor in a crystal, a cocrystal could be created by adding a strong hydrogen bond donor molecule to the system which would replace the weak donor and bond to the strong acceptor site in the resulting cocrystal. After the selection of a suitable guest, a solution, melt, or physical mixture comprising the active agent, the counterion, and the guest may be prepared. The solution or melt is subjected to a crystallization process, such as evaporation, cooling, or any of the many well-known processes for forming a crystal from a solution or melt. The physical mixture can be ground to form the cocrystal. A cocrystal is formed comprising the salt of the active agent and the guest.

As another aspect, the present disclosure provides a cocrystallization method that produces a novel type of chloride salt cocrystal structure. The method can be useful for generating beneficial solid chloride salts of APIs in cases where the chloride salt was previously disfavored.

As yet another aspect, novel forms of salts of active pharmaceutical ingredients are provided. For example, the present disclosure provides novel cocrystals of fluoxetine HCl and benzoic acid; fluoxetine HCl and succinic acid; and fluoxetine HCl and fumaric acid. Novel forms or solid state phases of active pharmaceutical ingredients may be prepared for which there are no known polymorphs, solvates or hydrates, or where such polymorphs, solvates or hydrates were disfavored.

As a further aspect, a method of modifying one or more physical properties of a drug formulation or drug composition which comprises an API, the method comprising forming a series of cocrystals of the API with a plurality of guests. The method may further comprise measuring a physical property of the cocrystal and/or adjusting the drug formulation or drug composition.

As yet another aspect, an improved method for screening or selecting the optimal solid state phase for active agents, particularly active pharmaceutical ingredients, and salts thereof, is provided. The screening method comprises crystallizing or attempting to crystallize the free base of the active agent, a chloride salt of the active agent, and optionally other salts of the active agent, and cocrystallizing or attempting to cocrystallize the free base of the active agent, a chloride salt of the active agent, and optionally other salts of the active agent. The method may further comprise evaluating one or more properties of the solid forms, such as one or more physical properties.

BRIEF DESCRIPTION OF THE DRAWINGS

FIGS. 2(a) and (b) are drawings of two-dimensional and three-dimensional models of a cocrystal of fluoxetine HCl and benzoic acid (1:1).

FIGS. 3(a) and (b) are drawings of two-dimensional and three-dimensional models of a cocrystal of fluoxetine HCl and succinic acid (2:1).

FIGS. 4(a) and (b) show a two-dimensional drawing of nabumetone and 2,3-naphthalenediol and a three-dimensional model of a cocrystal of nabumetone and 2,3-naphthalenediol (1:1).

DETAILED DESCRIPTION OF THE INVENTION

Figure 1:
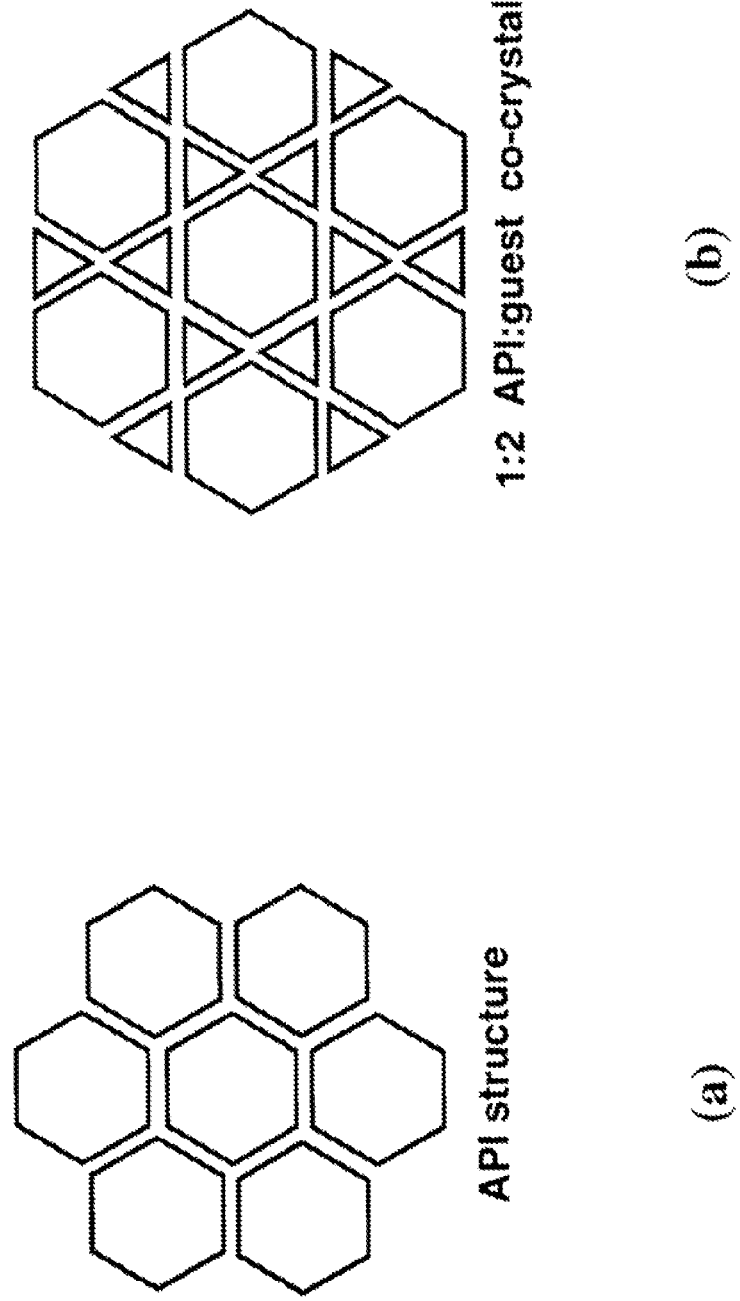
FIGS. 1(a) and (b) illustrate a crystal structure of an active pharmaceutical ingredient and a cocrystal structure containing the same API with a guest molecule.

The present disclosure provides a way of investigating cocrystals and a way of creating new solid state phases in which one or more active agents are cocrystallized with a guest. By cocrystallizing an active agent with a guest such as a pharmaceutically acceptable compound, one can create new solid state phases which may have improved properties over existing solid state phases of that active agent. For example, new drug formulations comprising cocrystals of active pharmaceutical ingredients may have superior properties over existing drug formulations. The active agent and guest will vary depending on the industry. For example, in the pharmaceutical field, the active agent or guest may be an API, and the other component of the cocrystal must be a pharmaceutically acceptable compound. The present techniques are also applicable to active agents from other fields including nutraceuticals, agricultural chemicals, pigments, dyes, explosives, polymer additives, lubricant additives, photographic chemicals, and structural and electronic materials.

Broadly speaking, one aspect relates to the use of undercoordinated counterions to facilitate cocrystallization. While the inventor does not wish to be bound to theory, the inventor believes excellent cocrystals may be formed using hydrochloride salts and similar salts which are strong hydrogen bond acceptors yet contain relatively undercoordinated ions. "Undercoordinated" in this case refers to ions, for example a chloride ion, that are able to form a number of strong hydrogen bonds. An undercoordinated counterion may have hydrogen bonds within a crystal of that salt, but it could form additional hydrogen bonds in a cocrystal and/or form relatively stronger hydrogen bonds in a cocrystal with a guest. An ion is "undercoordinated" when the system is limited in the number of hydrogen bond donors that are available and bonded to the ion. In these cases, the extra hydrogen bond acceptor sites are typically filled by weakly interacting donors such as C—H groups. Chloride ions are strong hydrogen bond acceptors in a crystal structure. In a crystal structure such as fluoxetine hydrochloride, the chloride ion coordinates to the two strong hydrogen bond donors available in the system, and the chloride ion also has three weaker CH—Cl interactions resulting in a pseudo-octahedral coordination environment. There is an opportunity for bonding with these coordination sites, by displacing the weak CH donors that the chloride has recruited to fill its coordination sphere with somewhat stronger hydrogen bond donors from a guest such as benzoic acid, succinic acid, fumaric acid, or another carboxylic acid.

It is useful in forming cocrystals to recognize that relatively weak interactions may be replaced by stronger interactions, even though those stronger interactions may be relatively weak themselves, compared to other interactions. For example, an undercoordinated chloride may have one strong hydrogen bond donor and several weak hydrogen bond donors or two strong hydrogen bond donors and several weak hydrogen bond donors. In a cocrystal, weaker interactions may be replaced by stronger interactions, although those stronger interactions may still be weaker than the strong interactions (charge-assisted hydrogen bonds) present in fluoxetine HCl crystals. The strongest interactions involving chloride ions in crystal structures of organic salts are the charge assisted hydrogen bonds that invariably form between the protonated nitrogen base and the chloride ion. The strongest interactions between neutral molecular groups and the chloride ion involve acids and the chloride ion. Carboxylic acids, for instance, have strong interactions with chloride ions. It can be seen that a combination of carboxylic acids and hydrochloride salts of nitrogen containing bases are especially well suited to cocrystal formation (as demonstrated by the examples included). Furthermore, it can be anticipated that different combinations of these elements could lead to other cocrystals. For example, the active molecule of interest may contain either the neutral carboxylic acid moiety or the protonated nitrogen. The potential exists to cocrystallize an API having a neutral carboxylic acid moiety with a guest that is a hydrochloride salt of a nitrogen-containing organic base.

It is further contemplated that the nature of the protonated nitrogen base will affect the potential for cocrystallization. Numerous strong hydrogen bond donor groups will compete with the carboxylic acid guest for the open acceptor sites on the chloride ion. In order to favor cocrystal formation, the nitrogen base is preferably a tertiary amine because this presents a situation where only one strong charged hydrogen bond donor exists and thus will only occupy one site on the chloride acceptor. Additionally, systems that have only this one tertiary amine and no other strong donors present an especially favorable system for potential cocrystallization. Protonated secondary amines with two N—H donor groups are also favored, although protonated primary amines may also be used. Special consideration must be taken for systems with additional strong hydrogen bond donor and acceptor sites in order to determine the potential for cocrystallization and the optimal guest molecule type for cocrystallization. The potential for cocrystallization involving a carboxylic acid and a hydrochloride salt may be reduced as the number of available strong donors in the system is increased. Additional guidance as to evaluating undercoordination may be found in the inventor's prior work (which is incorporated by reference herein in its entirety), particularly in its discussion of non-bonded motifs: Scott L. Childs, "Nonbonded Interactions In Molecular Crystal Structures", Emory Univ., USA, available From UMI, Order No. DA3009424 (288 pp.), Dissertation Abstract Int. Ref. B2001, 62 (3), 1394. In some circumstances, the undercoordination can be determined by measuring distances, comparing profiles in the Cambridge Structural Database, measuring the pKa of the donors and acceptors, or evaluating the ratio of strong hydrogen bond donors to available acceptors. Other crystal engineering theories may also be used.

The formation of cocrystals is very unpredictable. It is difficult to foresee structural changes as a function of changes in molecular substitution patterns or in molecular geometry. However, the present disclosure provides greater predictability and better probability of success in designing and forming cocrystals.

The present techniques may be employed to generate a wide variety of cocrystals of active agents and guests. For example, the present techniques may be used to generate cocrystals of a salt of an active agent, such as a salt of an active pharmaceutical ingredient, with a neutral guest. Alternatively, a cocrystal of a neutral or zwitterionic active agent (or a salt of an active agent) may be generated with a guest salt, which includes a positive ion and a negative ion of its own. Where the active agent is provided in a salt, it may be positively or negatively charged and have a negative or positive counterion. As an example, for fluoxetine HCl, the active agent fluoxetine is positively charged by virtue of accepting a proton from HCl to form a protonated amine, and chloride is present as a negative counterion. Furthermore, some of the present methods may be employed with a neutral or zwitterionic active agent to form a cocrystal with a neutral guest or ionic guest.

The present techniques provide an opportunity to create a stable solid state phase of a hydrochloride salt of an API that was previously found to have properties that were unsuitable for development. Opportunities for continued development in such a situation have often relied on the fortuitous formation of a stable hydrate or solvate, but the present techniques present the ability to systematically examine alternative formulations of the hydrochloride salt by cocrystallizing the hydrochloride salt of the API with appropriate guest molecules.

Cocrystallization may be an attractive technique for salts of APIs that have been rejected due to problems relating to physical properties. Since cocrystals may have different physical properties than the individual components, APIs with unfavorable physical properties can be cocrystallized with suitable guest molecules and the physical properties of the resulting crystalline solids can be evaluated.

The cocrystals of fluoxetine HCl provide examples of the modification of a physical property (solubility) of an API salt. Cocrystals of fluoxetine HCl:benzoic acid are less soluble and have a lower dissolution rate than crystals of fluoxetine HCl, while cocrystals of fluoxetine HCl:succinic acid are more soluble and have a faster dissolution rate than crystals of fluoxetine HCl.

Other physical properties of APIs or their salts that may be modified by forming a cocrystal include: melting point, density, hygroscopicity, crystal morphology, loading volume, compressibility, and shelf life. Furthermore, other properties such as bioavailability, toxicity, taste, physical stability, chemical stability, production costs, and manufacturing method may be modified by the use of the present cocrystallization techniques.

An active agent can be screened for possible cocrystals where polymorphic forms, hydrates or solvates are especially problematic. A neutral compound that can only be isolated as amorphous material could be cocrystallized. Forming a cocrystal may up-grade the performance of a drug formulation of an active pharmaceutical ingredient by changing physical properties. Some APIs are problematic during wet granulation and compression stages. A bioequivalent cocrystal could rectify this problem.

A cocrystal can be used to isolate or purify a compound during manufacturing. If it is desirable to identify all of the solid state phases of an active pharmaceutical ingredient, then cocrystallization may be particularly desirable.

The present techniques provide new methods of developing and screening active pharmaceutical ingredients. Nontoxic cocrystalline forms of neutral active pharmaceutical ingredients may be prepared, screened, tested, and commercialized. Screening based on cocrystal formation is equivalent in many respects to a salt-screen for neutral APIs. Furthermore, new types of HCl salt structures may be prepared. The properties of hydrochloride salts can be tuned and perfected. New, unique, stable, and marketable phase of hydrochloride salts may be prepared. One can choose whether to make the formulation more soluble or less soluble.

As another aspect, the present techniques may also be used to remove or reduce the water of hydration, and/or to prepare a cocrystal substantially free of water of hydration. A hydrate may be viewed as a cocrystal having water as the guest. Water and guest acids perform a similar role in the stabilization of the crystal structure. In fact, about 28% of the hydrochloride salts of API in the Cambridge Structure Database are hydrates, compared to about 8% of all other organic structures: This indicates an affinity for hydration. The present techniques both capitalize and rectify this affinity, in that an affinity for cocrystallization (as evidence by hydration) is likely indicated, and this affinity for cocrystallization may be employed for the formation of cocrystals with a suitable guest, such as an acid, for example a carboxylic acid. Indeed, in many cocrystals, an acid may have stronger interactions than water molecules and may displace the water of hydration during the formation of the cocrystal. Accordingly, the present techniques provide a method of preparing a cocrystal from a hydrate. A hydrate of a salt is provided, and the hydrate comprises water of hydration. A guest is selected to coordinate with the counterion. Preferably, the guest coordinates more strongly with the counterion than the solvent does. A solution, melt or physical mixture is prepared which comprises the hydrate and the guest. The solution or melt is subjected to a crystallization process, or the physical mixture is subjected to grinding, and a cocrystal comprising the salt of the active agent and the guest is formed, and the salt comprises the active agent and a counterion. Similarly, the present techniques provide a method of preparing a cocrystal from a solvate. A solvate of a salt is provided, and the solvate comprises solvent molecules coordinated with the salt. A guest is selected to coordinate with the counterion. Preferably, the guest coordinates more strongly with the counterion than the solvent does. A solution, melt or physical mixture is prepared comprising the solvate and the guest. The solution or melt is subjected to a crystallization process, or the physical mixture is subjected to grinding, and a cocrystal comprising the salt of the active agent and the guest is formed. The salt comprises the active agent and a counterion.

FIGS. 2(a) and (b) are drawings of two-dimensional and three-dimensional models of a cocrystal of fluoxetine HCl and benzoic acid (1:1). FIG. 2(a) shows a two-dimensional model in which the chloride ion interacts with the hydrogens of the amine group of fluoxetine and of the hydroxyl group of benzoic acid. Through these interactions, which may be characterized as hydrogen bonding, fluoxetine hydrochloride and benzoic acid form a supramolecular structure that may be the basis of a cocrystal. FIG. 2(b) shows a three-dimensional model of the supramolecular organization of fluoxetine hydrochloride and benzoic acid.

FIG. 3(a) and (b) are drawings of two-dimensional and three-dimensional models of a cocrystal of fluoxetine HCl and succinic acid (2:1). FIG. 3(a) shows a two-dimensional model in which the chloride ion interacts with the hydrogens of the ammonium group of fluoxetine and of the hydroxyl group of succinic acid. Through these interactions, which may be characterized as hydrogen bonding, two molecules of fluoxetine hydrochloride and one molecule of succinic acid form a supramolecular structure that may be the basis of a cocrystal. FIG. 3(b) shows a three-dimensional model of the supramolecular organization of the molecules of fluoxetine hydrochloride and succinic acid.

FIGS. 4(a) and (b) show a two-dimensional drawing of nabumetone and 2,3-naphthalenediol and a three-dimensional model of a cocrystal of nabumetone and 2,3-naphthalenediol (1:1).

Active Agent

The active agent is the molecule whose activity is desirable or the object of interest. It is contemplated that one or more active agents may be employed in a cocrystal, according to any of the present techniques. For example, where the active agent is an active pharmaceutical ingredient, the pharmaceutical activity of the active agent is desirable. Other active agents may be nutraceuticals, agricultural chemicals, pigments, dyes, explosives, polymer additives, lubricant additives, photographic chemicals, or structural and electronic materials.

The active agent may be provided as a salt. It is contemplated that one or more salts may be employed in a cocrystal, according to any of the present techniques. The salt may be prepared from the active agent or obtained from a commercial source. Hydrochloride salts of active pharmaceutical ingredients, especially of amine APIs, are especially preferred in the pharmaceutical industry.

In general, it is contemplated that the present techniques will have particularly good results as applied to amine HCl salts as well as other ammonium salts as described in more detail herein. In ammonium acid salts, the active agent has at least one amine moiety which is relatively basic (at least one relatively basic nitrogen), and a salt is formed with an acid that reacts with the amine moiety. Cocrystals may be then formed between the ammonium salts and guests which act as hydrogen-bond donors to the salts. Cocrystals may be formed of chloride salts of APIs, for example buspirone hydrochloride, fluoxetine hydrochloride, and metformin hydrochloride.

The present cocrystals may comprise salts other than chloride salts—the hydrochloride API salts that are listed above are only a sampling of the relevant compounds because the starting material need not be a known hydrochloride. Indeed, many relevant APIs are salts that are not HCl salts because the HCl salt was not believed to be an appropriate material and a different salt was commercialized instead. The present techniques may enable one to employ an HCl salt of an API that is marketed as another type of salt. Alternatively, it may be desirable to employ a salt other than an HCl salt, by replacing the HCl or by forming a salt comprising an active agent that acts as a base with an acid other than HCl. The following acids provide anionic counterions that would be used to replace chlorine. These are relatively strong acids, and include but are not limited to mineral acids, and the carboxylic acid guest is expected to form one or more hydrogen bonds with a hydrogen bond acceptor on the anionic counterion. The list is the conjugate acid that would react with a basic active agent to form a salt:

sulfuric acid
phosphoric acid
hydrobromic acid
nitric acid
pyrophosphoric acid
methanesulfonic acid
thiocyanic acid
naphthalene-2-sulfonic acid
1,5-naphthalenedisulfonic acid
cyclamic acid
p-toluenesulfonic acid
maleic acid
L-aspartic acid
2-hydroxy-ethanesulfonic acid
glycerophosphoric acid
ethanesulfonic acid
hydroiodic acid The present techniques also extend beyond salts as starting materials and also include many weak bases that may have been marketed as neutral forms because the known salts did not have appropriate properties. These salts could be revisited and attempts could be made to cocrystallize the HCl salt. For example, a drug formulation marketed as a tartrate salt of an API could be reformulated by cocrystallizing the HCl salt of the active molecule with an appropriate guest molecule. Thus, cocrystallization could make a useful HCl cocrystal out of the API that is currently marketed as a tartrate, sulfate, or other salt formulation. For this reason the present disclosure includes APIs that are not HCl salts as starting materials.

Furthermore, the present techniques relate to salts other than chloride salts. It is contemplated that hydrobromide salts and sodium salts of APIs may especially benefit from the present techniques, since they form relatively strong non-bonded interactions. For example, the hydrobromide salts citalopram hydrobromide and galantamine hydrobromide are contemplated for cocrystallization with benzoic acid, succinic acid, and other guests compatible with hydrochloride salts.

The present techniques may be employed to form cocrystals of sodium salts of APIs such as, for example, naproxen sodium, tolmetin sodium, and warfarin sodium. When a sodium salt (or other salt of an API having a positive counterion) is employed, different guests are expected to be suitable for cocrystallization than when a hydrochloride salt (or other anionic salt) of an API is employed.

Anions and Cations

As one aspect, the active agent is provided as a salt. A salt of the active agent is formed. Alternatively or additionally, the guest is provided as a salt or a salt of the guest is formed. The salt may comprise the active agent and a counterion that is either a cation or an anion. Among the preferred cations (including cations as well as compounds that can form cations) are aluminum, ammonium, benzathine, calcium, diethanolamine, diethylamine, dimeglumine, disodium, lithium, lysine, magnesium, meglumine, potassium, sodium, and zinc. Among the preferred anions are acetate, L-aspartate, besylate, bicarbonate, carbonate, D-camsylate, L-camsylate, citrate, edisylate, fumarate, gluconate, hydrobromide/bromide, hydrochloride/chloride, D-lactate, L-lactate, DL-lactate, D,L-malate, L-malate, mesylate, pamoate, phosphate, succinate, sulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, acefyllinate, aceturate, aminosalicylate, ascorbate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, and undecylenate.

When a metal cation is employed as a counterion of the active agent, the interaction between guest and cation is not a hydrogen bond but rather is an intermolecular interaction between an electron rich group such as a carbonyl and the metal cation. This interaction is often not as strong as a hydrogen bond, but is still a favorable interaction and thus can contribute to the stabilization of a cocrystal.

The HCl salt of an active pharmaceutical ingredient is especially preferred to create a new type of cocrystal. In this type of solid state phase, one can cocrystallize the HCl salt with a neutral guest molecule. By doing this one can create solid state phases with specific properties. For instance one can make a solid comprising an active pharmaceutical ingredient having greater or lesser intrinsic solubility and/or a faster or slower dissolution rate, depending on the guest compound that is chosen.

Guests

The guest is present in order to form the cocrystal with the active agent. It is contemplated that one or more guests may be employed in a cocrystal, according to any of the present techniques. Accordingly, the guest is not required to have an activity of its own, although it may have some activity that does not overly derogate from the desired activity of the active agent. In some situations, the guest may have the same activity as or an activity complementary to that of the active agent. The guest may be another API. For example, some guests may facilitate the therapeutic effect of an active pharmaceutical ingredient. For pharmaceutical formulations, the guest may be any pharmaceutically acceptable molecule(s) that forms a cocrystal with the API or its salt. The RTECS database is a useful source for toxicology information, and the GRAS list contains about 2500 relevant compounds.

Figure 5:
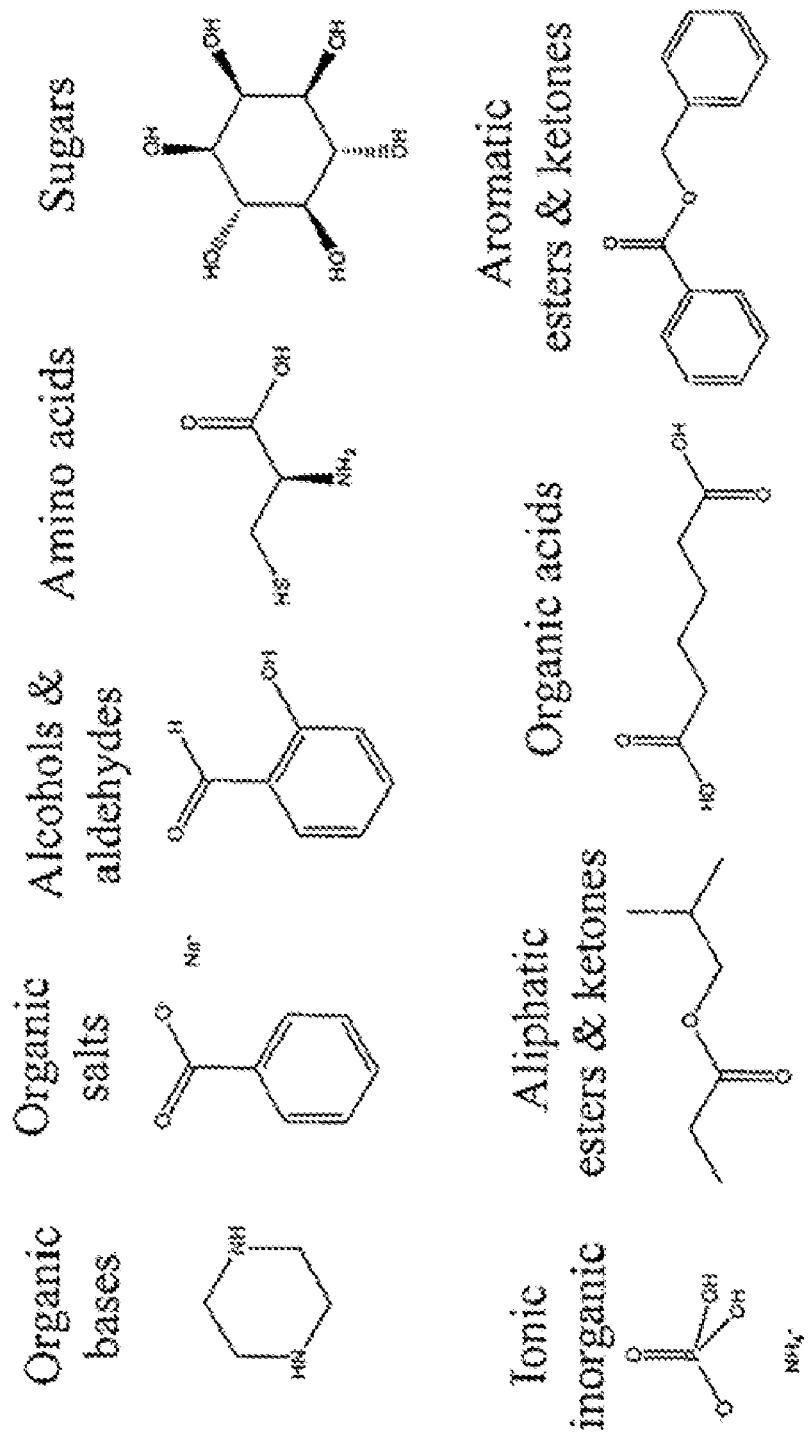
FIG. 5 shows examples of general classes of guests.

The guest may be neutral (such as benzoic acid and succinic acid in the examples below) or ionic (such as sodium benzoate or sodium succinate). Neutral guests are nonionic guests. Ionic guests are compounds or complexes having ionic bonds. FIG. 5 shows several general classes of guests (organic bases, organic salts, alcohols & aldehydes, amino acids, sugars, ionic inorganics, aliphatic esters & ketones, organic acids, and aromatic esters & ketones).

The guest may be an acid that forms hydrogen bonds with the chloride (or other anion). For example, suitable guests which are acids include (but not are not limited to):
ascorbic acid
glucoheptonic acid
sebacic acid
alginic acid
cyclamic acid
ethane-1,2-disulfonic acid
2-hydroxyethanesulfonic acid
2-oxo-glutaric acid
naphthalene-1,5-disulfonic acid
nicotinic acid
pyroglutamic acid
4-acetamidobenzoic acid Table 1 sets forth a group of presently preferred guests. It is contemplated that the guests set forth in the Table may be arranged in subgroups based upon molecular structure and/or physiological effect. Furthermore, the foregoing list is intended to provide a written description of any sublist that omits one or more guests.

Table 2 sets forth another group of preferred guests. It is contemplated that the guests set forth in the Table may be arranged in subgroups based upon molecular structure and/or physiological effect. Furthermore, the foregoing list is intended to provide a written description of any sublist that omits one or more guests.

Table 3 sets forth the group comprising molecules believed at present to be suitable guests. It is contemplated that the guests set forth in the Table may be arranged in subgroups based upon molecular structure and/or physiological effect. Furthermore, the foregoing list is intended to provide a written description of any sublist that omits one or more guests.

Ionic guests are salts themselves, and may be formed from bases and acids prior to being used to form cocrystals. For example, the following bases and acids may be reacted to form ionic guests:

Bases

Ammonia
L-Arginine
Benethamine
Benzathine
Betaine
Calcium Hydroxide
Choline
Deanol
Diethanolamine
Diethylamine
2-(Diethylamino)ethanol
2-Aminoethanol
Ethylenediamine
N-Methylglucamine
Hydrabamine
1H-Imidazole
Lysine
Magnesium Hydroxide
Morpholine
4-(2-Hydroxyethyl)Morpholine
Piperazine
Potassium Hydroxide
Pyrrolidine
1-(2-Hydroxyethyl)Pyrrolidine
Sodium Hydroxide
Triethanolamine
Tromethamine
Zinc Hydroxide Acids (+)-L-Tartaric Acid
1,2,2-Trimethyl-1,3-cyclopentanedicarboxylic Acid
10-Undecylenic Acid
1-Hydroxy-2-naphthoic Acid
(+)-Camphor-10-sulfonic Acid
2,5-Dihydroxybenzoic Acid
2-Furancarboxylic Acid
2-Mercaptobenzoic Acid
3-Cyclopentylpropionic Acid
3-Phenylpropionic Acid
4-Aminosalicylic Acid
4-Hydroxybenzoic Acid
Acetic Acid
Adipic Acid
alpha-Hydroxypropionic Acid
Benzenesulfonic Acid
Benzoic Acid
Carbonic Acid
Cholic Acid
Citric Acid
(−)-D-Tartaric Acid
(+)-D-Camphoric Acid
(+)-D-Malic Acid
(+)-L-Malic Acid
2,2-Dichloroacetic Acid
DL-10-Camphorsulfonic Acid
DL-Glutamic Acid
DL-Malic Acid
DL-Tartaric Acid Dodecylsulfuric Acid
Ethanesulfonic Acid
Ethylenediaminetetraacetic Acid
Ethylsulfuric Acid
Fumaric Acid
Galactaric Acid
Gallic Acid
Gluconic Acid
Glutamic Acid
Glycolic Acid
Hippuric Acid.
Hydriodic Acid
Hydrobromic Acid
Hydrochloric Acid
(−)-L-Apple Acid
(+)-L-Lactic Acid
(+)-L-Tartaric Acid
D,L-Lactic Acid
Lactobionic Acid
L-Aspartic Acid
Lauric Acid
L-Glutamic Acid
Maleic Acid
(−)-L-Malic Acid
Malonic Acid
D,L-Mandelic Acid
Methanesulfonic Acid
Naphthalene-2-sulfonic acid
n-Butyric Acid
n-Decanoic Acid
n-Hexanoic Acid
Nitric acid
n-Tetradecanoic Acid
Octanoic Acid
Oleic Acid
Orotic Acid
Orthoboric Acid
Oxalic Acid
4-Acetamidobenzoic Acid
Palmitic Acid
Pamoic Acid
Phosphoric Acid
Picric Acid
Pivalic Acid
Propionic Acid
p-Toluenesulfonic Acid
Pyrophosphoric Acid
Salicylic Acid
Stearic Acid
Succinic Acid
Sulfosalicylic Acid
Sulfuric Acid
Terephthalic Acid
Thiocyanic Acid
Valeric Acid
Valproic Acid Typically, suitable guests will have complementary ability to noncovalently bond to the active agent or its salt, for example the ability to form hydrogen bonds with the active agent or its salt. Suitable guests for active agents having negative counterions include, but are not limited to, compounds having alcohol, ketone, ester, and/or carboxylic acid functionalities. Suitable guests may include organic acids, organic bases, organic salts, alcohols, aldehydes, amino acids, sugars, ionic inorganic compounds, aliphatic esters and ketones, and aromatic esters and ketones.

Among the presently preferred neutral guests are those which are not liquids at room temperature. Also among the presently preferred neutral guests are carboxylic acids having at least three carbon atoms, alternatively at least four carbon atoms, and which do not form solvates. For example, if the following acids were combined with active agents, the combination would more properly be considered a solvate than a cocrystal: acetic acid, propionic acid, and butyric acid. However, in certain embodiments of the present invention (for example, in certain cocrystals, cocrystallization methods, and screening methods), the use of solvents and solvates may still be desirable, and the use of solvents and solvates is not excluded from the scope of any cocrystal or method except where explicitly stated.

Detection of Cocrystals

Cocrystals may be detected by x-ray diffraction analysis or other suitable techniques. The observation of physical properties of a solid (particularly its melting point) which differ from, the physical properties of the starting materials and the polymorphs and/or solvates and/or hydrates of the starting materials, is an indicator that a cocrystal has been formed.

A method of crystal engineering is described. An active pharmaceutical ingredient such as fluoxetine hydrochloride is recognized as possessing a strong hydrogen bond acceptor. The API is screened against a library of strong hydrogen bond donors or other possible guest compounds. Such a library is selected and ordered based upon nontoxicity, physical property, and the availability and geometric arrangement of hydrogen bond donors that are complementary to the API.

The results from a cocrystal screen of fluoxetine hydrochloride demonstrate a new class of cocrystal that is broadly applicable to a wide variety of hydrochloride salts of APIs. This new approach is a general method that allows creation of cocrystals starting with the hydrochloride salt of the API. Starting with the hydrochloride retains the advantages of the salt, yet one is still able to use the cocrystal method to alter the physical properties of the resulting solid by adding guest molecules.

EXAMPLE 1

Cocrystallization of Fluoxetine HCl and Benzoic Acid

Cocrystals of fluoxetine HCl:benzoic acid were formed using the following procedures. In one preparation, a 505 mg sample of fluoxetine HCl and 178 mg of benzoic acid were dissolved with heating in 5 mL of acetonitrile. The solution was allowed to crystallize in a small crystallization dish. Well-formed crystalline material formed within 7 minutes. This material was isolated on filter paper and dried in the air to yield 546 (80%) of fluoxetine HCl:benzoic acid (1:1) cocrystal.

In another preparation, a 5.00 g sample of fluoxetine HCl and 1.76 g of benzoic acid were dissolved in 50 mL of acetonitrile with heating. The solution was allowed to crystallize in a large evaporating dish. The resulting solid was isolated on filter paper and dried in the air to yield 5.40 g (92%) of fluoxetine HCl:benzoic acid (1:1) cocrystal.

The cocrystal had a relatively slow dissolution rate and lower water solubility. The measured melting point was 134° C.+/−2° C. for the cocrystal. The cocrystal is expected to have a good toxicology profile, since benzoic acid is known to be safe and appears on the GRAS list from the U.S. Food and Drug Administration.

The resulting cocrystal is a ternary system comprising the protonated API base, the chloride ion, and the neutral guest molecule.

The present inventor believes there are no known solvates or hydrates of fluoxetine hydrochloride. Thus, the formation of a cocrystal of fluoxetine hydrochloride constitutes a surprising achievement and provides a unique composition.

EXAMPLE 2

Cocrystallization of Fluoxetine HCl and Succinic Acid

Cocrystals of fluoxetine HCl and succinic acid were prepared as follows. In one preparation, a 458 mg sample of fluoxetine HCl was dissolved in 8 mL of acetonitrile by heating the solution gently. A 78 mg sample of succinic acid was added to the warm solution and dissolved. The solution was allowed to evaporate rapidly in a crystallization dish. Well-formed crystals as blocks formed as the solvent evaporated over 8 minutes. The product was collected on filter paper and dried to yield 401 mg of fluoxetine HCl:succinic acid (2:1) cocrystal (75% yield).

In another preparation, a 5.00 g sample of fluoxetine HCl and 0.85 g of succinic acid were dissolved in acetonitrile with heating. The solution was allowed to crystallize in an open evaporating dish over a 15 minute period. The solid material was isolated on filter paper and dried to yield 5.40 g (92% yield) of fluoxetine HCl:succinic acid (2:1) cocrystal.

The measured melting points were 158° C. for fluoxetine HCl, 184° C. for succinic acid, and 137° C. for the cocrystal. The cocrystal is expected to have a good toxicology profile, since succinic acid is known to be safe and appears on the Generally Recognized As Safe ("GRAS") list from the U.S. Food and Drug Administration.

EXAMPLE 3

Cocrystallization of Nabumetone and 2,3-naphthalenediol

As a demonstrative example, a cocrystal comprising a neutral API is described in this example. Cocrystals of nabumetone (a neutral API) and 2,3-naphthalenediol were prepared as follows. A 4.01 g sample of 2,3-naphthalenediol and 5.7 g of nabumetone were dissolved in 50 mL of nitromethane with heating. A solid was formed as the solution cooled and was allowed to stand overnight. The solid was filtered from the remaining solvent and dried in the air to yield 6.61 g (68%) of nabumetone:2,3-naphthalenediol (1:1) cocrystal.

The resulting cocrystal had a 1:1 molar ratio of nabumetone to 2,3-naphthalienediol. The measured melting points were 80° C. for nabumetone, 162° C. for 2,3-naphthalienediol, and 98° C. for the cocrystal. The cocrystal is expected to have a relatively poor toxicology profile. However, this example demonstrates one basis for the selection of guest molecules: molecular structural similarities. In this case the molecular recognition of the naphthalene moieties of the API and the guest contribute to the stability of the cocrystal. In addition, the stronger alcohol to ketone hydrogen bonds formed by the cocrystal contribute to the stability of the cocrystal. The only hydrogen bond donors available in the API crystal structure are weak C—H groups. The stronger hydrogen bond donors on the guest molecule are able to form stronger intermolecular interaction between the API and guest, compared to the interactions between molecules of the API.

EXAMPLE 4

Crystal Structure Analysis of Fluoxetine HCl:Benzoic Acid Cocrystal (1:1)

A suitable cocrystal of fluoxetine HCl:benzoic acid (1:1) was coated with Paratone N oil, suspended in a small fiber loop and placed in a cooled nitrogen gas stream at 100 K on a Bruker D8 SMART APEX CCD sealed tube diffractometer with graphite monochromated MoK$_\alpha$ (0.71073 Å) radiation. Data were measured using a series of combinations of phi and omega scans with 10 second frame exposures and 0.3° frame widths. Data collection, indexing and initial cell refinements were all carried out using SMART software (SMART Version 5.624, 2000, Bruker AXS, Inc., Analytical X-ray Systems, 5465 East Cheryl Parkway, Madison Wis. 53711-5373). Frame integration and final cell refinements were done using SAINT software (SAINT Version 6.02, 2000, Bruker AXS, Inc., Analytical X-ray Systems, 5465 East Cheryl Parkway, Madison Wis. 53711-5373). The final cell parameters were determined from least-squares refinement on 5435 reflections. The SADABS program was used to carry out absorption corrections (SADABS Version 2.03, 2001, George Sheldrick, University of Göttingen).

The structure was solved using Direct methods and difference Fourier techniques (SHELXTL V5.10, 2000, Bruker AXS, Inc., Analytical X-ray Systems, 5465 East Cheryl Parkway, Madison Wis. 53711-5373). Hydrogen atoms were placed their expected chemical positions using the HFIX command and were included in the final cycles of least squares with isotropic U$_{ij}$'s related to the atom's ridden upon. The C—H distances were fixed at 0.93 Å (aromatic and amide), 0.98 Å (methine), 0.97 Å (methylene), or 0.96 Å (methyl). All non-hydrogen atoms were refined anisotropically. Scattering factors and anomalous dispersion corrections are taken from A. J. C. Wilson (ed), *International Tables for X-ray Crystallography, Volume C*. Kynoch, Academic Publishers, Dordrecht, 1992, Tables 6.1.1.4 (pp. 500-502) and 4.2.6.8 (pp. 219-222), the *International Tables for X-ray Crystallography*. Structure solution, refinement, graphics and generation of publication materials were performed by using SHELXTL, V5.10 software. Additional details of data collection and structure refinement are given in Table 4 which follows.

EXAMPLE 5

Crystal Structure Analysis of Fluoxetine HCl:Succinic Acid Cocrystal (2:1)

A suitable cocrystal of fluoxetine HCl-succinic acid (2:1) was coated with Paratone N oil, suspended in a small fiber loop and placed in a cooled nitrogen gas stream at 100 K on a Bruker D8 SMART APEX CCD sealed tube diffractometer with graphite monochromated MoK$_\alpha$ (0.71073 Å) radiation. Data were measured using a series of combinations of phi and omega scans with 10 second frame exposures and 0.3° frame widths. Data collection, indexing and initial cell refinements were all carried out using SMART software (SMART Version 5.624, 2000, Bruker AXS, Inc., Analytical X-ray Systems, 5465 East Cheryl Parkway, Madison Wis. 53711-5373). Frame integration and final cell refinements were done using SAINT software (SAINT Version 6.02, 2000, Bruker AXS, Inc., Analytical X-ray Systems, 5465 East Cheryl Parkway, Madison Wis. 53711-5373). The final cell parameters were determined from least-squares refinement on 5435 reflections. The SADABS program was used to carry out absorption corrections (SADABS Version 2.03, 2001, George Sheldrick, University of Göttingen).

The structure was solved using Direct methods and difference Fourier techniques (SHELXTL V5.10, 2000, Bruker AXS, Inc., Analytical X-ray Systems, 5465 East Cheryl Parkway, Madison Wis. 53711-5373). Hydrogen atoms were placed their expected chemical positions using the HFIX command and were included in the final cycles of least squares with isotropic $U_{ij}$'s related to the atom's ridden upon. The C—H distances were fixed at 0.93 Å (aromatic and amide), 0.98 Å (methine), 0.97 Å (methylene), or 0.96 Å (methyl). All non-hydrogen atoms were refined anisotropically. Scattering factors and anomalous dispersion corrections are taken from A. J. C. Wilson (ed), *International Tables for X-ray Crystallography, Volume C*. Kynoch, Academic Publishers, Dordrecht, 1992, Tables 6.1.1.4 (pp. 500-502) and 4.2.6.8 (pp. 219-222). Structure solution, refinement, graphics and generation of publication materials were performed by using SHELXTL, V5.10 software. Additional details of data collection and structure refinement are given in Table 5 which follows.

EXAMPLE 6

Crystal Structure Analysis of Nabumetone: 2,3-naphthalenediol cocrystal (1:1)

A suitable cocrystal of nabumetone:2,3-naphthalenediol (1:1) was coated with Paratone N oil, suspended in a small fiber loop and placed in a cooled nitrogen gas stream at 100 K on a Bruker D8 SMART 1000 CCD sealed tube diffractometer with graphite monochromated $CuK_\alpha$ (1.54178 Å) radiation. Data were measured using a series of combinations of phi and omega scans with 10 second frame exposures and 0.3° frame widths. Data collection, indexing and initial cell refinements were all carried out using SMART software (SMART Version 5.55, 2000, Bruker AXS, Inc., Analytical X-ray Systems, 5465 East Cheryl Parkway, Madison Wis. 53711-5373). Frame integration and final cell refinements were done using SAINT software (SAINT Version 6.02, 1999, Bruker AXS, Inc., Analytical X-ray Systems, 5465 East Cheryl Parkway, Madison Wis. 53711-5373). The final cell parameters were determined from least-squares refinement on 2869 reflections.

The structure was solved using Direct methods and difference Fourier techniques (SHELXTL V5.10, 1997, Bruker AXS, Inc., Analytical X-ray Systems, 5465 East Cheryl Parkway, Madison Wis. 53711-5373). Hydrogen atoms were placed their expected chemical positions using the HFIX command and were included in the final cycles of least squares with isotropic $U_{ij}$'s related to the atom's ridden upon. The C-H distances were fixed at 0.93 Å (aromatic and amide), 0.98 Å (methine), 0.97 Å (methylene), or 0.96 Å (methyl). All non-hydrogen atoms were refined anisotropically. Scattering factors and anomalous dispersion corrections are taken from A. J. C. Wilson (ed), *International Tables for X-ray Crystallography, Volume C*. Kynoch, Academic Publishers, Dordrecht, 1992, Tables 6.1.1.4 (pp. 500-502) and 4.2.6.8 (pp. 219-222). Structure solution, refinement, graphics and generation of publication materials were performed by using SHELXTL, V5.10 software. Additional details of data collection and structure refinement are given in Table 6 which follows.

EXAMPLE 7

Cocrystals of Active Agent Salts and Guests

The experiments of Examples 1 and 2 are repeated, using conditions similar to those of those previous Examples, with each possible combination of the salts of active agents and guests identified earlier in this disclosure. Cocrystals are formed which have utility according to the known activity of the active agent.

EXAMPLE 8

Cocrystals of Active Agents and Guest Salts

The experiments of Example 3 are repeated, using conditions similar to those of those previous Examples, with each possible combination of the neutral or zwitterionic active agents and guest salts identified earlier in this disclosure. Cocrystals are formed which have utility according to the known activity of the active agent.

EXAMPLE 9

Cocrystallization of Fluoxetine HCl and Fumaric Acid

Cocrystals of fluoxetine HCl and succinic acid were prepared as follows. A 6.00 g sample of fluoxetine HCl and 1.01 g of fumaric acid were dissolved in 20 mL of ethanol with heating. The solution was filtered through a 0.2 μm nylon filter, concentrated to a volume of 0.8 mL, and cooled in an ice bath for 6 hours. The solid material was isolated on filter paper and allowed to dry in the air to give 5.74 g (82% yield) of fluoxetine HCl:fumaric acid (2:1) cocrystal. The measured melting points were 158° C. for fluoxetine HCl, >300° C. (decomposes) for fumaric acid, and 164° C. for the cocrystal. The cocrystal is expected to have a good toxicology profile, since fumaric acid is known to be safe and appears on the Generally Recognized As Safe ("GRAS") list from the U.S. Food and Drug Administration.

EXAMPLE 10

Crystal Structure Analysis of Fluoxetine HCl:Fumaric Acid Cocrystal (2:1)

A suitable cocrystal of fluoxetine HCl and fumaric acid was coated with Paratone N oil, suspended in a small fiber loop and placed in a cooled nitrogen gas stream at 100 K on a Bruker D8 SMART 1000 CCD sealed tube diffractometer with graphite monochromated CuKa (1.54178 Å) radiation. Data were measured using a series of combinations of phi and omega scans with 10 second frame exposures and 0.3° frame widths. Data collection, indexing and initial cell refinements were all carried out using SMART software (SMART Version 5.55, 2000, Bruker AXS, Inc., Analytical X-ray Systems, 5465 East Cheryl Parkway, Madison Wis. 53711-5373). Frame integration and final cell refinements were done using SAINT software (SAINT Version 6.02, 1999, Bruker AXS, Inc., Analytical X-ray Systems, 5465 East Cheryl Parkway, Madison Wis. 53711-5373). The final cell parameters were determined from least-squares refinement on 5625 reflections.

The structure was solved using Direct methods and difference Fourier techniques (SHELXTL V5.10, 1997, Bruker AXS, Inc., Analytical X-ray Systems, 5465 East Cheryl Parkway, Madison Wis. 53711-5373). All the hydrogen atoms were located from difference Fouriers and included in the final cycles of least squares with isotropic Uij's. All non-hydrogen atoms were refined anisotropically. Scattering factors and anomalous dispersion corrections are taken from A. J. C. Wilson (ed), International Tables for X-ray Crystallography, Volume C. Kynoch, Academic Publishers, Dordrecht, 1992, Tables 6.1.1.4 (pp. 500-502) and 4.2.6.8 (pp. 219-222). Structure solution, refinement, graphics and generation of publication materials were performed by using SHELXTL, V5.10 software. Additional details of data collection and structure refinement are given in Table G which follows.

All patents, test procedures, and other documents cited herein, including priority documents, are fully incorporated by reference to the extent such disclosure is not inconsistent with this invention and for all jurisdictions in which such incorporation is permitted.

While the present invention has been described and illustrated by reference to particular embodiments, it will be appreciated by those of ordinary skill in the art that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

TABLE 1

10-camphorsulfonic acid
10-undecylenic acid
1-hydroxy-2-naphthoic acid
2,4-dihydroxybenzoic acid
2,5-dihydroxybenzoic acid
2-aminopropionic acid
2-ethylbutyrinc acid
2-furancarboxylic acid
2-mercaptobenzoic acid
3-methylbutanoic acid
3-phenylpropionic acid
4-aminobenzoic acid
4-aminosalicylic acid
4-hydroxybenzoic acid
adipic acid
alginic acid
anisic acid
arginine
ascorbic acid
asparagine
aspartic acid
aspirin
benzenesulfonic acid
benzoic acid
4-acetamidobenzoic acid
beta-alanine
camphoric acid
camphorsulfonic acid
carbonic acid
cholic acid
cinnamic acid
citric acid
cyclamic acid
cyclohexanecarboxylic acid
cyclohexylacetic acid
cysteine
diphenylacetic acid
dodecylsulfonic acid
ethane-1,2-disulfonic acid
ethanesulfonic acid
ethanesulfonic acid, 2-hydroxy
ethylenediaminetetraacetic acid
ethylsulfuric acid
fumaric acid
galactaric acid
gallic acid
gentisic acid
glucoheptonic acid
gluconic acid
glutamic Acid
glutamine TABLE 1-continued glutaric acid
glutaric acid, 2-oxo-
glycine
glycolic acid
hippuric acid
histidine
hydroxyproline
isoleucine
lactobionic acid
lauric acid
leucine
levulinic acid
lysine
maleic acid
malic acid
malonic acid
mandelic acid
m-methoxybenzoic acid
naphthalene-1,5-disulfonic acid
naphthalene-2-sulfonic acid
n-decanoic acid
niacin
nicotinic acid
n-tetradecanoic acid
oleic acid
o-methylbenzoic acid
orotic acid
orthoboric acid
o-toluic acid
p-acetamidobenzoic acid
palmitic acid
pamoic acid
phenoxyacetic acid
phenylacetic acid
phenylalanine
picric acid
pivalic acid
proline
p-toluenesulfonic acid
pyroglutamic acid
pyruvic acid
salicylic acid
sebacic acid
serine
sorbic acid
stearic acid
succinic acid
sulfosalicylic acid
tartaric acid
terephthalic acid
thiocyanic acid
threonine
tiglic acid
tryptophan
tyrosine
valeric acid
valine

| Name | CAS # |
|---|---|
| Potassium bicarbonate | 298-14-6 |
| Potassium carbonate | 584-08-7 |
| Potassium chloride | 7447-40-7 |
| Potassium hydroxide | 1310-58-3 |
| Potassium metabisulfite | 16731-55-8 |
| Potassium nitrate | 7757-79-1 |
| Potassium nitrite | 7758-09-0 |
| Potassium permanganate | 7722-64-7 |
| Potassium persulfate | 7727-21-1 |
| Potassium phosphate, dibasic | 2139900 |
| Potassium phosphate Monobasic | 7778-77-0 |
| potassium phosphate, tribasic, n-hydrate | 7778-53-2 |
| Potassium sulfate | 7778-80-5 |
| Sodium bicarbonate | 144-55-8 |

| Name | CAS # |
|---|---|
| Sodium bisulfite | 7631-90-5 |
| Sodium borohydride | 16940-66-2 |
| Sodium carbonate | 497-19-8 |
| Sodium Carbonate Monohydrate | 1486118 |
| Sodium chloride | 7647-14-5 |
| Sodium dithionite | 7775-14-6 |
| Sodium fluoride | 7681-49-4 |
| Sodium hexametaphosphate | 10124-56-8 |
| Sodium hydroxide | 1310-73-2 |
| Sodium hypochlorite | 7681-52-9 |
| Sodium Metabisulfite | 7681-57-4 |
| Disodium metasilicate | 6834-92-0 |
| sodium monophosphate | 7681-53-0 |
| Sodium nitrate | 7631-99-4 |
| Sodium nitrite | 7632-00-0 |
| sodium hydrogen phosphate | 7558-79-4 |
| Sodium Phosphate Monobasic | 7558-80-7 |
| Sodium Pyrophosphate | 7722-88-5 |
| Sodium silicate | 1344-09-8 |
| Sodium Sulfate Decahydrate | 7727-73-3 |
| Sodium sulfite | 7757-83-7 |
| Sodium Thiosulfate Pentahydrate | 10102-17-7 |
| Calcium acetate | 5743-26-0 |
| Calcium Carbonate | 471-34-1 |
| Calcium Chloride Dihydrate | 10035-04-8 |
| Calcium gluconate | 299-28-5 |
| Calcium hydroxide | 1305-62-0 |
| Calcium oxide | 1305-78-8 |
| Calcium phosphate, dibasic | 7757-93-9 |
| Calcium Phosphate Monobasic | 7758-23-8 |
| Calcium sulfate | 7778-18-9 |
| Magnesium hydroxide | 1309-42-8 |
| Magnesium Sulfate Heptahydrate | 10034-99-8 |
| Aluminum | 7429-90-5 |
| Aluminum ammonium sulfate | 7784-26-1 |
| Aluminum chloride | 7446-70-0 |
| Aluminum hydroxide | 21645-51-2 |
| Aluminum potassium sulfate, dodecahydrate | 7784-24-9 |
| Orthoboric acid | 10043-35-3 |
| formaldehyde | 50-00-0 |
| DL-Isoleucine | 443-79-8 |
| (2S,7S)-(−)-Cystine | 56-89-3 |
| DL-Alanine | 302-72-7 |
| beta-Alanine | 107-95-9 |
| (S)-(+)-Arginine | 74-79-3 |
| (S)-(−)-Cysteine | 52-90-4 |
| DL-Glutamic acid | 617-65-2 |
| Glycine | 56-40-6 |
| (S)-(−)-Histidine | 71-00-1 |
| (S)-(+)-Lysine | 56-87-1 |
| DL-Methionine | 59-51-8 |
| DL-Phenylalanine | 150-30-1 |
| (S)-(−)-Phenylalanine | 63-91-2 |
| D-(+)-Proline | 344-25-2 |
| (S)-(−)-Tryptophan | 73-22-3 |
| (S)-(−)-Tyrosine | 60-18-4 |
| Carvone | 99-49-0 |
| Citral | 5392-40-5 |
| Ethyl butyrate | 105-54-4 |
| Isobutyl propionate | 540-42-1 |
| Methyl butyrate | 623-42-7 |
| n-Propyl acetate | 109-60-4 |
| Isobutyl formate | 542-55-2 |
| Benzyl acetate | 140-11-4 |
| 6-Methyl-5-hepten-2-one | 110-93-0 |
| Butyl acetate | 123-86-4 |
| Ethyl acetoacetate | 141-97-9 |
| Isopentyl Acetate | 123-92-2 |
| Cinnamaldehyde | 104-55-2 |
| Methyl benzoate | 93-58-3 |
| Butyl sulfide | 544-40-1 |
| Ethyl benzoate | 93-89-0 |
| 2,4-Hexadienoic acid, potassium salt, (E,E)- | 24634-61-5 |
| Potassium bitartrate | 868-14-4 |
| Lauric acid | 143-07-7 |
| Benzyl benzoate | 120-51-4 |
| Picric acid | 88-89-1 |
| Benzoyl peroxide | 94-36-0 |
| Palmitic acid | 57-10-3 |
| Dibutyl phthalate | 84-74-2 |
| Stearic acid | 57-11-4 |
| Succinic anhydride | 108-30-5 |
| Diethylenetriamine | 111-40-0 |
| Diethanolamine | 111-42-2 |
| Benzaldehyde | 100-52-7 |
| Phenethylamine | 64-04-0 |
| Salicylylaldehyde | 90-02-8 |
| Sodium benzoate | 532-32-1 |
| Cinnamic acid | 621-82-9 |
| Triethanolamine | 102-71-6 |
| L-(+)-Tartaric Acid | 87-69-4 |
| Eugenol | 97-53-0 |
| D-mannitol | 69-65-8 |
| Butyl paraben | 94-26-8 |
| Benzoin | 119-53-9 |
| Diethyl phthalate | 84-66-2 |
| Oleic acid | 112-80-1 |
| Sodium lactate | 72-17-3 |
| Indole | 120-72-9 |
| ethyl lactate | 97-64-3 |
| quinoline | 91-22-5 |
| Thymol | 89-83-8 |
| Methyl anthranilate | 134-20-3 |
| Methyl salicylate | 119-36-8 |
| Diethyl malonate | 105-53-3 |
| Citric acid | 77-92-9 |
| Sodium dodecyl sulfate | 151-21-3 |
| Morpholine | 110-91-8 |
| Furfural | 98-01-1 |
| Niacin | 59-67-6 |
| Choline chloride | 67-48-1 |
| L-Menthol | 2216-51-5 |
| Meso-inositol | 87-89-8 |
| ethylenediaminetetraacetic acid | 60-00-4 |
| EDTA, calcium derivative, disodium salt | 62-33-9 |
| Calcium pantothenate | 137-08-6 |
| Riboflavin | 83-88-5 |
| Zinc carbonate | 3486-35-9 |
| Amyl alcohol | 71-41-0 |
| Mineral oil | 8012-95-1 |
| Triton(R) X-100 | 9002-93-1 |
| Acetaldehyde | 75-07-0 |
| Acetic Acid | 64-19-7 |
| Acetone | 67-64-1 |
| Acetophenone | 98-86-2 |
| 4-Aminobenzoic acid | 150-13-0 |
| Anisole | 100-66-3 |
| Vitamin C | 50-81-7 |
| Benzoic Acid | 65-85-0 |
| Biphenyl | 92-52-4 |
| 2-Methyl-1-propanol | 78-83-1 |
| n-Butanol | 71-36-3 |
| n-Butylamine | 109-73-9 |
| ethyl acetate | 141-78-6 |
| Caffeine | 58-08-2 |
| Chloroacetic Acid | 79-11-8 |
| Dichloroacetic Acid | 79-43-6 |
| Diethylamine | 109-89-7 |
| Ethanol Amine | 141-43-5 |
| n-Butyric Acid | 107-92-6 |
| Ethylenediamine | 107-15-3 |
| Formic acid | 64-18-6 |
| n-Hexanol | 111-27-3 |
| Methanol | 67-56-1 |
| Methyl Acetate | 79-20-9 |
| Methyl 4-hydroxybenzoate | 99-76-3 |
| m-Cresol | 108-39-4 |
| p-Cresol | 106-44-5 |
| Phenol | 108-95-2 |
| n-Propanol | 71-23-8 |
| Propionic Acid | 79-09-4 |

| Name | CAS # |
|---|---|
| Salicylic acid | 69-72-7 |
| Sucrose | 57-50-1 |
| Vanillin | 121-33-5 |
| Vitamin E | 59-02-9 |
| Potassium citrate, monohydrate | 1534146 |
| p-toluenesulfonic acid monohydrate | 6192-52-5 |
| D-(+)-Maltose | 69-79-4 |
| Tetrasodium ethylenediaminetetraacetate | 64-02-8 |
| Saccharin sodium | 128-44-9 |
| Sodium Acetate Trihydrate | 6131-90-4 |
| Quinine sulfate, dihydrate | 6119-70-6 |
| Sulfosalicylic acid, dihydrate | 5965-83-3 |
| L-(+)-Arginine monohydrochloride | 1119-34-2 |
| Procaine hydrochloride | 51-05-8 |
| Pyridoxine Hydrochloride | 58-56-0 |
| Thiamine hydrochloride | 67-03-8 |
| Propionaldehyde | 123-38-6 |
| Urea | 57-13-6 |
| 2-Propanol | 67-63-0 |
| Pyrrole | 109-97-7 |
| Sodium formate | 141-53-7 |
| Pyrrolidine | 123-75-1 |
| Methyl ethyl ketone | 78-93-3 |
| Ethyl formate | 109-94-4 |
| Propylene glycol | 57-55-6 |
| Thiourea | 62-56-6 |
| Ammonium acetate | 631-61-8 |
| Benzene | 71-43-2 |
| Sodium acetate | 127-09-3 |
| Cyclopentanone | 120-92-3 |
| Cyclohexane | 110-82-7 |
| piperidine | 110-89-4 |
| 2-Pentanone | 107-87-9 |
| hexane | 110-54-3 |
| Isoamyl Alcohol | 123-51-3 |
| Lactic acid | 50-21-5 |
| 2-Ethoxyethanol | 110-80-5 |
| Propionic acid, sodium salt | 137-40-6 |
| Potassium acetate | 127-08-2 |
| cyclohexyl amine | 108-91-8 |
| methyl methacrylate | 80-62-6 |
| methyl isobutyl ketone | 108-10-1 |
| Acetic anhydride | 108-24-7 |
| Isopropyl Acetate | 108-21-4 |
| 2,2'-Oxybisethanol | 111-46-6 |
| Benzyl alcohol | 100-51-6 |
| Resorcinol | 108-46-3 |
| 2-Butoxy ethanol | 111-76-2 |
| Cumene | 98-82-8 |
| 2-Amino-2-(hydroxymethyl)-1,3-propanediol | 77-86-1 |
| Phenethyl alcohol | 60-12-8 |
| 2-Ethyl-1-hexanol | 104-76-7 |
| 2-Octanol | 123-96-6 |
| 2-(2-Ethoxyethoxy)ethanol | 111-90-0 |
| 2,6-Dimethyl-4-heptanone | 108-83-8 |
| Benzophenone | 119-61-9 |
| D-(−)-Fructose | 57-48-7 |
| D-Glucose | 50-99-7 |
| D-Ribose | 50-69-1 |
| D-(+)-Xylose | 58-86-6 |
| Pectin sugar | 5328-37-0 |
| D-(+)-Lactose | 63-42-3 |
| Camphene | 79-92-5 |
| Isoquinoline | 119-65-3 |
| 2,4-Dimethylphenol | 105-67-9 |
| 2,5-Dimethylphenol | 95-87-4 |
| 2,6-Dimethylphenol | 576-26-1 |
| Methanesulfonic Acid | 75-75-2 |
| o-Methoxybenzoic Acid | 579-75-9 |
| Saccharin | 81-07-2 |
| Thiazole | 288-47-1 |
| Trifluoromethanesulfonic Acid | 1493-13-6 |
| Trimethylamine | 75-50-3 |
| Coumarin | 91-64-5 |
| Dimethylamine | 124-40-3 |
| Ethyl Alcohol | 64-17-5 |
| Butyl benzyl phthalate | 85-68-7 |
| 2,6-dimethylpyrazine | 108-50-9 |
| taurocholic acid | 81-24-3 |
| geraniol | 106-24-1 |
| linalool | 78-70-6 |
| ethyl isovalerate | 108-64-5 |
| ethyl 2-methylbutyrate | 7452-79-1 |
| 1-octen-3-ol | 3391-86-4 |
| ethyl 2-trans-4-cis-decadienoate | 3025-30-7 |
| Dihydromyrcenol | 18479-58-8 |
| citronellal | 106-23-0 |
| linalyl acetate | 115-95-7 |
| 8-mercapto-p-menthan-3-one | 38462-22-5 |
| Ammonium citrate | 3012-65-5 |
| Ammonium bicarbonate | 1066-33-7 |
| Ammonium chloride | 12125-02-9 |
| Ammonium hydroxide | 1336-21-6 |
| Ammonium persulfate | 7727-54-0 |
| Ammonium phosphate, dibasic | 7783-28-0 |
| Ammonium Phosphate Monobasic | 7722-76-1 |
| Ammonium sulfate | 7783-20-2 |
| Ammonium sulfide | 12135-76-1 |
| Hydrazine | 302-01-2 |
| Nitric acid | 7697-37-2 |
| phosphoric acid | 7664-38-2 |
| Phosphorus oxychloride | 10025-87-3 |
| Hydriodic acid | 10034-85-2 |
| Hydrobromic acid | 10035-10-6 |
| Hydrochloric acid | 7647-01-0 |
| hydrogen peroxide | 7722-84-1 |
| Periodic Acid | 10450-60-9 |
| Sulfamic acid | 5329-14-6 |
| Sulfuric acid | 7664-93-9 |
| Sulfurous acid | 7782-99-2 |
| Dexpanthenol | 81-13-0 |
| 4-oxoisophorone | 1125-21-9 |
| Copper(II) sulfate | 7758-98-7 |
| ferric chloride | 7705-08-0 |
| Ferric oxide | 1309-37-1 |
| ferric sulfate | 10028-22-5 |
| Iron(II)Sulfate Heptahydrate | 7782-63-0 |
| Iron | 7439-89-6 |
| Manganese (II) Sulfate Monohydrate | 10034-96-5 |
| Nickel | 7440-02-0 |
| Titanium dioxide | 13463-67-7 |
| Zinc chloride | 7646-85-7 |
| Zinc oxide | 1314-13-2 |
| 1,1'-Azobisformamide | 123-77-3 |
| 1,3-Butanediol | 107-88-0 |
| 1-Methylnaphthalene | 90-12-0 |
| 2,6-Di-tert-Butyl-p-Cresol | 128-37-0 |
| 2,6-Dimethylpyridine | 108-48-5 |
| Disodium cyanodithioimidocarbonate | 138-93-2 |
| 3-Methyl-2-Cyclopentene-2-ol-one | 80-71-7 |
| 6-Methylcoumarin | 92-48-8 |
| acetoin | 513-86-0 |
| alpha-Phellandrene | 99-83-2 |
| alpha-Terpinene | 99-86-5 |
| Benzenesulfonic Acid | 98-11-3 |
| Benzothiazole | 95-16-9 |
| borates, tetrasodium salts | 1330-43-4 |
| Butyl butyrate | 109-21-7 |
| Butyl Mercaptan | 109-79-5 |
| Butyraldehyde | 123-72-8 |
| Capsaicin | 404-86-4 |
| Chloromethyl Methyl Ether | 107-30-2 |
| Cymene | 99-87-6 |
| Diallyl Disulfide | 2179-57-9 |
| Diethylaminoethanol | 100-37-8 |
| dimethyldisulfide | 624-92-0 |
| Dimethyl Succinate | 106-65-0 |
| Dimethyl Sulfate | 77-78-1 |

| Name | CAS # |
|---|---|
| Dimethyl Sulfide | 75-18-3 |
| Dipropyl Disulfide | 629-19-6 |
| Dipropyl Ketone | 123-19-3 |
| Ethyl Acrylate | 140-88-5 |
| Ethyl Butyl Ketone | 106-35-4 |
| Ethyl Propionate | 105-37-3 |
| Furfuryl Alcohol | 98-00-0 |
| gamma-Butyrolactone | 96-48-0 |
| Glutaraldehyde | 111-30-8 |
| glycerin | 56-81-5 |
| Glycolic Acid | 79-14-1 |
| Isobutyl Acetate | 110-19-0 |
| Isobutyl Isobutyrate | 97-85-8 |
| Isobutyraldehyde | 78-84-2 |
| Isoheptanol | 543-49-7 |
| Isophorone | 78-59-1 |
| Isopropyl Mercaptan | 75-33-2 |
| Methyl isobutenyl ketone | 141-79-7 |
| Methyl n-amyl ketone | 110-43-0 |
| methyl acrylate | 96-33-3 |
| Methyl Isobutyrate | 547-63-7 |
| Methyl Mercaptan | 74-93-1 |
| N,N-Dimethylethanolamine | 108-01-0 |
| n-Butyl Lactate | 138-22-7 |
| n-Hexyl Acetate | 142-92-7 |
| n-Valeraldehyde | 110-62-3 |
| Nitrous Oxide | 10024-97-2 |
| p-Anisaldehyde | 123-11-5 |
| 2-Methylcyclohexanone | 583-60-8 |
| Octanoic Acid | 124-07-2 |
| Oxalic Acid | 144-62-7 |
| Phenyl ether | 101-84-8 |
| Phenylmercaptan | 108-98-5 |
| Propargyl Alcohol | 107-19-7 |
| Propyl paraben | 94-13-3 |
| sec-Butyl Alcohol | 78-92-2 |
| Sodium Gluconate | 527-07-1 |
| Sodium Tripolyphosphate | 7758-29-4 |
| Tetrahydro-2-furanmethanol | 97-99-4 |
| Valeric Acid | 109-52-4 |
| 3,4-xylenol | 95-65-8 |
| 3-hexanol | 623-37-0 |
| 3-methyl-1-pentanol | 589-35-5 |
| 1,1-diethoxyethane | 105-57-7 |
| Aluminum Sulfate | 10043-01-3 |
| ammonium sulfite | 10196-04-0 |
| amyl butyrate | 540-18-1 |
| borneol | 507-70-0 |
| butyl formate | 592-84-7 |
| calcium peroxide | 1305-79-9 |
| n-Hexanoic Acid | 142-62-1 |
| cyclohexyl acetate | 622-45-7 |
| diacetyl | 431-03-8 |
| dimethyl carbonate | 616-38-6 |
| ethyl butyraldehyde | 97-96-1 |
| Ethyl crotonate | 623-70-1 |
| ethyl isobutyrate | 97-62-1 |
| ethyl nitrite | 109-95-5 |
| fumaric acid | 110-17-8 |
| hexaldehyde | 66-25-1 |
| isobutyric acid | 79-31-2 |
| methyl isovalerate | 556-24-1 |
| methyl propionate | 554-12-1 |
| methyl valeraldehyde | 123-15-9 |
| nitrosyl chloride | 2696-92-6 |
| octafluorocyclobutane | 115-25-3 |
| peroxyacetic acid | 79-21-0 |
| propyl formate | 110-74-7 |
| propyl mercaptan | 107-03-9 |
| Sodium aluminate | 1302-42-7 |
| sodium chlorite | 7758-19-2 |
| Terephthalic Acid | 100-21-0 |
| allyl isothiocyanate | 57-06-7 |
| Vitamin B1 | 59-43-8 |
| Valproic acid | 99-66-1 |
| Ethoxyquin | 91-53-2 |
| n-Amyl Ethyl Ketone | 106-68-3 |
| Nabam | 142-59-6 |
| Sodium sulfide | 1313-82-2 |
| Thiocyanic acid | 463-56-9 |
| 2-Methyl-5-(1-methylethenyl)-2-cyclohexene-1-one | 2244-16-8 |
| 4-(2,6,6-Trimethyl-2-cyclohexen-1-yl)-3-buten-2-one | 127-41-3 |
| 4-(2,6,6-trimethyl-1-cyclohexen-1-yl)-3-buten-2-one | 14901-07-6 |
| Isoamyl propionate | 105-68-0 |
| 3-Methylbutanoic acid | 503-74-2 |
| L-Menthone | 14073-97-3 |
| 4-Ethylphenol | 123-07-9 |
| o-cresol | 95-48-7 |
| dimethyl-Carbamodithioic acid, sodium salt | 128-04-1 |
| Anethole | 104-46-1 |
| Dimethyl terephthalate | 120-61-6 |
| propyl gallate | 121-79-9 |
| L-Ascorbic Acid Sodium Salt | 134-03-2 |
| 4-Hexylresorcinol | 136-77-6 |
| Estragole | 140-67-0 |
| L-monosodium glutamate | 142-47-2 |
| Malonaldehyde, sodium salt | 24382-04-5 |
| Butylated hydroxyanisole | 25013-16-5 |
| allyl 3-methylbutyrate | 2835-39-4 |
| DL-monosodium glutamate | 32221-81-1 |
| 3-Acetyl-6-methyl-2,4-pyrandione | 520-45-6 |
| L-Glutamic Acid | 56-86-0 |
| DL-alpha-tocopheryl acetate | 58-95-7 |
| D-limonene | 5989-27-5 |
| Calcium Acetate | 62-54-4 |
| Erythorbic Acid Monosodium Salt | 6381-77-7 |
| Ethyl methylphenylglycidate | 77-83-8 |
| 2,4,6-Trinitro-1,3-dimethyl-5-tert-butylbenzene | 81-15-2 |
| Dimethoxane | 828-00-2 |
| 3,5-Di-tert-butyl-4-hydroxybenzyl alcohol | 88-26-6 |
| 6-Methylquinoline | 91-62-3 |
| alpha-Methylbenzyl alcohol | 98-85-1 |
| Nicotinamide | 98-92-0 |
| 3,4-Dihydrocoumarin | 119-84-6 |
| Geranyl Acetate | 105-87-3 |
| Sodium (2-Ethylhexyl)Alcohol Sulfate | 126-92-1 |
| Cyclohexanol, 5-methyl-2-(1-methylethyl)-, (1alpha,2beta,5alpha)- | 89-78-1 |
| (+)-Camphor | 464-49-3 |
| (1S)-(−)-alpha-Pinene | 7785-26-4 |
| 1,3-Dihydroxy-5-methylbenzene | 504-15-4 |
| 1,5-Naphthalenedisulfonic Acid Disodium Salt | 1655-29-4 |
| 1-Hydroxy-2-naphthoic Acid | 86-48-6 |
| 1-Penten-3-ol | 616-25-1 |
| 1-Phenyl-1-propanol | 93-54-9 |
| 10-Undecylenic Acid | 112-38-9 |
| 2'-Hydroxyacetophenone | 118-93-4 |
| 2,4-Dihydroxybenzoic Acid | 89-86-1 |
| 2-Acetylfuran | 1192-62-7 |
| 2-Furancarboxylic Acid | 88-14-2 |
| 2-Isopropylphenol | 88-69-7 |
| 2-Ketoglutaric Acid | 328-50-7 |
| 2-Ketovaline | 759-05-7 |
| 2-n-Propylphenol | 644-35-9 |
| 2-Naphthalenethiol | 91-60-1 |
| 2-Phenyl-1-propanol | 1123-85-9 |
| 3,3'-Thiodipropionic Acid | 111-17-1 |
| 3,5,5-Trimethylhexanal | 5435-64-3 |
| 3-Phenyl-1-propanol | 122-97-4 |
| 3-Phenylpropionic Acid | 501-52-0 |
| 4-Aminosalicylic Acid | 65-49-6 |
| 4-Ethoxyphenol | 622-62-8 |
| 4-Hydroxybenzoic Acid | 99-96-7 |
| 4-Phenyl-2-butanol | 2344-70-9 |
| 4-tert-Octylphenol | 140-66-9 |

| Name | CAS # |
|---|---|
| Allyl Cinnamate | 1866-31-5 |
| Allyl Mercaptan | 870-23-5 |
| alpha-L-Rhamnose | 3615-41-6 |
| Alpha-Terpineol | 98-55-5 |
| Anisic Acid | 100-09-4 |
| Benzalacetone | 122-57-6 |
| Benzaldehyde Dimethylacetal | 1125-88-8 |
| Benzyl Ether | 103-50-4 |
| Benzyl Formate | 104-57-4 |
| Benzyl Mercaptan | 100-53-8 |
| Benzyl Salicylate | 118-58-1 |
| Calcium Citrate | 813-94-5 |
| Calcium Glycerophosphate | 27214-00-2 |
| Calcium Hypophosphite | 7789-79-9 |
| Calcium Iodate | 7789-80-2 |
| Propanoic acid, 2-hydroxy-, calcium salt (2:1) | 814-80-2 |
| Calcium Phosphate Tribasic | 7758-87-4 |
| Calcium Propionate | 4075-81-4 |
| Calcium Pyrophosphate | 7790-76-3 |
| Cholic Acid | 81-25-4 |
| Choline | 123-41-1 |
| Choline Bitartrate | 87-67-2 |
| trans-Cinnamic Aldehyde | 14371-10-9 |
| Cinnamyl Alcohol | 104-54-1 |
| Citronellol | 106-22-9 |
| Copper(I) Iodide | 7681-65-4 |
| D-(+)-Glucono-1,5-lactone | 90-80-2 |
| D-(−)-Tartaric Acid | 147-71-7 |
| D-Isoascorbic Acid | 89-65-6 |
| D-Tyrosine | 556-02-5 |
| Sodium dehydroacetate | 4418-26-2 |
| Deoxycholic Acid | 83-44-3 |
| Dibenzyl Ketone | 102-04-5 |
| Diethyl L-(+)-Tartrate | 87-91-2 |
| Diethyl Succinate | 123-25-1 |
| Dimethylacetal | 534-15-6 |
| DL-Cystine | 923-32-0 |
| DL-Proline | 609-36-9 |
| DL-Tartaric Acid | 133-37-9 |
| DL-Tyrosine | 556-03-6 |
| DL-Valine | 516-06-3 |
| Enanthoic Acid | 111-14-8 |
| Erythorbic Acid Sodium Salt | 7378-23-6 |
| Ethyl 2-Aminobenzoate | 87-25-2 |
| Ethyl Cinnamate | 103-36-6 |
| Ethyl n-Valerate | 539-82-2 |
| Ethyl Phenylacetate | 101-97-3 |
| Ethyl Salicylate | 118-61-6 |
| Ethyl Sulfide | 352-93-2 |
| Ethyl Vanillin | 121-32-4 |
| Ethylene Mercaptan | 540-63-6 |
| Farnesene | 502-61-4 |
| Folic acid | 59-30-3 |
| gamma-Nonanolactone | 104-61-0 |
| gamma-Valerolactone | 108-29-2 |
| Gluconic Acid | 526-95-4 |
| Gluconic Acid Potassium Salt | 299-27-4 |
| Glutaric Acid | 110-94-1 |
| Guanosine-5'-monophosphate, disodium salt | 1333479 |
| Heliotropine | 120-57-0 |
| Hippuric Acid | 495-69-2 |
| Hydroquinone Dimethyl Ether | 150-78-7 |
| Inosine-5'-monophosphate Sodium Salt | 4691-65-0 |
| iso-Amyl Mercaptan | 541-31-1 |
| Isoamyl Salicylate | 87-20-7 |
| iso-Butyl n-Hexanoate | 105-79-3 |
| isovaleraldehyde | 590-86-3 |
| Isoamyl Benzoate | 94-46-2 |
| Isoamyl Formate | 110-45-2 |
| Isoamyl n-Butyrate | 106-27-4 |
| Isoamylamine | 107-85-7 |
| Isobutyl n-Butyrate | 539-90-2 |
| Isocaproic Acid | 646-07-1 |
| Isoeugenol | 97-54-1 |
| Isopropyl Benzoate | 939-48-0 |
| Isopropyl Formate | 625-55-8 |
| Isopropyl N-Butyrate | 638-11-9 |
| Isopropyl Propionate | 637-78-5 |
| isobutyl Mercaptan | 513-44-0 |
| L-(+)-Isoleucine | 73-32-5 |
| L-(−)-Apple Acid | 97-67-6 |
| L-2-Aminopropionic Acid | 56-41-7 |
| L-Aspartic acid | 56-84-8 |
| L-Carnitine | 541-15-1 |
| L-Cysteine Hydrochloride | 52-89-1 |
| L-Glutamic Acid Hydrochloride | 138-15-8 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| N-Acetylglycine | 543-24-8 |
| n-Amyl Formate | 638-49-3 |
| n-Amyl n-Caproate | 540-07-8 |
| n-Butyl n-Caproate | 626-82-4 |
| n-Butyl Propionate | 590-01-2 |
| n-Butyl Salicylate | 2052-14-4 |
| n-Decanoic Acid | 334-48-5 |
| n-Hexyl Mercaptan | 111-31-9 |
| n-Propyl Benzoate | 2315-68-6 |
| n-Propyl Isobutyrate | 644-49-5 |
| n-Tetradecanoic Acid | 544-63-8 |
| Nitrilotriacetic Acid Trisodium Salt | 5064-31-3 |
| o-Toluenethiol | 137-06-4 |
| Orotic Acid | 65-86-1 |
| p-Acetamidobenzoic Acid | 556-08-1 |
| p-Anise Alcohol | 105-13-5 |
| Phenoxyacetic Acid | 122-59-8 |
| Phenyl Acetate | 122-79-2 |
| Piperine | 94-62-2 |
| Pivalic Acid | 75-98-9 |
| Potassium Benzoate | 582-25-2 |
| Potassium Diphosphate | 7320-34-5 |
| Potassium Hypophosphite | 7782-87-8 |
| Potassium Metaphosphate | 7790-53-6 |
| Potassium Sulfite | 10117-38-1 |
| Quinine Hydrochloride | 130-89-2 |
| sec-Amyl Alcohol | 6032-29-7 |
| Sodium D-Pantothenate | 867-81-2 |
| Di(2-ethylhexyl) sulfosuccinic acid, sodium salt | 577-11-7 |
| Sodium Sorbate | 7757-81-5 |
| Succinic acid, disodium salt | 150-90-3 |
| Sodium Taurocholate | 145-42-6 |
| Taurine | 107-35-7 |
| Thiamine Nitrate | 532-43-4 |
| Thioanisole | 100-68-5 |
| Tiglic Acid | 80-59-1 |
| Tri-n-butyrin | 60-01-5 |
| Triacetin | 102-76-1 |
| Trisodium Citrate | 68-04-2 |
| Veratraldehyde | 120-14-9 |
| Veratrole | 91-16-7 |
| Vitamin P | 520-26-3 |
| Vitamin U Chloride | 582174 |
| L-methionine | 63-68-3 |
| 2-Chloro-1-propanol | 78-89-7 |
| 2-Ethylbutyric acid | 88-09-5 |
| 2-Methylbutyraldehyde | 96-17-3 |
| 2-Methyl-5-ethylpyridine | 104-90-5 |
| n-propyl butyrate | 105-66-8 |
| Ethyl caprylate | 106-32-1 |
| Propyl propionate | 106-36-5 |
| 2-Methylpyrazine | 109-08-0 |
| 3,3,5-Trimethyl-1-cyclohexanol | 116-02-9 |
| Ethyl caproate | 123-66-0 |
| o-methoxybenzaldehyde | 135-02-4 |
| 2,4-Hexadienal | 142-83-6 |
| 3-Hexanone | 589-38-8 |
| 3-Methyl-2-butanol | 598-75-4 |
| Methyl isopropenyl ketone | 814-78-8 |

| Name | CAS # |
|---|---|
| 3-Methyl-2-butanethiol | 2084-18-6 |
| 3,5,5-Trimethylhexanol | 3452-97-9 |
| Methylglyoxal | 78-98-8 |
| Malonaldehyde | 542-78-9 |
| 1,4-Dithiane | 505-29-3 |
| Amylcinnamaldehyde | 122-40-7 |
| Benzyl cinnamate | 103-41-3 |
| tert-Butylhydroquinone | 1948-33-0 |
| Fusidic Acid Sodium Salt | 751-94-0 |
| Hydroxycitronellal | 107-75-5 |
| Musk ketone | 81-14-1 |
| L-Asparagine | 70-47-3 |
| phenethyl acetate | 103-45-7 |
| Riboflavin-5-Phosphate | 146-17-8 |
| Potassium Sodium Tartrate | 304-59-6 |
| Galactaric acid | 526-99-8 |
| Sodium Tartrate | 868-18-8 |
| trisodium phosphate | 7601-54-9 |
| Disodium Pytophosphate | 7758-16-9 |
| Magnesium chloride | 7786-30-3 |
| Sodium Polymethacrylate | 54193-36-1 |
| propiophenone | 93-55-0 |
| 2-ethylhexanoic acid | 149-57-5 |
| 3,7,7-trimethyl bicyclohep-3-ene | 13466-78-9 |
| 2,6-dimethyl-4-heptanol | 108-82-7 |
| 5-isopropyl-2-methyl-phenol | 499-75-2 |
| L-Bornyl acetate | 5655-61-8 |
| caryophyllene | 87-44-5 |
| hydroxymethylpyrone | 118-71-8 |
| neosperidin dihydrochalcone | 20702-77-6 |
| 2,2-Dibromo-3-nitrilopropionamide | 10222-01-2 |
| Xylitol | 87-99-0 |
| Sulfosalicylic acid | 97-05-2 |
| Riboflavin 5'-(dihydrogen phosphate), monosodium salt | 130-40-5 |
| Ethylenediaminetetraacetic acid, disodium salt | 139-33-3 |
| Gallic acid | 149-91-7 |
| Carbonic acid | 463-79-6 |
| Potassium carbonate, sesquihydrate | 6381-79-9 |
| Magnesium phosphate tribasic | 7757-87-1 |
| diallyl sulfide | 592-88-1 |
| ethyl 4-oxopentanoate | 539-88-8 |
| methyl caproate | 106-70-7 |
| isopropyl isobutyrate | 617-50-5 |
| diethyl hydroxybutanedioate | 2065419 |
| propyl isopentanoate | 557-00-6 |
| benzyl ethyl ether | 539-30-0 |
| isobutyl isopentanoate | 589-59-3 |
| propyl hexanoate | 626-77-7 |
| 4-methylquinoline | 491-35-0 |
| methyl cinnamate | 103-26-4 |
| cumic alcohol | 536-60-7 |
| thujone | 471-15-8 |
| dihydrocarveol | 619-01-2 |
| fenchyl alcohol | 1632-73-1 |
| Nerol | 106-25-2 |
| isopentyl isopentanoate | 659-70-1 |
| methyleugenol | 93-15-2 |
| methyl 2-naphthyl ketone | 93-08-3 |
| diphenyldisulfide | 882-33-7 |
| citronellyl acetate | 150-84-5 |
| menthyl acetate | 89-48-5 |
| menthyl isovalerate | 16409-46-4 |
| 5-Ethyl-3-hydroxy-4-methyl-2(5H)-furanone | 698-10-2 |
| malic acid | 6915-15-7 |
| 3-methylbutanoic acid butyl ester | 109-19-3 |
| 3-phenyloxiranecarboxylic acid ethyl ester | 121-39-1 |
| 1,2-Benzisothiazol-3(2H)-one 1,1-dioxide, ammonium salt | 6381-61-9 |
| 1-methyl-4-(1-methylethyl)-1,4-Cyclohexadiene | 99-85-4 |
| 3-mercapto-2-Butanol | 54812-86-1 |
| (1R)-2,6,6-trimethylbicyclo[3.1.1]hept-2-ene | 7785-70-8 |
| (1S)-6,6-dimethyl-2-methylenebicyclo[3.1.1]heptane | 18172-67-3 |
| 1-methyl-4-(1-methylethylidene)cyclohexene | 586-62-9 |
| 1-(3-pyridinyl)ethanone | 350-03-8 |
| 1-pyrazinylethanone | 22047-25-2 |
| 1-(2-furyl)-2-propanone | 6975-60-6 |
| 1-Penten-3-one | 1629-58-9 |
| 2,3-pentanedione | 600-14-6 |
| 2,5-dimethylpyrazine | 123-32-0 |
| 2-isobutyl-3-methoxypyrazine | 24683-00-9 |
| 4-methyl-2,3-pentanedione | 7493-58-5 |
| 5-methylfurfural | 620-02-0 |
| Dimethyltrisulfide | 3658-80-8 |
| furfuryl acetate | 623-17-6 |
| furfurylmethylether | 13679-46-4 |
| terpinen-4-ol | 562-74-3 |
| Calcium sorbate | 7492-55-9 |
| Potassium lactate | 996-31-6 |
| 1-Hydroxyethylidene-1,1-diphosphonic acid | 2809-21-4 |
| L-glutamic acid monopotassium salt | 19473-49-5 |
| 3-methyl-2-buten-1-ol | 556-82-1 |
| phenylethanal | 122-78-1 |
| 4'-Methoxyacetophenone | 100-06-1 |
| L-borneol | 464-45-9 |
| 2,4-Hexadien-1-ol | 111-28-4 |
| D-Fenchone | 4695-62-9 |
| 3-Phenylpropyl formate | 104-64-3 |
| Cinnamyl formate | 104-65-4 |
| D-galacturonate | 685-73-4 |
| D-glucuronate | 1700908 |
| 5' IMP | 131-99-7 |
| 1-Methoxy-4-methylbenzene | 104-93-8 |
| 2-Methylbutanoic acid | 116-53-0 |
| 2,4,6-Tribromophenol | 118-79-6 |
| 3-Ethyl pyridine | 536-78-7 |
| Zinc acetate | 557-34-6 |
| Methyl pentanoate | 624-24-8 |
| Methylthioethane | 624-89-5 |
| 3-Penten-2-one | 625-33-2 |
| Glycocholic acid | 475-31-0 |
| m-Methoxybenzoic acid | 586-38-9 |
| alpha-Hydroxypropionic acid | 598-82-3 |
| Methyl 2-furoate | 611-13-2 |
| 2-Furancarboxylic acid, propyl ester | 615-10-1 |
| Benzylacetoacetic acid, ethyl ester | 620-79-1 |
| 2,5-Dimethyl pyrrole | 625-84-3 |
| 4-methyl-1,1'-biphenyl | 644-08-6 |
| p-Isopropylacetophenone | 645-13-6 |
| 4-methyl-thiazole | 693-95-8 |
| gamma-Decalactone | 706-14-9 |
| 2-acetylpyrrole | 1072-83-9 |
| 2-acetylpyridine | 1122-62-9 |
| tetramethyl-pyrazine | 1124-11-4 |
| Methyl 4-phenylbutyrate | 2046-17-5 |
| 2,3,6-trimethyl-phenol | 2416-94-6 |
| 2-Methoxypyrazine | 3149-28-8 |
| 2-Ethylfuran | 3208-16-0 |
| 2,3-dimethyl-pyrazine | 5910-89-4 |
| Thiophenethiol | 7774-74-5 |
| o-Tolyl isobutyrate | 36438-54-7 |
| cis-3-Hexenyl pyruvate | 68133-76-6 |
| cis-3-Hexenyl cis-3-hexenoate | 61444-38-0 |
| trans-2-Hexenyl isovalerate | 68698-59-9 |
| trans-2-Hexenyl formate | 53398-78-0 |
| trans-2-Hexenyl valerate | 56922-74-8 |
| 1-Octen-3-yl butyrate | 16491-54-6 |
| Methyl 4-(methylthio)butyrate | 53053-51-3 |
| 2,4-Octadien-1-ol | 18409-20-6 |
| 2,4-Nonadien-1-ol | 62488-56-6 |

| Name | CAS # |
|---|---|
| 2,4-Decadien-1-ol | 18409-21-7 |
| (e,z)-2,6-Nonadienyl acetate | 68555-65-7 |
| 3-Hexenal | 4440-65-7 |
| Tetrahydro-2-furanmethanol acetate | 637-64-9 |
| Methyl benzaldehyde | 1334-78-7 |
| Dodecylsulfonic acid | 1510-16-3 |
| Methylethyl disulfide | 4253-89-8 |
| Farnesol | 4602-84-0 |
| Thiobenzoic acid, S-methyl ester | 5925-68-8 |
| Hexyl benzoate | 6789-88-4 |
| 2,5-Diethyltetrahydrofuran | 41239-48-9 |
| Zinc hydrosulfite | 7779-86-4 |
| (2R,3S)-Tartaric Acid | 147-73-9 |
| Ethylsulfuric acid | 540-82-9 |
| 1,2,2-Trimethyl-1,3-cyclopentanedicarboxylic acid | 5394-83-2 |
| 2-Methyl-3-buten-2-ol | 115-18-4 |
| trans-2-Hexenal | 6728-26-3 |
| 4-Hexen-3-one | 2497-21-4 |
| 1-Hexen-3-ol | 4798-44-1 |
| 2-Methyl-1-butanethiol | 1878-18-8 |
| 4-Methylcyclohexanone | 589-92-4 |
| 3-Heptanol | 589-82-2 |
| o-methylanisole | 578-58-5 |
| trans-2-octenal | 2363-89-5 |
| 2,3,4-Trimethyl-3-pentanol | 3054-92-0 |
| Acetylacetaldehyde dimethyl acetal | 5436-21-5 |
| p-methylacetophenone | 122-00-9 |
| o-aminoacetophenone | 551-93-9 |
| 4-Propylphenol | 645-56-7 |
| 2,4-Dimethylanisole | 6738-23-4 |
| Benzyl methyl sulfide | 766-92-7 |
| Methyl phenylacetate | 101-41-7 |
| 4-Ethoxybenzaldehyde | 10031-82-0 |
| p-tolyl acetate | 140-39-6 |
| 2,6-Dimethoxyphenol | 91-10-1 |
| Isoborneol | 124-76-5 |
| Methyl 2-methoxybenzoate | 606-45-1 |
| Phenylacetaldehyde dimethyl acetal | 101-48-4 |
| 3-Phenylpropyl acetate | 122-72-5 |
| Ethyl 3-phenylpropionate | 2021-28-5 |
| Benzyl butyrate | 103-37-7 |
| Anisyl acetate | 104-21-2 |
| Isobutyl phenylacetate | 102-13-6 |
| p-vinylphenol | 2628-17-3 |
| o-tolyl acetate | 533-18-6 |
| 2,5-Dihydroxybenzoic acid | 490-79-9 |
| o-methoxyphenyl acetate | 613-70-7 |
| Lactobionic acid | 96-82-2 |
| Magnesium hydrogen phosphate trihydrate | 7782-75-4 |
| Iberverin | 505-79-3 |
| alpha-methylcinnamaldehyde | 101-39-3 |
| benzyl phenylacetate | 102-16-9 |
| 1,3-dimercaptopropane | 109-80-8 |
| p-cymen-8-ol | 1197-01-9 |
| phenethyl anthranilate | 133-18-6 |
| trihydroxybutyrophenone | 1421-63-2 |
| o-methoxycinnamaldehyde | 1504-74-1 |
| 3-propylidene phthalide | 17369-59-4 |
| trans,trans-2,4-decadienal | 25152-84-5 |
| piperonyl acetate | 326-61-4 |
| 2,3-hexanedione | 3848-24-6 |
| isopropyl phenylacetate | 4861-85-2 |
| ethyl 3-hydroxybutyrate | 5405-41-4 |
| furfural acetone | 623-15-4 |
| beta-(2-furyl)acrolein | 623-30-3 |
| linalyl anthranilate | 7149-26-0 |
| citral diethyl acetal | 7492-66-2 |
| allyl anthranilate | 7493-63-2 |
| acetyl tributyl citrate | 77-90-7 |
| butyl anthranilate | 7756-96-9 |
| cyclohexyl anthranilate | 7779-16-0 |
| isoamyl cinnamate | 7779-65-9 |
| isobutyl anthranilate | 7779-77-3 |
| carvyl acetate | 97-42-7 |
| carveol | 99-48-9 |
| 3-(Methylthio)propionaldehyde | 3268-49-3 |
| Alpha-damascone | 43052-87-5 |
| Dimethyldicarbonate | 4525-33-1 |
| Procaine | 59-46-1 |
| 5-hydroxy-6-methyl-3,4-pyridinedimethanol | 65-23-6 |
| 2-methoxy-Naphthalene | 93-04-9 |
| Methyl nicotinate | 93-60-7 |
| Ethyl benzoylacetate | 94-02-0 |
| Phenethyl benzoate | 94-47-3 |
| 2-methyl-pentanoic acid | 97-61-0 |
| Cyclohexanecarboxylic acid | 98-89-5 |
| Methyl b-phenylpropionate | 103-25-3 |
| Benzyl 3-methyl butanoate | 103-38-8 |
| Naphthalene-2-sulfonic acid | 120-18-3 |
| Methyl 4-methoxybenzoate | 121-98-2 |
| 3-Phenylprop-2-enyl cinnamate | 122-69-0 |
| 7-methyl-3-methylene-1,6-Octadiene | 123-35-3 |
| Levulinic acid | 123-76-2 |
| 2-Mercaptobenzoic acid | 147-93-3 |
| m-Dimethoxybenzene | 151-10-0 |
| 3-butyl-1(3H)-isobenzofuranone | 6066-49-5 |
| 5-Methylquinoxaline | 13708-12-8 |
| 2-Ethyl Pyrazine | 13925-00-3 |
| trimethyl-pyrazine | 14667-55-1 |
| 2-ethyl-3-methyl-pyrazine | 15707-23-0 |
| 2,3-diethyl-pyrazine | 15707-24-1 |
| 2,3-diethyl-5-methyl-pyrazine | 18138-04-0 |
| 2-Methylthiopyrazine | 21948-70-9 |
| 5-Methyl-3H-furan-2-one | 591-12-8 |
| cis-3-Hexen-1-ol | 928-96-1 |
| 3,7-Dimethyl-1,3,6-octatriene | 13877-91-3 |
| calcium cyclamate | 139-06-0 |
| aconitic acid | 499-12-7 |
| 2-Dehydrolinalool | 29171-20-8 |
| 2-Mercaptopropionic acid | 79-42-5 |
| 3-Methyl-2-butenal | 107-86-8 |
| Allylacetic acid | 591-80-0 |
| Allyl cyclohexylacetate | 4728-82-9 |
| Allyl cyclohexylpropionate | 2705-87-5 |
| Allyl phenoxyacetate | 7493-74-5 |
| Allyl phenylacetate | 1797-74-6 |
| Allyl alpha-ionone | 79-78-7 |
| Butyl butyrolactate | 7492-70-8 |
| Cinnamyl isobutyrate | 103-59-3 |
| Cinnamyl propionate | 103-56-0 |
| Dibenzyl disulfide | 150-60-7 |
| Isobornyl acetate | 125-12-2 |
| Methyl heptyne carbonate | 111-12-6 |
| Triethyl citrate | 77-93-0 |
| gamma-Undecalactone | 104-67-6 |
| alpha-Amylcinnamyl alcohol | 101-85-9 |
| 1,3,4,6,7,8-Hexahydro-4,6,6,7,8,8-hexamethyl cyclopenta[g][2]benzopyran | 1222-05-5 |
| 2-Ethylbutyl acetate | 10031-87-5 |
| Triphosphoric acid, pentapotassium salt | 13845-36-8 |
| L-(+)-Lactic acid | 79-33-4 |
| Mannitol | 87-78-5 |
| 2-Methoxy-4-methylphenol | 93-51-6 |
| 1,2,3-Propanetricarboxylic acid, 2-hydroxy-, disodium salt | 144-33-2 |
| Ethanesulfonic acid, 2-hydroxy-, monosodium salt | 1562-00-1 |
| 2-Methoxy-4-propylphenol | 2785-87-7 |
| 3,7-Dimethyl-3-octanol | 78-69-3 |
| 2-Pentyl furan | 3777-69-3 |
| Butanoic acid, 3-oxo-, butyl ester | 591-60-6 |
| 4-(4-Hydroxy-4-methyl pentyl)-3-cyclohexene-1-carboxaldehyde | 31906-04-4 |

| Name | CAS # |
|---|---|
| Methyl 3-oxo-2-pentylcyclopentaneacetate | 24851-98-7 |
| Naphthalene, 2-(2-methylpropoxy)- | 2173-57-1 |
| Perillol | 536-59-4 |
| 2-Acetyl-1-methylpyrrole | 932-16-1 |
| 4-Allyl-2,6-dimethoxyphenol | 6627-88-9 |
| Butyl levulinate | 2052-15-5 |
| D-(+)-Camphoric acid | 124-83-4 |
| D(+)-10-Camphorsulfonic acid | 3144-16-9 |
| L-(−)-Carvone | 6485-40-1 |
| (−)-Carvyl propionate | 97-45-0 |
| (−)-Caryophyllene oxide | 1139-30-6 |
| Cyclohexylacetic acid | 5292-21-7 |
| 3-Cyclopentylpropionic acid | 140-77-2 |
| (−)-Dihydrocarvyl acetate | 20777-49-5 |
| 3,3-Dimethylacrylic acid | 541-47-9 |
| 2,4-Dimethylbenzaldehyde | 15764-16-6 |
| 1,4-Dithiane-2,5-diol | 40018-26-6 |
| Ethanesulfonic acid | 594-45-6 |
| Ethyl butyrylacetate | 3249-68-1 |
| Ethyl (methylthio)acetate | 4455-13-4 |
| Ethyl pyruvate | 617-35-6 |
| Ethyl sorbate | 2396-84-1 |
| 5-Formyl-2-furansulfonic acid, sodium salt | 31795-44-5 |
| Furfuryl mercaptan | 98-02-2 |
| 1,6-Hexanedithiol | 1191-43-1 |
| trans-2-Hexenoic acid | 13419-69-7 |
| trans-2-Hexen-1-ol | 928-95-0 |
| 4-(4-Hydroxyphenyl)-2-butanone | 5471-51-2 |
| Isopulegol | 89-79-2 |
| Isopulegyl acetate | 89-49-6 |
| 2-Ketobutyric acid | 600-18-0 |
| (−)-Limonene | 5989-54-8 |
| 4-Methoxyphenylacetone | 122-84-9 |
| Methyl cyclohexanecarboxylate | 4630-82-4 |
| 3-Methylcyclohexanone | 591-24-2 |
| 3-Methyl-2-cyclohexen-1-one | 1193-18-6 |
| 3-Methyl-1,2-cyclopentanedione | 765-70-8 |
| 3-Methyl-2-cyclopenten-1-one | 2758-18-1 |
| N-Methyl-D-glucamine | 6284-40-8 |
| Methyl 3-(methylthio)propionate | 13532-18-8 |
| 4-Methyl-5-thiazoleethanol | 137-00-8 |
| 5-Methyl-2-thiophenecarboxaldehyde | 13679-70-4 |
| DL-3-Methylvaleric acid | 105-43-1 |
| (−)-Myrtenal | 564-94-3 |
| Nopol | 128-50-7 |
| gamma-Octanoic lactone | 104-50-7 |
| 3-Octanol | 589-98-0 |
| E-2-Octenoic acid | 1871-67-6 |
| Pamoic acid | 130-85-8 |
| 4-Phenyl-2-butyl acetate | 10415-88-0 |
| 1-Phenyl-1,2-propanedione | 579-07-7 |
| 2-Phenylpropyl butyrate | 80866-83-7 |
| 2-Phenylpropyl isobutyrate | 65813-53-8 |
| cis-2-Hexen-1-ol | 928-94-9 |
| Bis(methylthio)methane | 1618-26-4 |
| Magnesium carbonate hydroxide, Light | 39409-82-0 |
| N-Acetyl-L-methionine | 65-82-7 |
| 4-Methyl-5-vinylthiazole | 1759-28-0 |
| 2-Methyl-1-phenyl-2-propanol | 100-86-7 |
| 3-Phenylpropionaldehyde | 104-53-0 |
| N-Benzyl-2-phenylethylamine | 3647-71-0 |
| 1-Phenylethyl propionate | 120-45-6 |
| 3-Phenylpropyl isobutyrate | 103-58-2 |
| Allyl hexanoate | 123-68-2 |
| alpha, 4-Dimethylbenzylalcohol | 536-50-5 |
| (−)-Menthyl lactate | 59259-38-0 |
| 2,6-Dimethylthiophenol | 118-72-9 |
| 2,4,5-Trimethylthiazole | 13623-11-5 |
| Ethyl 3-(methylthio)propionate | 13327-56-5 |
| Phenylethyl isovalerate | 140-26-1 |
| 2-Propylpyrazine | 18138-03-9 |
| 2-Methyltetrahydrofuran-3-one | 3188-00-9 |
| Ethyl 2-(methyldithio)propionate | 23747-43-5 |
| 3,4-Dimethyl-1,2-cyclopentanedione | 13494-06-9 |
| Difurfurylsulfide | 13678-67-6 |
| Difurfuryldisulfide | 4437-20-1 |
| 3-(Methylthio)propanol | 505-10-2 |
| Methyl phenyl disulfide | 14173-25-2 |
| 2-(Methyldithio)-isobutyraldehyde | 67952-60-7 |
| Methyl 2-thiofuroate | 13679-61-3 |
| 2-Isobutylthiazole | 18640-74-9 |
| 4-Methyl-5-thiazolylethyl acetate | 656-53-1 |
| 2-Acetylthiazole | 24295-03-2 |
| 2-Ethyl-3,5(6)-dimethylpyrazine | 27043-05-6 |
| 5-Methyl-6,7-dihydro-5H-cyclopenta(b)pyrazine | 23747-48-0 |
| Cinnamyl acetate | 103-54-8 |
| 2,5-Dihydroxy-2,5-dimethyl-1,4-dithiane | 55704-78-4 |
| 5,6,7,8-Tetrahydroquinoxaline | 34413-35-9 |
| 2-Methyl-3-furanethiol | 28588-74-1 |
| Styrallyl acetate | 93-92-5 |
| 2-Methylhexanoic acid | 4536-23-6 |
| 2-Methylheptanoic acid | 1188-02-9 |
| 2,2,6-Trimethylcyclohexanone | 2408-37-9 |
| L-Tyrosine ethyl ester hydrochloride | 4089-07-0 |
| Ethyl 4-methoxybenzoate | 94-30-4 |
| 4-Ethylbenzaldehyde | 4748-78-1 |
| N-Ethyl-p-menthane-3-carboxamide | 39711-79-0 |
| 1-(2-Furyl)-1,3-butanedione | 25790-35-6 |
| Menthofuran | 494-90-6 |
| Methylsulfuric acid sodium salt | 512-42-5 |
| Sucrose diacetate hexaisobutyrate | 126-13-6 |
| N,2,3-Trimethyl-2-isopropylbutamide | 51115-67-4 |
| Tripropionin | 139-45-7 |
| (+/−)-Citronellic acid | 502-47-6 |
| 5-Acetyl-2,4-dimethylthiazole | 38205-60-6 |
| Neryl acetate | 141-12-8 |
| Benzyl propionate | 122-63-4 |
| 1R-(−)-Camphorsulfonic acid | 35963-20-3 |
| 3,4-Hexanedione | 4437-51-8 |
| cis-3-Hexenoic acid | 4219-24-3 |
| cis-4-Heptenal | 6728-31-0 |
| (E,Z)-2,6-nonadienal | 557-48-2 |
| trans-2,trans-6-Nonadienal | 17587-33-6 |
| 4-Methyl-2-pentenal | 5362-56-1 |
| cis-6-Nonenal | 2277-19-2 |
| Methyl propyl disulfide | 2179-60-4 |
| 8-p-Menthen-1-ol | 138-87-4 |
| p-Menthan-2-one | 499-70-7 |
| Bisabolene | 495-62-5 |
| Ethyl cyclohexanecarboxylate | 3289-28-9 |
| Phenylpyruvate | 156-06-9 |
| Hydroxypyruvate | 1113-60-6 |
| 4-Methyl-2-oxopentanoate | 816-66-0 |
| (+)-Neomenthol | 2216-52-6 |
| trans-Citral | 141-27-5 |
| Piperitenone | 491-09-8 |
| Sabinene hydrate | 546-79-2 |
| Perillyl aldehyde | 2111-75-3 |
| 2-Hydroxyethanesulfonate | 107-36-8 |
| Acetyl isovaleryl | 13706-86-0 |
| Acetyl valeryl | 96-04-8 |
| Butylidene phthalide | 551-08-6 |
| Carvacryl ethyl ether | 4732-13-2 |
| Ethyl vanillin propylene glycol acetal | 68527-76-4 |
| Hexyl hexanoate | 6378-65-0 |
| 2-Methyl-5-(methylthio)-furan | 13678-59-6 |
| 2-Methyl-4-pentenoic acid | 1575-74-2 |

-continued

| Name | CAS # |
|---|---|
| 2-Methyl-4-propyl-1,3-oxathiane | 67715-80-4 |
| 3-Methylthio-1-hexanol | 51755-66-9 |
| cis-6-Nonenol | 35854-86-5 |
| Rose oxide | 16409-43-1 |
| L-Linalool | 126-91-0 |
| 5,6-Dimethyl-8-isopropenylbicyclo[4.4.0]dec-1-en-3-one | 4674-50-4 |
| 2-Ethyl-3,5-dimethylpyrazine | 13925-07-0 |
| 2-Isopropylpyrazine | 29460-90-0 |
| 2-Isobutyl-3-methyl-pyrazine | 13925-06-9 |
| 2-Methoxy-3-sec-butyl-pyrazine | 24168-70-5 |
| 2-Methylthio-3(6)-methyl-pyrazine | 67952-65-2 |
| Benzylcarbinyl propionate | 122-70-3 |
| Bornyl acetate | 76-49-3 |
| furaneol | 3658-77-3 |
| Methoxycinnamaldehyde | 1963-36-6 |
| Methylphenol, hydrogen sulfate | 68127-34-4 |
| Lactitol monohydrate | 81025-04-9 |
| 2H-Pyrrole, 3,4-dihydro- | 5724-81-2 |
| 2-Butenal, 2-methyl-, (E)- | 497-03-0 |
| 2-Pentenal | 764-39-6 |
| Ethanethioic acid, S-methyl ester | 1534-08-3 |
| 2-Hexenal | 505-57-7 |
| 2-Methyl-2-pentenal | 623-36-9 |
| Cyclopentanethiol | 1679-07-8 |
| Butane, 2-ethoxy- | 2679-87-0 |
| S-Ethyl thioacetate | 625-60-5 |
| ethyl methyl carbonate | 623-53-0 |
| 3(2H)-Furanone, 2,5-dimethyl- | 14400-67-0 |
| Allyl propionate | 2408-20-0 |
| methyl 2-methylbutanoate | 868-57-5 |
| 2-Butanone, 1-(methylthio)- | 13678-58-5 |
| Ethanethioic acid, S-propyl ester | 2307-10-0 |
| 1,2-Butanedithiol | 16128-68-0 |
| 6-Methyl-3,5-heptadiene-2-one | 1604-28-0 |
| 2-Octen-4-one | 4643-27-0 |
| 2,5-dimethyl-3-furanthiol | 55764-23-3 |
| 2-Heptenoic acid | 18999-28-5 |
| Butanoic acid, 2-propenyl ester | 2051-78-7 |
| 6-Methyl-5-hepten-2-ol | 1569-60-4 |
| trans-2-Octen-4-ol | 20125-81-9 |
| cis-2-Octen-1-ol | 20125-84-2 |
| 1-Butanol, 2-methyl-, acetate | 624-41-9 |
| 4-methyl-alpha-methylstyrene | 1195-32-0 |
| trans-3-Phenyl-2-propen-1-ol | 4407-36-7 |
| Benzeneacetaldehyde, alpha-methyl- | 93-53-8 |
| Benzene, (2-methoxyethyl)- | 3558-60-9 |
| Cyclohexene, 1-methyl-4-(1-methylethenyl)-, (+−)- | 7705-14-8 |
| Phenol, 2-(methylthio)- | 1073-29-6 |
| 2-Hexen-1-yl acetate | 2497-18-9 |
| 3-Hexen-1-ol, acetate, (Z)- | 3681-71-8 |
| 5-Hydroxy-4-octanone | 496-77-5 |
| butyl 2-methylpropanoate | 97-87-0 |
| Benzofuran-2-carboxaldehyde | 4265-16-1 |
| DL-Lysine | 70-54-2 |
| 1-Hexanethiol, 2-ethyl- | 7341-17-5 |
| 2',4'-Dimethylacetophenone | 89-74-7 |
| 2-Pentylpyridine | 2294-76-0 |
| 1-Methoxy-4-propyl benzene | 104-45-0 |
| 1-Hydroxy-2-methoxy-4-ethyl benzene | 2785-89-9 |
| Nonalactone | 6008-27-1 |
| Cyclohexyl propionate | 6222-35-1 |
| Allyl 2-ethylbutyrate | 7493-69-8 |
| Butanoic acid, 3-oxo-, 2-methylpropyl ester | 7779-75-1 |
| n-Butyl pentanoate | 591-68-4 |
| 3,7-Dimethyl-1-octanol | 106-21-8 |
| 3-Buten-2-one, methyl-4-phenyl- | 1901-26-4 |

-continued

| Name | CAS # |
|---|---|
| 2-Propenoic acid, 3-phenyl-, methyl ester, (E)- | 1754-62-7 |
| Benzene, 4-ethenyl-1,2-dimethoxy- | 6380-23-0 |
| Benzenepropanol, alpha,alpha-dimethyl- | 103-05-9 |
| Benzene, (butoxymethyl)- | 588-67-0 |
| Dimethyl anthranilate | 85-91-6 |
| 2-Hexanoylfuran | 14360-50-0 |
| Cyclohexyl butyrate | 1551-44-6 |
| Naphthalene, 2-ethoxy- | 93-18-5 |
| Acetoacetic acid isoamyl ester | 2308-18-1 |
| Propanoic acid, 2-methyl-, 4-methylphenyl ester | 103-93-5 |
| 4-(4-Methoxyphenyl)-2-butanone | 104-20-1 |
| Isobutyl benzoate | 120-50-3 |
| Benzene, 1,2-dimethoxy-4-(1-propenyl)- | 93-16-3 |
| beta-Phenylethylmethylethylcarbinol | 10415-87-9 |
| 1,1-Dimethoxy-2-phenylpropane | 90-87-9 |
| Geranyl formate | 105-86-2 |
| Bornyl formate | 7492-41-3 |
| 6-Octen-1-ol, 3,7-dimethyl-, formate | 105-85-1 |
| Benzeneacetic acid, butyl ester | 122-43-0 |
| 3,5,9-Undecatrien-2-one, 6,10-dimethyl- | 141-10-6 |
| Anisyl propionate | 7549-33-9 |
| Butanoic acid, 3-phenyl-2-propenyl ester | 103-61-7 |
| 2-Propenoic acid, 3-phenyl-, 2-methylpropyl ester | 122-67-8 |
| Eugenyl acetate | 93-28-7 |
| 3-Methylbutyl phenylacetate | 102-19-2 |
| Benzoic acid, 2-(methylamino)-, 2-methylpropyl ester | 65505-24-0 |
| Phenoxy ethyl isobutyrate | 103-60-6 |
| Anisyl butyrate | 6963-56-0 |
| 2,6-Octadien-1-ol, 3,7-dimethyl-, propanoate, (Z)- | 105-91-9 |
| Isobornyl propionate | 2756-56-1 |
| 1,3,5-Trithiane, 2,2,4,4,6,6-hexamethyl- | 828-26-2 |
| Geranyl N-butyrate | 106-29-6 |
| Geranyl isobutyrate | 2345-26-8 |
| Thiophene, 2,2'-dithiobis- | 6911-51-9 |
| 2-Propenoic acid, 3-phenyl-, cyclohexyl ester | 7779-17-1 |
| Benzeneacetic acid, 3-phenyl-2-propenyl ester | 7492-65-1 |
| Anisyl phenylacetate | 102-17-0 |
| 2-Propenoic acid, 3-phenyl-, 3-phenylpropyl ester | 122-68-9 |
| Geranyl phenylacetate | 102-22-7 |
| hexyl 2-methylbutyrate | 10032-15-2 |
| 4-heptanolide | 105-21-5 |
| Neral | 106-26-3 |
| (E)-2-octenol | 18409-17-1 |
| Ethyl 3-hydroxyhexanoate | 2305-25-1 |
| isopropyl hexanoate | 2311-46-8 |
| hexyl butanoate | 2639-63-6 |
| bis(2-methyl-3-furyl)disulfide | 28588-75-2 |
| 3-hydroxy-4,5-dimethyl-2(5H)-furanone | 28664-35-9 |
| 2-acetyl-2-thiazoline | 29926-41-8 |
| (E,E)-2,4-octadienal | 30361-28-5 |
| geranyl acetone | 3796-70-1 |
| 1-octen-3-one | 4312-99-6 |
| 3-mercapto-2-pentanone | 67633-97-0 |
| (Z)-3-hexenal | 6789-80-6 |
| 4-hexanolide | 695-06-7 |
| 5-octanolide | 698-76-0 |
| delta-decalactone | 705-86-2 |
| 4-vinylguaiacol | 7786-61-0 |
| Amyl salicylate | 2050-08-0 |
| Cyclohexyl formate | 4351-54-6 |

| Name | CAS # |
|---|---|
| Dimethylbenzylcarbinyl acetate | 151-05-3 |
| Geranyl propionate | 105-90-8 |
| Terpinyl acetate | 80-26-2 |
| isopropyl 3-methylbutanoate | 32665-23-9 |
| isopropyl 2-methylbutanoate | 66576-71-4 |
| 3-Hexenyl 3-methylbutanoate | 10032-11-8 |
| Isoamyl 2-methylbutyrate | 27625-35-0 |
| 3-Octyl acetate | 4864-61-3 |
| Benzyl isobutyrate | 103-28-6 |
| Cis-3-hexenyl butyrate | 16491-36-4 |
| Cis-3-hexenyl lactate | 61931-81-5 |
| Citronellyl butyrate | 141-16-2 |
| Citronellyl propionate | 141-14-0 |
| Isoamyl hexanoate | 2198-61-0 |
| 1,3,5-Undecatriene | 16356-11-9 |
| 1-Benzyloxy-2-methoxy-4-propenyl benzene | 120-11-6 |
| 1-Octen-3-yl acetate | 198242 |
| 2-Acetyl-3-ethyl pyrazine | 32974-92-8 |
| 2-Isopropyl-4-methyl thiazole | 15679-13-7 |
| 2-Methyl-2-pentenoic acid | 3142-72-1 |
| 2-sec-butyl thiazole | 18277-27-5 |
| 4,5-Dimethyl thiazole | 3581-91-7 |
| 4-(2,6,6-Trimethyl-2-cyclohexen-1-yl)butan-2-one | 31499-72-6 |
| 4-(2,6,6-Trimethyl cyclohexa-1,3-dienyl)but-2-en-4-one | 23696-85-7 |
| Acetaldehyde phenethyl propyl acetal | 7493-57-4 |
| Acetaldehyde ethyl cis-3-hexenyl acetal | 28069-74-1 |
| Acetone propylene glycol acetal | 1193-11-9 |
| Acetyl isoeugenol | 93-29-8 |
| 2-Acetyl-5-methyl furan | 1193-79-9 |
| Allyl cyclohexylbutyrate | 7493-65-4 |
| Alpha,alpha-dimethylphenethyl butyrate | 10094-34-5 |
| Alpha,alpha-dimethyl phenethyl formate | 10058-43-2 |
| Alpha,beta-santalol | 11031-45-1 |
| Alpha-amyl cinnamaldehyde dimethyl acetal | 91-87-2 |
| Alpha-fenchyl acetate | 13851-11-1 |
| Alpha-furfuryl pentanoate | 36701-01-6 |
| Alpha-ionol | 25312-34-9 |
| 6-Methyl-alpha-ionone | 79-69-6 |
| Alpha-methyl-p-isopropylphenylpropanaldehyde | 103-95-7 |
| Alpha-n-amyl-beta-phenylacryl acetate | 7493-78-9 |
| Alpha-piperitone | 6091-50-5 |
| Alpha-n-amyl-beta-phenyl acryl isovalerate | 7493-80-3 |
| 6-Amyl-alpha-pyrone | 27593-23-3 |
| Anisyl formate | 122-91-8 |
| Benzylcarbinyl 2-methyl butyrate | 24817-51-4 |
| Benzylcarbinyl 3-phenyl propenoate | 103-53-7 |
| Benzylcarbinyl alpha-toluate | 102-20-5 |
| Benzylcarbinyl butyrate | 103-52-6 |
| Benzylcarbinyl caproate | 6290-37-5 |
| Benzylcarbinyl formate | 104-62-1 |
| Benzylcarbinyl isobutyrate | 103-48-0 |
| Benzylcarbinyl salicylate | 87-22-9 |
| Benzylcarbinyl tiglate | 55719-85-2 |
| Benzyl dipropyl ketone | 7492-37-7 |
| Benzyl tiglate | 37526-88-8 |
| Beta-homocyclocitral | 472-66-2 |
| Beta-ionol | 22029-76-1 |
| 3-Phenylpropyl propanoate | 122-74-7 |
| Bois de rose oxide | 7392-19-0 |
| Butyl 2-methyl butyrate | 15706-73-7 |
| Butyl cinnamate | 538-65-8 |
| ortho-sec-Butyl cyclohexanone | 14765-30-1 |
| isobutyl cis-2-methyl-2-butenoate | 7779-81-9 |
| 5-n-Butyl-delta-valerolactone | 3301-94-8 |
| Campholenic aldehyde | 4501-58-0 |
| Cedran-8-yl acetate | 77-54-3 |
| Cinnamyl isovalerate | 140-27-2 |
| Cis-3-hexenyl benzoate | 25152-85-6 |
| Cis-3-hexenyl caproate | 31501-11-8 |
| Cis-3-hexenyl formate | 33467-73-1 |
| Cis-3-hexenyl isobutyrate | 41519-23-7 |
| Cis-3-hexenyl phenylacetate | 42436-07-7 |
| Cis-3-hexenyl propionate | 33467-74-2 |
| Cis-3-hexenyl tiglate | 67883-79-8 |
| Cis-3-hexenyl valerate | 35852-46-1 |
| cis-4-Hepten-1-ol | 6191-71-5 |
| Cis-5-octen-1-ol | 64275-73-6 |
| Citral dimethyl acetal | 7549-37-3 |
| Citronellyl isobutyrate | 97-89-2 |
| Citronellyl isovalerate | 68922-10-1 |
| Citronellyl valerate | 7540-53-6 |
| Citroxide | 7416-35-5 |
| Cocal | 21834-92-4 |
| p-Cresyl alpha-toluate | 101-94-0 |
| p-Cresyl isovalerate | 55066-56-3 |
| Dehydro-beta-cyclocitral | 116-26-7 |
| 8,8-Diethoxy-2,6-dimethyl-2-octanol | 7779-94-4 |
| 5,7-Dihydro-2-methyl thieno(3,4-d)pyrimidine | 36267-71-7 |
| 2,5-Dihydro-4,5-dimethyl-2-(2-methyl propyl)thiazole | 65894-83-9 |
| Dihydrojasmone | 1128-08-1 |
| Dihydroxyacetophenone | 28631-86-9 |
| 1,1-Dimethoxy-3,7-dimethyl-7-octanol | 141-92-4 |
| 3,7-Dimethyl-1,6-octadien-3-yl benzoate | 126-64-7 |
| 3,7-Dimethyl-1,6-octadien-3-yl butyrate | 78-36-4 |
| 3,7-Dimethyl-1,6-octadien-3-yl isobutyrate | 78-35-3 |
| 3,7-Dimethyl-1,6-octadien-3-yl propanoate | 144-39-8 |
| cis-3,7-Dimethyl-2,6-octadien-1-yl 2-methyl propanoate | 2345-24-6 |
| 2,4-Dimethyl-3-cyclohexene-1-carboxaldehyde | 68039-49-6 |
| 2,6-Dimethyl-5-hepten-1-al | 106-72-9 |
| trans,cis-2,6-Dodecadien-1-al | 21662-13-5 |
| Eglantal | 26643-91-4 |
| Ethyl E-2-hexenoate | 27829-72-7 |
| Ethyl tiglate | 5837-78-5 |
| Ethyl trans-4-decenoate | 76649-16-6 |
| 5-Ethyl-4-hydroxy-2-methyl-3[2H]furanone | 27538-09-6 |
| 2-Ethyl-4-methyl thiazole | 15679-12-6 |
| 2,6,10-Trimethyl-2,6,10-pentadecatrien-14-one | 762-29-8 |
| Guaiacyl phenyl acetate | 4112-89-4 |
| 3-Hepten-2-one | 1119-44-4 |
| trans-2-Hexen-1-ol | 2305-21-7 |
| Trans-2-hexenyl butyrate | 53398-83-7 |
| Hexyl phenylacetate | 5421-17-0 |
| Hexyl propionate | 2445-76-3 |
| Hydroxycitronellol | 107-74-4 |
| Isobutyl 2-butenoate | 589-66-2 |
| Isobutyl salicylate | 87-19-4 |
| Isodihydro lavandulal | 35158-25-9 |
| Isoeugenyl phenyl acetate | 120-24-1 |
| Isopropyl alpha-methylcrotonate | 1733-25-1 |
| p-Menth-1-en-8-yl propionate | 80-27-3 |
| Menthalactone | 13341-72-5 |
| 3-Methoxy-p-cymene | 1076-56-8 |
| Methyl 4-methyl pentanoate | 2412-80-8 |
| alpha-Methyl benzyl formate | 7775-38-4 |
| 2-Methylbutyl 2-methylbutanoate | 2445-78-5 |
| Methyl e-2-octenoate | 2396-85-2 |
| p-Methyl hydratropaldehyde | 99-72-9 |

| Name | CAS # |
|---|---|
| 3-(5-Methyl-2-furyl)butanal | 31704-80-0 |
| Nerol oxide | 1786-08-9 |
| trans,cis-2,6-Nonadien-1-ol | 7786-44-9 |
| trans-2-Octen-1-yl acetate | 3913-80-2 |
| 3-Octen-2-one | 1669-44-9 |
| 2-Phenyl-2-butenal | 4411-89-6 |
| 2-Propionylthiazole | 43039-98-1 |
| 1-Hydroxy-2-butanone | 5077-67-8 |
| 2-Butanone, 3-hydroxy-, (+−)- | 52217-02-4 |
| Thiazole, 2,5-dimethyl- | 4175-66-0 |
| Butanethioic acid, S-methyl ester | 2432-51-1 |
| 2,4-Hexadienoic acid, methyl ester, (E,E)- | 689-89-4 |
| Benzeneacetaldehyde, 4-methyl- | 104-09-6 |
| Bicyclo[4.1.0]hept-3-ene, 3,7,7-trimethyl-, (1S)- | 498-15-7 |
| Ethyl 3-hexenoate | 2396-83-0 |
| 1H-Pyrrole, 1-(2-furanylmethyl)- | 1438-94-4 |
| 6-Octenal, 3,7-dimethyl-, (R)- | 2385-77-5 |
| Ethanethioic acid, S-(2-furanylmethyl) ester | 13678-68-7 |
| 6-Octen-1-ol, 3,7-dimethyl-, (R)- | 1117-61-9 |
| 6-Octen-1-ol, 3,7-dimethyl-, (S)- | 7540-51-4 |
| DL-Tetrahydrofurfuryl propionate | 637-65-0 |
| Benzenepentanol | 10521-91-2 |
| Cyclohexaneethanol, acetate | 21722-83-8 |
| Benzyl isobutyl ketone | 5349-62-2 |
| Butanoic acid, 3-oxo-, phenylmethyl ester | 5396-89-4 |
| 1,2-Ethanediamine, N,N'-bis(phenylmethyl)- | 140-28-3 |
| 2-Ethyl-3-hydroxy-4-pyrone | 1110651 |
| Dicyclohexyl disulfide | 2550-40-5 |
| Tetrahydrofurfuryl butyrate | 2217-33-6 |
| Thujone | 546-80-5 |
| Benzyl alcohol, alpha-methyl-, butyrate | 3460-44-4 |
| Citronellyl tiglate | 24717-85-9 |
| Lactitol | 585-86-4 |
| Nonivamide | 2444-46-4 |
| 2-Acetoxy-3-butanone | 4906-24-5 |
| 3-Acetyl-2,5-dimethylthiophene | 230378 |
| 3-Acetyl-2-5dimethylfuran | 10599-70-9 |
| 4-Acetyl-6-t-butyl-1,1-dimethylindan | 13171-00-1 |
| Allyl 2-furoate | 4208-49-5 |
| Allyl sorbate | 7493-75-6 |
| Allyl thiopropionate | 41820-22-8 |
| Allyl tiglate | 7493-71-2 |
| Amylcyclohexyl acetate | 67874-72-0 |
| Benzaldehyde glyceryl acetal | 1319-88-6 |
| Benzaldehyde propylene glycol acetal | 2568-25-4 |
| Bornyl isovalerate | 76-50-6 |
| 1,3-Butanedithiol | 24330-52-7 |
| 2,3-Butanedithiol | 4532-64-3 |
| Butyl cinnamic aldehyde | 7492-44-6 |
| Cinnamyl benzoate | 5320-75-2 |
| Citral ethylene glycol acetal | 66408-78-4 |
| Citronellyloxyacetaldehyde | 7492-67-3 |
| Citronellyl phenylacetate | 139-70-8 |
| Cyclohexyl isovalerate | 7774-44-9 |
| Decalactone | 5579-78-2 |
| 2,5-Dimethyl-4-methoxy-3(2H)-furanone | 4077-47-8 |
| 6,10-Dimethyl-9-undecen-2-one | 4433-36-7 |
| 2-Ethoxythiazole | 15679-19-3 |
| Ethyl 2-mercaptopropionate | 19788-49-9 |
| Ethyl 2-methyl-4-pentenoate | 53399-81-8 |
| Ethyl 3-(2-furyl)propanoate | 94278-27-0 |
| Ethyl cyclohexanepropionate | 10094-36-7 |
| Ethyl (p-tolyloxy)acetate | 67028-40-4 |
| 3-Ethyl-2-hydroxy-2-cyclopenten-1-one | 21835-01-8 |
| Ethylene brassylate | 105-95-3 |
| 2-Ethylfenchol | 18368-91-7 |
| Furfuryl 3-methylbutanoate | 13678-60-9 |
| Furfuryl butyrate | 623-21-2 |
| Furfuryl isopropyl sulfide | 1883-78-9 |
| Furfuryl methyl sulfide | 1438-91-1 |
| Furfuryl propionate | 623-19-8 |
| Furfuryl thiopropionate | 59020-85-8 |
| Geranyl acetoacetate | 10032-00-5 |
| Geranyl benzoate | 94-48-4 |
| Geranyl isovalerate | 109-20-6 |
| delta-Hexalactone | 823-22-3 |
| trans-3-Hexenal | 69112-21-6 |
| cis-3-Hexenyl anthranilate | 65405-76-7 |
| trans-2-Hexenyl propionate | 53398-80-4 |
| 5-(cis-3-Hexenyl) dihydro-5-methyl-2(3H)furanone | 70851-61-5 |
| Hexyl 2-formate | 39251-86-0 |
| Hexyl crotonate | 19089-92-0 |
| Hexyl formate | 629-33-4 |
| Isoamyl 3-(2-furyl)propionate | 7779-67-1 |
| Isoamyl pyruvate | 7779-72-8 |
| Isobutyl furylpropionate | 105-01-1 |
| Isohexenyl cyclohexenyl carboxaldehyde | 37677-14-8 |
| p-Isopropyl phenylacetaldehyde | 4395-92-0 |
| Linalyl cinnamate | 78-37-5 |
| Linalyl formate | 115-99-1 |
| Linalyl isovalerate | 1118-27-0 |
| Linalyl phenylacetate | 7143-69-3 |
| Maltol isobutyrate | 65416-14-0 |
| Methyl 2-methylpentanoate | 2177-77-7 |
| Methyl 3-hydroxyhexanoate | 21188-58-9 |
| Methyl 3-nonenoate | 13481-87-3 |
| Methyl furfuryl disulfide | 57500-00-2 |
| Methyl p-tert-butylphenylacetate | 3549-23-3 |
| 3-Methyl-1,2-cyclohexanedione | 3008-43-3 |
| alpha-Methylanisalacetone | 104-27-8 |
| 2-Methylbutyl isovalerate | 2445-77-4 |
| 4-Methylnonanoic acid | 45019-28-1 |
| 4-Methyloctanoic acid | 54947-74-9 |
| 2-Methyltetrahydrothiophen-3-one | 13679-85-1 |
| 3-(Methylthio)butanal | 16630-52-7 |
| 4-(Methylthio)butanol | 20582-85-8 |
| 4-Methylthio-2-butanone | 34047-39-7 |
| 4-Methylthio-4-methyl-2-pentanone | 23550-40-5 |
| Neryl butyrate | 999-40-6 |
| Neryl formate | 2142-94-1 |
| Neryl isovalerate | 3915-83-1 |
| Octahydrocoumarin | 4430-31-3 |
| Phenethyl 2-furoate | 7149-32-8 |
| 1-Phenyl-2-pentanol | 705-73-7 |
| Phenylacetaldehyde diisobutylacetal | 68345-22-2 |
| Phenylacetaldehyde glyceryl acetal | 29895-73-6 |
| 2-(3-Phenylpropyl)pyridine | 2110-18-1 |
| Propyl phenylacetate | 4606-15-9 |
| Pyrazineethanethiol | 35250-53-4 |
| Ethyl 2-methyl pentanoate | 39255-32-8 |
| Methyl 2,4-decadienoate | 4493-42-9 |
| alpha-Isomethyl ionone | 127-51-5 |
| 5-Methyl hexanoic acid | 628-46-6 |
| Ethyl 3-methyl pentanoate | 5870-68-8 |
| Ethyl 2-methyl-3,4-pentadienoate | 60523-21-9 |
| 3-Nonen-2-one | 14309-57-0 |
| 5-Methyl-3-hexen-2-one | 5166-53-0 |
| Maltol propionate | 68555-63-5 |
| 2-Methyl-3-(2-furyl) acrolein | 874-66-8 |
| Ethyl 3(2-furyl)propanoate | 10031-90-0 |
| 2-Phenyl-3-(2-furyl)-propenal | 57568-60-2 |

| Name | CAS # |
| --- | --- |
| 4-Methyl-2-pentyl-1,3-dioxolane | 1599-49-1 |
| 2-Ethyl-4,5-dimethyl oxazole | 53833-30-0 |
| Isobornyl isovalerate | 7779-73-9 |
| Theophylline-7-acetic acid | 652-37-9 |
| Ethyl trans-2-octenoate | 7367-82-0 |
| DL-Arginine | 7200-25-1 |
| Allyl Crotonate | 20474-93-5 |
| 2-Methoxystyrene | 612-15-7 |
| Magnesium Fumarate | 7704-71-4 |
| 2-Propionylpyrrole | 1073-26-3 |
| 2-methyl-1,3-dithiolane | 5616-51-3 |
| 2-ethyl-5-methyl pyrazine | 13360-64-0 |
| 2-methyl-3-(dimercaptomethyl)-furan | 65505-17-1 |
| Magnesium gluconate | 3632-91-5 |
| Manganese gluconate | 6485-39-8 |
| Erythritol | 149-32-6 |
| D-Arabinose | 28697-53-2 |
| D-Galactose | 59-23-4 |
| D-(+)-Mannose | 3458-28-4 |
| Sorbitol | 50-70-4 |
| Aspartame | 22839-47-0 |
| Cyclamic Acid | 100-88-9 |
| Dulcin | 150-69-6 |
| Glucose-1-phosphate Dipotassium Salt | 29732-59-0 |
| L-(+)-Arabinose | 87-72-9 |
| Fructose-6-Phosphate | 643-13-0 |
| D-Maltose Monohydrate | 6363-53-7 |
| Ribose | 24259-59-4 |
| Fructose 1,6-Diphosphate Disodium Salt | 26177-85-5 |
| Saccharin sodium, dihydrate | 6155-57-3 |
| 1,2-Benzisothiazol-3(2H)-one 1,1-dioxide, calcium salt | 6485-34-3 |
| 1,2-Benzisothiazolin-3-one 1,1 dioxide, potassium salt | 10332-51-1 |
| zeranol | 26538-44-3 |
| beta-D-fructopyranose | 7660-25-5 |
| D-fructose 1,6-bisphosphate | 488-69-7 |
| Ribose 5-phosphate | 4300-28-1 |
| Arabinose | 147-81-9 |
| Saccharin, sodium salt hydrate | 82385-42-0 |
| Maltitol | 585-88-6 |
| D-Fructose 1-phosphate | 15978-08-2 |
| D-Sorbitol 6-phosphate | 108392-12- |
| alpha-D-Xylose | 31178-70-8 |
| Inositol 1-phosphate | 573-35-3 |

| Name | CAS # |
| --- | --- |
| Sodium Metabisulfite | 7681-57-4 |
| sodium hydrogen phosphate | 7558-79-4 |
| Sodium Phosphate Monobasic | 7558-80-7 |
| Sodium thiosulfate | 7772-98-71 |
| Orthoboric acid | 10043-35-3 |
| Diethanolamine | 111-42-2 |
| Benzaldehyde | 100-52-7 |
| Sorbic acid | 110-44-1 |
| L-(+)-Tartaric Acid | 87-69-4 |
| D-mannitol | 69-65-8 |
| Butyl paraben | 94-26-8 |
| Thymol | 89-83-8 |
| Methyl salicylate | 119-36-8 |
| Citric acid | 77-92-9 |
| Creatinine | 60-27-5 |
| Vitamin C | 50-81-7 |
| Benzoic Acid | 65-85-0 |
| Methyl 4-hydroxybenzoate | 99-76-3 |
| m-Cresol | 108-39-4 |
| p-Cresol | 106-44-5 |
| Aspirin | 50-78-2 |
| Phenol | 108-95-2 |
| Sucrose | 57-50-1 |
| Potassium citrate, monohydrate | 1534146 |
| Sodium acetate | 127-09-3 |
| Lactic acid | 50-21-5 |
| Propionic acid, sodium salt | 65-85 |
| Benzyl alcohol | 100-51-6 |
| Phenethyl alcohol | 60-12-8 |
| Cholesterol | 57-88-5 |
| D-Glucose | 50-99-7 |
| Sorbitol | 50-70-4 |
| Aspartame | 22839-47-0 |
| Saccharin | 81-07-2 |
| 2,6-Di-tert-Butyl-p-Cresol | 128-37-0 |
| 4-Chloro-3-methylphenol | 59-50-7 |
| glycerin | 56-81-5 |
| Propyl paraben | 94-13-3 |
| fumaric acid | 110-17-8 |
| dabco | 280-57-9 |
| p-Phenylenediamine | 106-50-3 |
| Anethole | 4180-23-8 |
| propyl gallate | 121-79-9 |
| L-monosodium glutamate | 142-47-2 |
| Butylated hydroxyanisole | 25013-16-5 |
| Cyclohexanol, 5-methyl-2-(1-methylethyl)-, (1alpha,2beta,5alpha)- | 89-78-1 |
| alpha-Thioglycerol | 96-27-5 |
| Sodium dehydroacetate | 4418-26-2 |
| Ethyl 4-hydroxybenzoate | 120-47-8 |
| Ethyl Vanillin | 121-32-4 |
| Triacetin | 102-76-1 |
| Potassium sorbate | 590-00-1 |
| Triethyl citrate | 77-93-0 |
| (S)-(+)-Arginine | 74-79-3 |
| Glycine | 56-40-6 |
| (S)-(−)-Histidine | 71-00-1 |
| (S)-(+)-Lysine | 56-87-1 |
| Quinone | 106-51-4 |
| Naphthalene, 2-ethoxy- | 93-18-5 |
| Methanesulfonic Acid | 75-75-2 |
| DL-Tartaric Acid | 133-37-9 |
| Cyclamic acid | 100-88-9 |
| (S)-(−)-Phenylalanine | 63-91-2 |
| (S)-(−)-Tyrosine | 60-18-4 |
| Carvone | 99-49-0 |
| Ethyl butyrate | 105-54-4 |
| 6-Methyl-5-hepten-2-one | 110-93-0 |
| Ethyl acetoacetate | 141-97-9 |
| Methyl benzoate | 93-58-3 |
| Phenylacetic Acid | 103-82-2 |
| Adipic acid | 124-04-9 |
| Ethyl benzoate | 93-89-0 |
| Benzyl benzoate | 120-51-4 |
| Pyruvic acid | 127-17-3 |
| Succinic acid | 110-15-6 |
| Indole | 120-72-9 |
| Methyl anthranilate | 134-20-3 |
| Diethyl malonate | 105-53-3 |
| Niacin | 59-67-6 |
| Meso-inositol | 87-89-8 |
| 4-Aminobenzoic acid | 150-13-0 |
| Anisole | 100-66-3 |
| Urea | 57-13-6 |
| Pyrrolidine | 123-75-1 |
| Cyclopentanone | 120-92-3 |
| Acetic anhydride | 108-24-7 |
| Benzophenone | 119-61-9 |
| D-(−)-Fructose | 57-48-7 |
| D-(+)-Xylose | 58-86-6 |
| o-Methoxybenzoic Acid | 579-75-9 |
| linalool | 78-70-6 |
| ethyl isovalerate | 108-64-5 |
| 1,1'-Azobisformamide | 123-77-3 |
| 6-Methylcoumarin | 92-48-8 |
| acetoin | 513-86-0 |
| alpha-Phellandrene | 99-83-2 |
| Cymene | 99-87-6 |

| Name | CAS # |
|---|---|
| Dimethyl Succinate | 106-65-0 |
| p-Anisaldehyde | 123-11-5 |
| Phenyl ether | 101-84-8 |
| Tetrahydro-2-furanmethanol | 97-99-4 |
| Valeric Acid | 109-52-4 |
| 3,4-xylenol | 95-65-8 |
| 1,1-diethoxyethane | 105-57-7 |
| ethyl butyraldehyde | 97-96-1 |
| Ethyl crotonate | 623-70-1 |
| ethyl isobutyrate | 97-62-1 |
| methyl isovalerate | 556-24-1 |
| methyl propionate | 554-12-1 |
| methyl valeraldehyde | 123-15-9 |
| 4-(2,6,6-Trimethyl-2-cyclohexen-1-yl)-3-buten-2-one | 127-41-3 |
| 4-(2,6,6-trimethyl-1-cyclohexen-1-yl)-3-buten-2-one | 14901-07-6 |
| Maleic acid | 110-16-7 |
| 3-Methylbutanoic acid | 503-74-2 |
| L-Glutamic Acid | 56-86-0 |
| D-limonene | 5989-27-5 |
| 1-Phenyl-1-propanol | 93-54-9 |
| 2'-Hydroxyacetophenone | 118-93-4 |
| 2,4-Dihydroxybenzoic Acid | 89-86-1 |
| 2-Phenyl-1-propanol | 1123-85-9 |
| 3-Phenylpropionic Acid | 501-52-0 |
| 4-Ethoxyphenol | 622-62-8 |
| Alpha-Terpineol | 98-55-5 |
| Benzaldehyde Dimethylacetal | 1125-88-8 |
| Benzyl Ether | 103-50-4 |
| Benzyl Formate | 104-57-4 |
| Benzyl Salicylate | 118-58-1 |
| Cinnamyl Alcohol | 104-54-1 |
| D-(+)-Glucono-1,5-lactone | 4253-68-3 |
| D-Isoascorbic Acid | 89-65-6 |
| 2,3-Naphthalenediol | 92-44-4 |
| Diethyl Succinate | 123-25-1 |
| Ethyl 2-Aminobenzoate | 87-25-2 |
| Ethyl Cinnamate | 103-36-6 |
| Ethyl Phenylacetate | 101-97-3 |
| Ethyl Salicylate | 118-61-6 |
| gamma-Valerolactone | 108-29-2 |
| Hydroquinone Dimethyl Ether | 150-78-7 |
| Isocaproic Acid | 646-07-1 |
| Isoeugenol | 97-54-1 |
| Isopropyl Benzoate | 939-48-0 |
| L-(+)-Isoleucine | 73-32-5 |
| L-Malic acid | 97-67-6 |
| L-2-Aminopropionic Acid | 56-41-7 |
| L-Carnitine | 541-15-1 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| Phenoxyacetic Acid | 122-59-8 |
| Veratrole | 91-16-7 |
| 2-Ethylbutyric acid | 88-09-5 |
| 2-Methylpyrazine | 109-08-0 |
| o-methoxybenzaldehyde | 135-02-4 |
| L-Leucine | 61-90-5 |
| L-Asparagine | 70-47-3 |
| propiophenone | 93-55-0 |
| 5-isopropyl-2-methyl-phenol | 499-75-2 |
| Xylitol | 87-99-0 |
| ethyl 4-oxopentanoate | 539-88-8 |
| methyl cinnamate | 103-26-4 |
| cumic alcohol | 536-60-7 |
| methyl 2-naphthyl ketone | 93-08-3 |
| 1-methyl-4-(1-methylethyl)-1,4-Cyclohexadiene | 99-85-4 |
| en-ethylene diamine | |
| Caffeine | 58-08-2 |
| 5-methylfurfural | 620-02-0 |
| furfuryl acetate | 623-17-6 |
| terpinen-4-ol | 10482-56-1 |
| phenylethanal | 122-78-1 |
| 4'-Methoxyacetophenone | 100-06-1 |
| D-Fenchone | 4695-62-9 |
| 1-Methoxy-4-methylbenzene | 104-93-8 |
| o-methylanisole | 578-58-5 |
| Acetylacetaldehyde dimethyl acetal | 5436-21-5 |
| p-methylacetophenone | 122-00-9 |
| Methyl phenylacetate | 101-41-7 |
| 4-Ethoxybenzaldehyde | 10031-82-0 |
| p-tolyl acetate | 140-39-6 |
| 2,6-Dimethoxyphenol | 91-10-1 |
| Methyl 2-methoxybenzoate | 606-45-1 |
| alpha-methylcinnamaldehyde | 101-39-3 |
| 2-methoxycinnamaldehyde | 60125-24-8 |
| Potassium bicarbonate | 298-14-6 |
| piperonyl acetate | 326-61-4 |
| 2,3-hexanedione | 3848-24-6 |
| furfural acetone | 623-15-4 |
| trans beta-(2-furyl)acrolein | 623-30-3 |
| carveol | 99-48-9 |
| Methyl nicotinate | 93-60-7 |
| Ethyl benzoylacetate | 94-02-0 |
| Methyl 4-methoxybenzoate | 121-98-2 |
| Levulinic acid | 123-76-2 |
| m-Dimethoxybenzene | 151-10-0 |
| 2-acetylpyridine | 1122-62-9 |
| tetramethyl-pyrazine | 1124-11-4 |
| 2,3-dimethyl-pyrazine | 5910-89-4 |
| trimethyl-pyrazine | 14667-55-1 |
| 2-ethyl-3-methyl-pyrazine | 15707-23-0 |
| 5-Methyl-3H-furan-2-one | 591-12-8 |
| 2-Methoxy-4-methylphenol | 93-51-6 |
| piperazine | 110-85-0 |
| 2-Methoxy-4-propylphenol | 2785-87-7 |
| Naphthalene, 2-(2-methylpropoxy)- | 2173-57-1 |
| 2-Acetyl-1-methylpyrrole | 932-16-1 |
| 3,3-Dimethylacrylic acid | 541-47-9 |
| Ethyl sorbate | 2396-84-1 |
| 4-(4-Hydroxyphenyl)-2-butanone | 5471-51-2 |
| 4-Methoxyphenylacetone | 122-84-9 |
| (−)-Myrtenal | 564-94-3 |
| 3-Phenylpropionaldehyde | 104-53-0 |
| 1-Phenylethyl propionate | 120-45-6 |
| 2-Methyltetrahydrofuran-3-one | 3188-00-9 |
| Cinnamyl acetate | 103-54-8 |
| Styrallyl acetate | 93-92-5 |
| Ethyl 4-methoxybenzoate | 94-30-4 |
| Benzyl propionate | 122-63-4 |
| Phenylpyruvate | 156-06-9 |
| furaneol | 3658-77-3 |
| methyl 2-methylbutanoate | 868-57-5 |
| Benzeneacetaldehyde, alpha-methyl- | 93-53-8 |
| Dimethyl anthranilate | 85-91-6 |
| 1,1-Dimethoxy-2-phenylpropane | 90-87-9 |
| 4-hexanolide | 695-06-7 |
| Dimethylbenzylcarbinyl acetate | 151-05-3 |
| Benzyl isobutyrate | 103-28-6 |
| Acetyl isoeugenol | 93-29-8 |
| 2-Acetyl-5-methyl furan | 1193-79-9 |
| Alpha-methyl-p-isopropylphenylpropanaldehyde | 103-95-7 |
| Benzylcarbinyl formate | 104-62-1 |
| p-Cresyl alpha-toluate | 101-94-0 |
| Potassium bisulfate | 7646-93-7 |
| Potassium carbonate | 584-08-7 |
| Potassium chloride | 7447-40-7 |
| Potassium hydroxide | 1310-58-3 |
| Ethyl tiglate | 5837-78-5 |
| Nerol oxide | 1786-08-9 |
| DL-Tetrahydrofurfuryl propionate | 637-65-0 |
| Benzaldehyde propylene glycol acetal | 2568-25-4 |
| 2-Methyl-3-(2-furyl) acrolein | 874-66-8 |
| vanillin | 121-33-5 |
| Cholic acid | 81-25-4 |

-continued

| Name | CAS # |
| --- | --- |
| R-Carvone | 6485-40-1 |
| Potassium nitrate | 7757-79-1 |
| Potassium permanganate | 7722-64-7 |
| Potassium persulfate | 7727-21-1 |
| Potassium phosphate, dibasic | 2139900 |
| Potassium Phosphate Monobasic | 7778-77-0 |
| Potassium sulfate | 7778-80-5 |
| Sodium bicarbonate | 144-55-8 |
| Sodium bisulfite | 7631-90-5 |
| Sodium carbonate | 497-19-8 |
| Sodium chloride | 7647-14-5 |
| Sodium dithionite | 7775-14-6 |
| Sodium hydroxide | 1310-73-2 |
| Sodium nitrite | 7632-00-0 |
| Sodium Pyrophosphate | 7722-88-5 |
| Sodium sulfate | 7757-82-6 |
| Sodium sulfite | 7757-83-7 |
| Sodium thiocyanate | 540-72-7 |
| Calcium Carbonate | 471-34-1 |
| Calcium chloride | 10043-52-4 |
| Calcium gluconate | 299-28-5 |
| Calcium hydroxide | 1305-62-0 |
| Calcium phosphate, dibasic | 7757-93-9 |
| Calcium sulfate | 7778-18-9 |
| N-Methyl-D-glucamine | 6284-40-8 |
| Calcium oxide | 1305-78-8 |
| Calcium Phosphate Monobasic | 7758-23-8 |
| Magnesium chloride hexahydrate | 7791-18-6 |
| Magnesium sulfate | 7487-88-9 |
| Magnesium Sulfate Heptahydrate | 10034-99-8 |
| Aluminum chloride hexahydrate | 7784-13-6 |
| aluminum nitrate nonahydrate | 7784-27-2 |
| Aluminum potassium sulfate, dodecahydrate | 7784-24-9 |
| Aluminum sulfate, octadecahydrate | 7784-31-8 |
| (S)-(−)-Cysteine | 52-90-4 |
| p-Toluenesulfonic Acid | 104-15-4 |
| Potassium bitartrate | 868-14-4 |
| DL-aspartic acid | 617-45-8 |
| p-Dimethylaminobenzaldehyde | 100-10-7 |
| Sodium salicylate | 54-21-7 |
| Benzoin | 119-53-9 |
| Sodium dodecyl sulfate | 151-21-3 |
| L-Menthol | 2216-51-5 |
| Tiron | 149-45-1 |
| Riboflavin | 83-88-5 |
| Sodium Acetate Trihydrate | 6131-90-4 |
| Disodium Succinate Hexahydrate | 6106-21-4 |
| Disodium ethylenediaminetetraacetate dihydrate | 6381-92-6 |
| sodium citrate, dihydrate | 1545801 |
| Sodium potassium tartrate, tetrahydrate | 6381-59-5 |
| L-(+)-Arginine monohydrochloride | 1119-34-2 |
| Ethylenediamine dihydrochloride | 333-18-6 |
| Sodium formate | 141-53-7 |
| Sodium acetate | 127-09-3 |
| Potassium acetate | 127-08-2 |
| Ammonium citrate | 3012-65-5 |
| Ammonium bicarbonate | 1066-33-7 |
| Ammonium chloride | 12125-02-9 |
| Ammonium nitrate | 6484-52-2 |
| Ammonium persulfate | 7727-54-0 |
| Ammonium sulfate | 7783-20-2 |
| Zinc chloride | 7646-85-7 |
| Sulfuric acid, zinc salt (1:1), heptahydrate | 7446-20-0 |
| Sodium Tripolyphosphate | 7758-29-4 |
| ammonium benzoate | 1863-63-4 |
| ammonium bisulfite | 10192-30-0 |
| 1,5-Naphthalenedisulfonic Acid Disodium Salt | 1655-29-4 |
| 4-Hydroxybenzoic Acid | 99-96-7 |
| Diphenylacetic Acid | 117-34-0 |
| Glutaric Acid | 110-94-1 |
| L-(−)-Fucose | 2438-80-4 |
| L-Cysteine Hydrochloride | 52-89-1 |
| L-Histidine Hydrochloride Monohydrate | 1880304 |
| o-Toluic Acid | 118-90-1 |
| Pivalic Acid | 75-98-9 |
| Pyruvic Acid Sodium Salt | 113-24-6 |
| Potassium bromide | 2139626 |
| Sodium Dithionate Dihydrate | 7631-94-9 |
| Sodium Malonate | 141-95-7 |
| Trisodium Citrate | 68-04-2 |
| Potassium Sodium Tartrate | 304-59-6 |
| Potassium Citrate | 866-84-2 |
| D-Maltose Monohydrate | 6363-53-7 |
| Cyclohexaamylose | 10016-20-3 |
| Dodecyl sulfate, lithium salt | 2044-56-6 |
| Manganese chloride | 2145076 |
| methyl-urea | 598-50-5 |
| beta-Cyclodextrin | 7585-39-9 |
| Triphosphoric acid, pentapotassium salt | 13845-36-8 |
| Glycine ethyl ester hydrochloride | 623-33-6 |
| L-Histidine methyl ester dihydrochloride | 7389-87-9 |
| L-Leucine methyl ester hydrochloride | 7517-19-3 |
| D-Lysine hydrochloride | 7274-88-6 |
| 2-Naphthalenesulfonic acid sodium salt | 532-02-5 |
| calcium nitrate tetrahydrate | 13477-34-4 |
| Vitamin B1 | 59-43-8 |
| Zinc Acetate Dihydrate | 5970-45-6 |
| Potassium fluoride | 7789-23-3 |
| Potassium iodate | 2139718 |
| Potassium iodide | 7681-11-0 |
| Potassium thiocyanate | 333-20-0 |
| Sodium bromide | 7647-15-6 |
| Sodium fluoride | 7681-49-4 |
| Sodium iodide | 7681-82-5 |
| Sodium nitrate | 7631-99-4 |
| Calcium acetate | 5743-26-0 |
| Trichloroacetic acid | 76-03-9 |
| Ammonium acetate | 631-61-8 |
| Ammonium fluoride | 12125-01-8 |
| DL-malic acid | 617-48-1 |
| t-Butyl Alcohol | 75-65-0 |
| beta-Alanine | 107-95-9 |
| (S)-(−)-Tryptophan | 73-22-3 |
| Malonic acid | 141-82-2 |
| Phenethylamine | 64-04-0 |
| Salicylylaldehyde | 90-02-8 |
| Sodium benzoate | 532-32-1 |
| Mandelic acid | 90-64-2 |
| Calcium pantothenate | 137-08-6 |
| Chloroacetic Acid | 79-11-8 |
| Ethanol Amine | 141-43-5 |
| Salicylic acid | 69-72-7 |
| Saccharin sodium | 128-44-9 |
| Thiamine hydrochloride | 67-03-8 |
| 2,2'-Oxybisethanol | 111-46-6 |
| Resorcinol | 108-46-3 |
| 2-Amino-2-(hydroxymethyl)-1,3-propanediol | 77-86-1 |
| 2,5-Dimethylphenol | 95-87-4 |
| Ammonium Phosphate Monobasic | 7722-76-1 |
| 1,3-Butanediol | 107-88-0 |
| Glycolic Acid | 79-14-1 |
| Sodium Gluconate | 527-07-1 |
| Terephthalic Acid | 100-21-0 |
| L-Ascorbic Acid Sodium Salt | 134-03-2 |
| 3-Acetyl-6-methyl-2,4-pyrandione | 520-45-6 |
| Calcium Acetate | 62-54-4 |
| Nicotinamide | 98-92-0 |
| 1-Hydroxy-2-naphthoic Acid | 86-48-6 |
| 2-Isopropylphenol | 88-69-7 |

| Name | CAS # |
|---|---|
| 4-Aminosalicylic Acid | 65-49-6 |
| Calcium Glycerophosphate | 27214-00-2 |
| Erythorbic Acid Sodium Salt | 7378-23-6 |
| Gluconic Acid Potassium Salt | 299-27-4 |
| Orotic Acid | 65-86-1 |
| p-Anise Alcohol | 105-13-5 |
| Potassium Benzoate | 582-25-2 |
| Taurine | 107-35-7 |
| Thiamine Nitrate | 532-43-4 |
| 3,3,5-Trimethyl-1-cyclohexanol | 116-02-9 |
| tert-Butylhydroquinone | 1948-33-0 |
| Sulfosalicylic acid | 97-05-2 |
| Gallic acid | 149-91-7 |
| L-borneol | 464-45-9 |
| Isoborneol | 124-76-5 |
| 2,5-Dihydroxybenzoic acid, Gentisic acid | 490-79-9 |
| 5-hydroxy-6-methyl-3,4-pyridinedimethanol | 65-23-6 |
| Naphthalene-2-sulfonic acid | 120-18-3 |
| Ethanesulfonic acid, 2-hydroxy-, monosodium salt | 1562-00-1 |
| Pamoic acid | 130-85-8 |
| 2,4-Dimethylphenol | 105-67-9 |
| 3,5-Dihydroxyacetophenone | 51863-60-6 |
| Eugenol | 97-53-0 |
| n-Butyric Acid | 107-92-6 |
| Hydroquinone | 123-31-9 |
| Propionic Acid | 79-09-4 |
| meta-Phenylenediamine | 108-45-2 |
| Oxalic Acid | 144-62-7 |
| n-Hexanoic Acid | 142-62-1 |
| 2-Furancarboxylic Acid | 88-14-2 |
| 4'-Nitroacetanilide | 104-04-1 |
| D-(−)-Tartaric Acid | 147-71-7 |
| p-Acetamidobenzoic Acid | 556-08-1 |
| Galactaric acid | 526-99-8 |
| D-glucuronate | 1700908 |
| Lactobionic acid | 96-82-2 |
| p-Formylacetanilide | 122-85-0 |
| 2-Mercaptobenzoic acid | 147-93-3 |
| Propanoic acid, 2-hydroxy-, calcium salt (2:1), (S)- | 28305-25-1 |
| D(+)-10-Camphorsulfonic acid | 3144-16-9 |
| 3-Cyclopentylpropionic acid | 140-77-2 |
| 1R-(−)-Camphorsulfonic acid | 35963-20-3 |
| DL-Lysine | 70-54-2 |
| Cinnamic acid | 621-82-9 |
| Triethanolamine | 102-71-6 |
| Acetic Acid | 64-19-7 |
| Dichloroacetic Acid | 79-43-6 |
| Diethylamine | 109-89-7 |
| Diethylaminoethanol | 100-37-8 |
| N-(2-Hydroxyethyl)Morpholine | 622-40-2 |
| Octanoic Acid | 124-07-2 |
| isobutyric acid | 79-31-2 |
| Anisic Acid | 100-09-4 |
| Betaine | 107-43-7 |
| Enanthoic Acid | 111-14-8 |
| Hippuric Acid | 495-69-2 |
| Tiglic Acid | 80-59-1 |
| Cyclohexanecarboxylic acid | 98-89-5 |
| m-Methoxybenzoic acid | 586-38-9 |
| D-(+)-Camphoric acid | 124-83-4 |
| N-(2-Hydroxyethyl)pyrrolidine | 2955-88-6 |
| Sodium Metabisulfite | 7681-57-4 |
| sodium hydrogen phosphate | 7558-79-4 |
| Sodium Phosphate Monobasic | 7558-80-7 |
| Sodium thiosulfate | 7772-98-71 |
| Orthoboric acid | 10043-35-3 |
| Diethanolamine | 111-42-2 |
| Benzaldehyde | 100-52-7 |
| Sorbic acid | 110-44-1 |
| L-(+)-Tartaric Acid | 87-69-4 |
| D-mannitol | 69-65-8 |
| Butyl paraben | 94-26-8 |
| Thymol | 89-83-8 |
| Methyl salicylate | 119-36-8 |
| Citric acid | 77-92-9 |
| Creatinine | 60-27-5 |
| Vitamin C | 50-81-7 |
| Benzoic Acid | 65-85-0 |
| Methyl 4-hydroxybenzoate | 99-76-3 |
| m-Cresol | 108-39-4 |
| p-Cresol | 106-44-5 |
| Aspirin | 50-78-2 |
| Phenol | 108-95-2 |
| Sucrose | 57-50-1 |
| Potassium citrate, monohydrate | 1534146 |
| Sodium acetate | 127-09-3 |
| Lactic acid | 50-21-5 |
| Propionic acid, sodium salt | 65-85 |
| Benzyl alcohol | 100-51-6 |
| Phenethyl alcohol | 60-12-8 |
| Cholesterol | 57-88-5 |
| D-Glucose | 50-99-7 |
| Sorbitol | 50-70-4 |
| Aspartame | 22839-47-0 |
| Saccharin | 81-07-2 |
| 2,6-Di-tert-Butyl-p-Cresol | 128-37-0 |
| 4-Chloro-3-methylphenol | 59-50-7 |
| glycerin | 56-81-5 |
| Propyl paraben | 94-13-3 |
| fumaric acid | 110-17-8 |
| dabco | 280-57-9 |
| p-Phenylenediamine | 106-50-3 |
| Anethole | 4180-23-8 |
| propyl gallate | 121-79-9 |
| L-monosodium glutamate | 142-47-2 |
| Butylated hydroxyanisole | 25013-16-5 |
| Cyclohexanol, 5-methyl-2-(1-methylethyl)-, (1alpha,2beta,5alpha)- | 89-78-1 |
| alpha-Thioglycerol | 96-27-5 |
| Sodium dehydroacetate | 4418-26-2 |
| Ethyl 4-hydroxybenzoate | 120-47-8 |
| Ethyl Vanillin | 121-32-4 |
| Triacetin | 102-76-1 |
| Potassium sorbate | 590-00-1 |
| Triethyl citrate | 77-93-0 |
| (S)-(+)-Arginine | 74-79-3 |
| Glycine | 56-40-6 |
| (S)-(−)-Histidine | 71-00-1 |
| (S)-(+)-Lysine | 56-87-1 |
| Quinone | 106-51-4 |
| Naphthalene, 2-ethoxy- | 93-18-5 |
| Methanesulfonic Acid | 75-75-2 |
| DL-Tartaric Acid | 133-37-9 |
| Cyclamic acid | 100-88-9 |
| (S)-(−)-Phenylalanine | 63-91-2 |
| (S)-(−)-Tyrosine | 60-18-4 |
| Carvone | 99-49-0 |
| Ethyl butyrate | 105-54-4 |
| 6-Methyl-5-hepten-2-one | 110-93-0 |
| Ethyl acetoacetate | 141-97-9 |
| Methyl benzoate | 93-58-3 |
| Phenylacetic Acid | 103-82-2 |
| Adipic acid | 124-04-9 |
| Ethyl benzoate | 93-89-0 |
| Benzyl benzoate | 120-51-4 |
| Pyruvic acid | 127-17-3 |
| Succinic acid | 110-15-6 |
| Indole | 120-72-9 |
| Methyl anthranilate | 134-20-3 |
| Diethyl malonate | 105-53-3 |
| Niacin | 59-67-6 |
| Meso-inositol | 87-89-8 |
| 4-Aminobenzoic acid | 150-13-0 |
| Anisole | 100-66-3 |
| Urea | 57-13-6 |
| Pyrrolidine | 123-75-1 |
| Cyclopentanone | 120-92-3 |
| Acetic anhydride | 108-24-7 |
| Benzophenone | 119-61-9 |
| D-(−)-Fructose | 57-48-7 |
| D-(+)-Xylose | 58-86-6 |

| Name | CAS # |
|---|---|
| o-Methoxybenzoic Acid | 579-75-9 |
| linalool | 78-70-6 |
| ethyl isovalerate | 108-64-5 |
| 1,1'-Azobisformamide | 123-77-3 |
| 6-Methylcoumarin | 92-48-8 |
| acetoin | 513-86-0 |
| alpha-Phellandrene | 99-83-2 |
| Cymene | 99-87-6 |
| Dimethyl Succinate | 106-65-0 |
| p-Anisaldehyde | 123-11-5 |
| Phenyl ether | 101-84-8 |
| Tetrahydro-2-furanmethanol | 97-99-4 |
| Valeric Acid | 109-52-4 |
| 3,4-xylenol | 95-65-8 |
| 1,1-diethoxyethane | 105-57-7 |
| ethyl butyraldehyde | 97-96-1 |
| Ethyl crotonate | 623-70-1 |
| ethyl isobutyrate | 97-62-1 |
| methyl isovalerate | 556-24-1 |
| methyl propionate | 554-12-1 |
| methyl valeraldehyde | 123-15-9 |
| 4-(2,6,6-Trimethyl-2-cyclohexen-1-yl)-3-buten-2-one | 127-41-3 |
| 4-(2,6,6-trimethyl-1-cyclohexen-1-yl)-3-buten-2-one | 14901-07-6 |
| Maleic acid | 110-16-7 |
| 3-Methylbutanoic acid | 503-74-2 |
| L-Glutamic Acid | 56-86-0 |
| D-limonene | 5989-27-5 |
| 1-Phenyl-1-propanol | 93-54-9 |
| 2'-Hydroxyacetophenone | 118-93-4 |
| 2,4-Dihydroxybenzoic Acid | 89-86-1 |
| 2-Phenyl-1-propanol | 1123-85-9 |
| 3-Phenylpropionic Acid | 501-52-0 |
| 4-Ethoxyphenol | 622-62-8 |
| Alpha-Terpineol | 98-55-5 |
| Benzaldehyde Dimethylacetal | 1125-88-8 |
| Benzyl Ether | 103-50-4 |
| Benzyl Formate | 104-57-4 |
| Benzyl Salicylate | 118-58-1 |
| Cinnamyl Alcohol | 104-54-1 |
| D-(+)-Glucono-1,5-lactone | 4253-68-3 |
| D-Isoascorbic Acid | 89-65-6 |
| 2,3-Naphthalenediol | 92-44-4 |
| Diethyl Succinate | 123-25-1 |
| Ethyl 2-Aminobenzoate | 87-25-2 |
| Ethyl Cinnamate | 103-36-6 |
| Ethyl Phenylacetate | 101-97-3 |
| Ethyl Salicylate | 118-61-6 |
| gamma-Valerolactone | 108-29-2 |
| Hydroquinone Dimethyl Ether | 150-78-7 |
| Isocaproic Acid | 646-07-1 |
| Isoeugenol | 97-54-1 |
| Isopropyl Benzoate | 939-48-0 |
| L-(+)-Isoleucine | 73-32-5 |
| L-Malic acid | 97-67-6 |
| L-2-Aminopropionic Acid | 56-41-7 |
| L-Carnitine | 541-15-1 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| Phenoxyacetic Acid | 122-59-8 |
| Veratrole | 91-16-7 |
| 2-Ethylbutyric acid | 88-09-5 |
| 2-Methylpyrazine | 109-08-0 |
| o-methoxybenzaldehyde | 135-02-4 |
| L-Leucine | 61-90-5 |
| L-Asparagine | 70-47-3 |
| propiophenone | 93-55-0 |
| 5-isopropyl-2-methyl-phenol | 499-75-2 |
| Xylitol | 87-99-0 |
| ethyl 4-oxopentanoate | 539-88-8 |
| methyl cinnamate | 103-26-4 |
| cumic alcohol | 536-60-7 |
| methyl 2-naphthyl ketone | 93-08-3 |
| 1-methyl-4-(1-methylethyl)-1,4-Cyclohexadiene en - ethylene diamine | 99-85-4 |
| Caffeine | 58-08-2 |
| 5-methylfurfural | 620-02-0 |
| furfuryl acetate | 623-17-6 |
| terpinen-4-ol | 10482-56-1 |
| phenylethanal | 122-78-1 |
| 4'-Methoxyacetophenone | 100-06-1 |
| D-Fenchone | 4695-62-9 |
| 1-Methoxy-4-methylbenzene | 104-93-8 |
| o-methylanisole | 578-58-5 |
| Acetylacetaldehyde dimethyl acetal | 5436-21-5 |
| p-methylacetophenone | 122-00-9 |
| Methyl phenylacetate | 101-41-7 |
| 4-Ethoxybenzaldehyde | 10031-82-0 |
| p-tolyl acetate | 140-39-6 |
| 2,6-Dimethoxyphenol | 91-10-1 |
| Methyl 2-methoxybenzoate | 606-45-1 |
| alpha-methylcinnamaldehyde | 101-39-3 |
| 2-methoxycinnamaldehyde | 60125-24-8 |
| Potassium bicarbonate | 298-14-6 |
| piperonyl acetate | 326-61-4 |
| 2,3-hexanedione | 3848-24-6 |
| furfural acetone | 623-15-4 |
| trans beta-(2-furyl)acrolein | 623-30-3 |
| carveol | 99-48-9 |
| Methyl nicotinate | 93-60-7 |
| Ethyl benzoylacetate | 94-02-0 |
| Methyl 4-methoxybenzoate | 121-98-2 |
| Levulinic acid | 123-76-2 |
| m-Dimethoxybenzene | 151-10-0 |
| 2-acetylpyridine | 1122-62-9 |
| tetramethyl-pyrazine | 1124-11-4 |
| 2,3-dimethyl-pyrazine | 5910-89-4 |
| trimethyl-pyrazine | 14667-55-1 |
| 2-ethyl-3-methyl-pyrazine | 15707-23-0 |
| 5-Methyl-3H-furan-2-one | 591-12-8 |
| 2-Methoxy-4-methylphenol | 93-51-6 |
| piperazine | 110-85-0 |
| 2-Methoxy-4-propylphenol | 2785-87-7 |
| Naphthalene, 2-(2-methylpropoxy)- | 2173-57-1 |
| 2-Acetyl-1-methylpyrrole | 932-16-1 |
| 3,3-Dimethylacrylic acid | 541-47-9 |
| Ethyl sorbate | 2396-84-1 |
| 4-(4-Hydroxyphenyl)-2-butanone | 5471-51-2 |
| 4-Methoxyphenylacetone | 122-84-9 |
| (−)-Myrtenal | 564-94-3 |
| 3-Phenylpropionaldehyde | 104-53-0 |
| 1-Phenylethyl propionate | 120-45-6 |
| 2-Methyltetrahydrofuran-3-one | 3188-00-9 |
| Cinnamyl acetate | 103-54-8 |
| Styrallyl acetate | 93-92-5 |
| Ethyl 4-methoxybenzoate | 94-30-4 |
| Benzyl propionate | 122-63-4 |
| Phenylpyruvate | 156-06-9 |
| furaneol | 3658-77-3 |
| methyl 2-methylbutanoate | 868-57-5 |
| Benzeneacetaldehyde, alpha-methyl- | 93-53-8 |
| Dimethyl anthranilate | 85-91-6 |
| 1,1-Dimethoxy-2-phenylpropane | 90-87-9 |
| 4-hexanolide | 695-06-7 |
| Dimethylbenzylcarbinyl acetate | 151-05-3 |
| Benzyl isobutyrate | 103-28-6 |
| Acetyl isoeugenol | 93-29-8 |
| 2-Acetyl-5-methyl furan | 1193-79-9 |
| Alpha-methyl-p-isopropylphenylpropanaldehyde | 103-95-7 |
| Benzylcarbinyl formate | 104-62-1 |
| p-Cresyl alpha-toluate | 101-94-0 |
| Potassium bisulfate | 7646-93-7 |
| Potassium carbonate | 584-08-7 |
| Potassium chloride | 7447-40-7 |
| Potassium hydroxide | 1310-58-3 |
| Ethyl tiglate | 5837-78-5 |

| Name | CAS # |
|---|---|
| Nerol oxide | 1786-08-9 |
| DL-Tetrohydrofurfuryl propionate | 637-65-0 |
| Benzaldehyde propylene glycol acetal | 2568-25-4 |
| 2-Methyl-3-(2-furyl) acrolein | 874-66-8 |
| vanillin | 121-33-5 |
| Cholic acid | 81-25-4 |
| R-Carvone | 6485-40-1 |
| Potassium nitrate | 7757-79-1 |
| Potassium permanganate | 7722-64-7 |
| Potassium persulfate | 7727-21-1 |
| Potassium phosphate, dibasic | 2139900 |
| Potassium Phosphate Monobasic | 7778-77-0 |
| Potassium sulfate | 7778-80-5 |
| Sodium bicarbonate | 144-55-8 |
| Sodium bisulfite | 7631-90-5 |
| Sodium carbonate | 497-19-8 |
| Sodium chloride | 7647-14-5 |
| Sodium dithionite | 7775-14-6 |
| Sodium hydroxide | 1310-73-2 |
| Sodium nitrite | 7632-00-0 |
| Sodium Pyrophosphate | 7722-88-5 |
| Sodium sulfate | 7757-82-6 |
| Sodium sulfite | 7757-83-7 |
| Sodium thiocyanate | 540-72-7 |
| Calcium Carbonate | 471-34-1 |
| Calcium chloride | 10043-52-4 |
| Calcium gluconate | 299-28-5 |
| Calcium hydroxide | 1305-62-0 |
| Calcium phosphate, dibasic | 7757-93-9 |
| Calcium sulfate | 7778-18-9 |
| N-Methyl-D-glucamine | 6284-40-8 |
| Calcium oxide | 1305-78-8 |
| Calcium Phosphate Monobasic | 7758-23-8 |
| Magnesium chloride hexahydrate | 7791-18-6 |
| Magnesium sulfate | 7487-88-9 |
| Magnesium Sulfate Heptahydrate | 10034-99-8 |
| Aluminum chloride hexahydrate | 7784-13-6 |
| aluminum nitrate nonahydrate | 7784-27-2 |
| Aluminum potassium sulfate, dodecahydrate | 7784-24-9 |
| Aluminum sulfate, octadecahydrate | 7784-31-8 |
| (S)-(−)-Cysteine | 52-90-4 |
| p-Toluenesulfonic Acid | 104-15-4 |
| Potassium bitartrate | 868-14-4 |
| DL-aspartic acid | 617-45-8 |
| p-Dimethylaminobenzaldehyde | 100-10-7 |
| Sodium salicylate | 54-21-7 |
| Benzoin | 119-53-9 |
| Sodium dodecyl sulfate | 151-21-3 |
| L-Menthol | 2216-51-5 |
| Tiron | 149-45-1 |
| Riboflavin | 83-88-5 |
| Sodium Acetate Trihydrate | 6131-90-4 |
| Disodium Succinate Hexahydrate | 6106-21-4 |
| Disodium ethylenediaminetetraacetate dihydrate | 6381-92-6 |
| sodium citrate, dihydrate | 1545801 |
| Sodium potassium tartrate, tetrahydrate | 6381-59-5 |
| L-(+)-Arginine monohydrochloride | 1119-34-2 |
| Ethylenediamine dihydrochloride | 333-18-6 |
| Sodium formate | 141-53-7 |
| Sodium acetate | 127-09-3 |
| Potassium acetate | 127-08-2 |
| Ammonium citrate | 3012-65-5 |
| Ammonium bicarbonate | 1066-33-7 |
| Ammonium chloride | 12125-02-9 |
| Ammonium nitrate | 6484-52-2 |
| Ammonium persulfate | 7727-54-0 |
| Ammonium sulfate | 7783-20-2 |
| Zinc chloride | 7646-85-7 |
| Sulfuric acid, zinc salt (1:1), heptahydrate | 7446-20-0 |
| Sodium Tripolyphosphate | 7758-29-4 |
| ammonium benzoate | 1863-63-4 |
| ammonium bisulfite | 10192-30-0 |
| 1,5-Naphthalenedisulfonic Acid Disodium Salt | 1655-29-4 |
| 4-Hydroxybenzoic Acid | 99-96-7 |
| Diphenylacetic Acid | 117-34-0 |
| Glutaric Acid | 110-94-1 |
| L-(−)-Fucose | 2438-80-4 |
| L-Cysteine Hydrochloride | 52-89-1 |
| L-Histidine Hydrochloride Monohydrate | 1880304 |
| o-Toluic Acid | 118-90-1 |
| Pivalic Acid | 75-98-9 |
| Pyruvic Acid Sodium Salt | 113-24-6 |
| Potassium bromide | 2139626 |
| Sodium Dithionate Dihydrate | 7631-94-9 |
| Sodium Malonate | 141-95-7 |
| Trisodium Citrate | 68-04-2 |
| Potassium Sodium Tartrate | 304-59-6 |
| Potassium Citrate | 866-84-2 |
| D-Maltose Monohydrate | 6363-53-7 |
| Cyclohexaamylose | 10016-20-3 |
| Dodecyl sulfate, lithium salt | 2044-56-6 |
| Manganese chloride | 2145076 |
| methyl-urea | 598-50-5 |
| beta-Cyclodextrin | 7585-39-9 |
| Triphosphoric acid, pentapotassium salt | 13845-36-8 |
| Glycine ethyl ester hydrochloride | 623-33-6 |
| L-Histidine methyl ester dihydrochloride | 7389-87-9 |
| L-Leucine methyl ester hydrochloride | 7517-19-3 |
| D-Lysine hydrochloride | 7274-88-6 |
| 2-Naphthalenesulfonic acid sodium salt | 532-02-5 |
| calcium nitrate tetrahydrate | 13477-34-4 |
| Vitamin B1 | 59-43-8 |
| Zinc Acetate Dihydrate | 5970-45-6 |
| Potassium fluoride | 7789-23-3 |
| Potassium iodate | 2139718 |
| Potassium iodide | 7681-11-0 |
| Potassium thiocyanate | 333-20-0 |
| Sodium bromide | 7647-15-6 |
| Sodium fluoride | 7681-49-4 |
| Sodium iodide | 7681-82-5 |
| Sodium nitrate | 7631-99-4 |
| Calcium acetate | 5743-26-0 |
| Trichloroacetic acid | 76-03-9 |
| Ammonium acetate | 631-61-8 |
| Ammonium fluoride | 12125-01-8 |
| DL-malic acid | 617-48-1 |
| t-Butyl Alcohol | 75-65-0 |
| beta-Alanine | 107-95-9 |
| (S)-(−)-Tryptophan | 73-22-3 |
| Malonic acid | 141-82-2 |
| Phenethylamine | 64-04-0 |
| Salicylylaldehyde | 90-02-8 |
| Sodium benzoate | 532-32-1 |
| Mandelic acid | 90-64-2 |
| Calcium pantothenate | 137-08-6 |
| Chloroacetic Acid | 79-11-8 |
| Ethanol Amine | 141-43-5 |
| Salicylic acid | 69-72-7 |
| Saccharin sodium | 128-44-9 |
| Thiamine hydrochloride | 67-03-8 |
| 2,2'-Oxybisethanol | 111-46-6 |
| Resorcinol | 108-46-3 |
| 2-Amino-2-(hydroxymethyl)-1,3-propanediol | 77-86-1 |
| 2,5-Dimethylphenol | 95-87-4 |
| Ammonium Phosphate Monobasic | 7722-76-1 |
| 1,3-Butanediol | 107-88-0 |

-continued

| Name | CAS # |
|---|---|
| Glycolic Acid | 79-14-1 |
| Sodium Gluconate | 527-07-1 |
| Terephthalic Acid | 100-21-0 |
| L-Ascorbic Acid Sodium Salt | 134-03-2 |
| 3-Acetyl-6-methyl-2,4-pyrandione | 520-45-6 |
| Calcium Acetate | 62-54-4 |
| Nicotinamide | 98-92-0 |
| 1-Hydroxy-2-naphthoic Acid | 86-48-6 |
| 2-Isopropylphenol | 88-69-7 |
| 4-Aminosalicylic Acid | 65-49-6 |
| Calcium Glycerophosphate | 27214-00-2 |
| Erythorbic Acid Sodium Salt | 7378-23-6 |
| Gluconic Acid Potassium Salt | 299-27-4 |
| Orotic Acid | 65-86-1 |
| p-Anise Alcohol | 105-13-5 |
| Potassium Benzoate | 582-25-2 |
| Taurine | 107-35-7 |
| Thiamine Nitrate | 532-43-4 |
| 3,3,5-Trimethyl-1-cyclohexanol | 116-02-9 |
| tert-Butylhydroquinone | 1948-33-0 |
| Sulfosalicylic acid | 97-05-2 |
| Gallic acid | 149-91-7 |
| L-borneol | 464-45-9 |
| Isoborneol | 124-76-5 |
| 2,5-Dihydroxybenzoic acid, Gentisic acid | 490-79-9 |
| 5-hydroxy-6-methyl-3,4-pyridinedimethanol | 65-23-6 |
| Naphthalene-2-sulfonic acid | 120-18-3 |
| Ethanesulfonic acid, 2-hydroxy-, monosodium salt | 1562-00-1 |
| Pamoic acid | 130-85-8 |
| 2,4-Dimethylphenol | 105-67-9 |
| 3,5-Dihydroxyacetophenone | 51863-60-6 |
| Eugenol | 97-53-0 |
| n-Butyric Acid | 107-92-6 |
| Hydroquinone | 123-31-9 |
| Propionic Acid | 79-09-4 |
| meta-Phenylenediamine | 108-45-2 |
| Oxalic Acid | 144-62-7 |
| n-Hexanoic Acid | 142-62-1 |
| 2-Furancarboxylic Acid | 88-14-2 |
| 4'-Nitroacetanilide | 104-04-1 |
| D-(−)-Tartaric Acid | 147-71-7 |
| p-Acetamidobenzoic Acid | 556-08-1 |
| Galactaric acid | 526-99-8 |
| D-glucuronate | 1700908 |
| Lactobionic acid | 96-82-2 |
| p-Formylacetanilide | 122-85-0 |
| 2-Mercaptobenzoic acid | 147-93-3 |
| Propanoic acid, 2-hydroxy-, calcium salt (2:1), (S)- | 28305-25-1 |
| D(+)-10-Camphorsulfonic acid | 3144-16-9 |
| 3-Cyclopentylpropionic acid | 140-77-2 |
| 1R-(−)-Camphorsulfonic acid | 35963-20-3 |
| DL-Lysine | 70-54-2 |
| Cinnamic acid | 621-82-9 |
| Triethanolamine | 102-71-6 |
| Acetic Acid | 64-19-7 |
| Dichloroacetic Acid | 79-43-6 |
| Diethylamine | 109-89-7 |
| Diethylaminoethanol | 100-37-8 |
| N-(2-Hydroxyethyl)Morpholine | 622-40-2 |
| Octanoic Acid | 124-07-2 |
| isobutyric acid | 79-31-2 |
| Anisic Acid | 100-09-4 |
| Betaine | 107-43-7 |
| Enanthoic Acid | 111-14-8 |
| Hippuric Acid | 495-69-2 |
| Tiglic Acid | 80-59-1 |
| Cyclohexanecarboxylic acid | 98-89-5 |
| m-Methoxybenzoic acid | 586-38-9 |
| D-(+)-Camphoric acid | 124-83-4 |
| N-(2-Hydroxyethyl)pyrrolidine | 2955-88-6 |
| Sodium Metabisulfite | 7681-57-4 |
| sodium hydrogen phosphate | 7558-79-4 |
| Sodium Phosphate Monobasic | 7558-80-7 |
| Sodium thiosulfate | 7772-98-71 |
| Orthoboric acid | 10043-35-3 |
| Diethanolamine | 111-42-2 |
| Benzaldehyde | 100-52-7 |
| Sorbic acid | 110-44-1 |
| L-(+)-Tartaric Acid | 87-69-4 |
| D-mannitol | 69-65-8 |
| Butyl paraben | 94-26-8 |
| Thymol | 89-83-8 |
| Methyl salicylate | 119-36-8 |
| Citric acid | 77-92-9 |
| Creatinine | 60-27-5 |
| Vitamin C | 50-81-7 |
| Benzoic Acid | 65-85-0 |
| Methyl 4-hydroxybenzoate | 99-76-3 |
| m-Cresol | 108-39-4 |
| p-Cresol | 106-44-5 |
| Aspirin | 50-78-2 |
| Phenol | 108-95-2 |
| Sucrose | 57-50-1 |
| Potassium citrate, monohydrate | 1534146 |
| Sodium acetate | 127-09-3 |
| Lactic acid | 50-21-5 |
| Propionic acid, sodium salt | 65-85 |
| Benzyl alcohol | 100-51-6 |
| Phenethyl alcohol | 60-12-8 |
| Cholesterol | 57-88-5 |
| D-Glucose | 50-99-7 |
| Sorbitol | 50-70-4 |
| Aspartame | 22839-47-0 |
| Saccharin | 81-07-2 |
| 2,6-Di-tert-Butyl-p-Cresol | 128-37-0 |
| 4-Chloro-3-methylphenol | 59-50-7 |
| glycerin | 56-81-5 |
| Propyl paraben | 94-13-3 |
| fumaric acid | 110-17-8 |
| dabco | 280-57-9 |
| p-Phenylenediamine | 106-50-3 |
| Anethole | 4180-23-8 |
| propyl gallate | 121-79-9 |
| L-monosodium glutamate | 142-47-2 |
| Butylated hydroxyanisole | 25013-16-5 |
| Cyclohexanol, 5-methyl-2-(1-methylethyl)-, (1alpha,2beta,5alpha)- | 89-78-1 |
| alpha-Thioglycerol | 96-27-5 |
| Sodium dehydroacetate | 4418-26-2 |
| Ethyl 4-hydroxybenzoate | 120-47-8 |
| Ethyl Vanillin | 121-32-4 |
| Triacetin | 102-76-1 |
| Potassium sorbate | 590-00-1 |
| Triethyl citrate | 77-93-0 |
| (S)-(+)-Arginine | 74-79-3 |
| Glycine | 56-40-6 |
| (S)-(−)-Histidine | 71-00-1 |
| (S)-(+)-Lysine | 56-87-1 |
| Quinone | 106-51-4 |
| Naphthalene, 2-ethoxy- | 93-18-5 |
| Methanesulfonic Acid | 75-75-2 |
| DL-Tartaric Acid | 133-37-9 |
| Cyclamic acid | 100-88-9 |
| (S)-(−)-Phenylalanine | 63-91-2 |
| (S)-(−)-Tyrosine | 60-18-4 |
| Carvone | 99-49-0 |
| Ethyl butyrate | 105-54-4 |
| 6-Methyl-5-hepten-2-one | 110-93-0 |
| Ethyl acetoacetate | 141-97-9 |
| Methyl benzoate | 93-58-3 |
| Phenylacetic Acid | 103-82-2 |
| Adipic acid | 124-04-9 |
| Ethyl benzoate | 93-89-0 |
| Benzyl benzoate | 120-51-4 |
| Pyruvic acid | 127-17-3 |
| Succinic acid | 110-15-6 |
| Indole | 120-72-9 |
| Methyl anthranilate | 134-20-3 |
| Diethyl malonate | 105-53-3 |
| Niacin | 59-67-6 |

-continued

| Name | CAS # |
|---|---|
| Meso-inositol | 87-89-8 |
| 4-Aminobenzoic acid | 150-13-0 |
| Anisole | 100-66-3 |
| Urea | 57-13-6 |
| Pyrrolidine | 123-75-1 |
| Cyclopentanone | 120-92-3 |
| Acetic anhydride | 108-24-7 |
| Benzophenone | 119-61-9 |
| D-(−)-Fructose | 57-48-7 |
| D-(+)-Xylose | 58-86-6 |
| o-Methoxybenzoic Acid | 579-75-9 |
| linalool | 78-70-6 |
| ethyl isovalerate | 108-64-5 |
| 1,1'-Azobisformamide | 123-77-3 |
| 6-Methylcoumarin | 92-48-8 |
| acetoin | 513-86-0 |
| alpha-Phellandrene | 99-83-2 |
| Cymene | 99-87-6 |
| Dimethyl Succinate | 106-65-0 |
| p-Anisaldehyde | 123-11-5 |
| Phenyl ether | 101-84-8 |
| Tetrahydro-2-furanmethanol | 97-99-4 |
| Valeric Acid | 109-52-4 |
| 3,4-xylenol | 95-65-8 |
| 1,1-diethoxyethane | 105-57-7 |
| ethyl butyraldehyde | 97-96-1 |
| Ethyl crotonate | 623-70-1 |
| ethyl isobutyrate | 97-62-1 |
| methyl isovalerate | 556-24-1 |
| methyl propionate | 554-12-1 |
| methyl valeraldehyde | 123-15-9 |
| 4-(2,6,6-Trimethyl-2-cyclohexen-1-yl)-3-buten-2-one | 127-41-3 |
| 4-(2,6,6-trimethyl-1-cyclohexen-1-yl)-3-buten-2-one | 14901-07-6 |
| Maleic acid | 110-16-7 |
| 3-Methylbutanoic acid | 503-74-2 |
| L-Glutamic Acid | 56-86-0 |
| D-limonene | 5989-27-5 |
| 1-Phenyl-1-propanol | 93-54-9 |
| 2'-Hydroxyacetophenone | 118-93-4 |
| 2,4-Dihydroxybenzoic Acid | 89-86-1 |
| 2-Phenyl-1-propanol | 1123-85-9 |
| 3-Phenylpropionic Acid | 501-52-0 |
| 4-Ethoxyphenol | 622-62-8 |
| Alpha-Terpineol | 98-55-5 |
| Benzaldehyde Dimethylacetal | 1125-88-8 |
| Benzyl Ether | 103-50-4 |
| Benzyl Formate | 104-57-4 |
| Benzyl Salicylate | 118-58-1 |
| Cinnamyl Alcohol | 104-54-1 |
| D-(+)-Glucono-1,5-lactone | 4253-68-3 |
| D-Isoascorbic Acid | 89-65-6 |
| 2,3-Naphthalenediol | 92-44-4 |
| Diethyl Succinate | 123-25-1 |
| Ethyl 2-Aminobenzoate | 87-25-2 |
| Ethyl Cinnamate | 103-36-6 |
| Ethyl Phenylacetate | 101-97-3 |
| Ethyl Salicylate | 118-61-6 |
| gamma-Valerolactone | 108-29-2 |
| Hydroquinone Dimethyl Ether | 150-78-7 |
| Isocaproic Acid | 646-07-1 |
| Isoeugenol | 97-54-1 |
| Isopropyl Benzoate | 939-48-0 |
| L-(+)-Isoleucine | 73-32-5 |
| L-Malic acid | 97-67-6 |
| L-2-Aminopropionic Acid | 56-41-7 |
| L-Carnitine | 541-15-1 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| Phenoxyacetic Acid | 122-59-8 |
| Veratrole | 91-16-7 |
| 2-Ethylbutyric acid | 88-09-5 |
| 2-Methylpyrazine | 109-08-0 |

-continued

| Name | CAS # |
|---|---|
| o-methoxybenzaldehyde | 135-02-4 |
| L-Leucine | 61-90-5 |
| L-Asparagine | 70-47-3 |
| propiophenone | 93-55-0 |
| 5-isopropyl-2-methyl-phenol | 499-75-2 |
| Xylitol | 87-99-0 |
| ethyl 4-oxopentanoate | 539-88-8 |
| methyl cinnamate | 103-26-4 |
| cumic alcohol | 536-60-7 |
| methyl 2-naphthyl ketone | 93-08-3 |
| 1-methyl-4-(1-methylethyl)-1,4-Cyclohexadiene en-ethylene diamine | 99-85-4 |
| Caffeine | 58-08-2 |
| 5-methylfurfural | 620-02-0 |
| furfuryl acetate | 623-17-6 |
| terpinen-4-ol | 10482-56-1 |
| phenylethanal | 122-78-1 |
| 4'-Methoxyacetophenone | 100-06-1 |
| D-Fenchone | 4695-62-9 |
| 1-Methoxy-4-methylbenzene | 104-93-8 |
| o-methylanisole | 578-58-5 |
| Acetylacetaldehyde dimethyl acetal | 5436-21-5 |
| p-methylacetophenone | 122-00-9 |
| Methyl phenylacetate | 101-41-7 |
| 4-Ethoxybenzaldehyde | 10031-82-0 |
| p-tolyl acetate | 140-39-6 |
| 2,6-Dimethoxyphenol | 91-10-1 |
| Methyl 2-methoxybenzoate | 606-45-1 |
| alpha-methylcinnamaldehyde | 101-39-3 |
| 2-methoxycinnamaldehyde | 60125-24-8 |
| Potassium bicarbonate | 298-14-6 |
| piperonyl acetate | 326-61-4 |
| 2,3-hexanedione | 3848-24-6 |
| furfural acetone | 623-15-4 |
| trans beta-(2-furyl)acrolein | 623-30-3 |
| carveol | 99-48-9 |
| Methyl nicotinate | 93-60-7 |
| Ethyl benzoylacetate | 94-02-0 |
| Methyl 4-methoxybenzoate | 121-98-2 |
| Levulinic acid | 123-76-2 |
| m-Dimethoxybenzene | 151-10-0 |
| 2-acetylpyridine | 1122-62-9 |
| tetramethyl-pyrazine | 1124-11-4 |
| 2,3-dimethyl-pyrazine | 5910-89-4 |
| trimethyl-pyrazine | 14667-55-1 |
| 2-ethyl-3-methyl-pyrazine | 15707-23-0 |
| 5-Methyl-3H-furan-2-one | 591-12-8 |
| 2-Methoxy-4-methylphenol | 93-51-6 |
| piperazine | 110-85-0 |
| 2-Methoxy-4-propylphenol | 2785-87-7 |
| Naphthalene, 2-(2-methylpropoxy)- | 2173-57-1 |
| 2-Acetyl-1-methylpyrrole | 932-16-1 |
| 3,3-Dimethylacrylic acid | 541-47-9 |
| Ethyl sorbate | 2396-84-1 |
| 4-(4-Hydroxyphenyl)-2-butanone | 5471-51-2 |
| 4-Methoxyphenylacetone | 122-84-9 |
| (−)-Myrtenal | 564-94-3 |
| 3-Phenylpropionaldehyde | 104-53-0 |
| 1-Phenylethyl propionate | 120-45-6 |
| 2-Methyltetrahydrofuran-3-one | 3188-00-9 |
| Cinnamyl acetate | 103-54-8 |
| Styrallyl acetate | 93-92-5 |
| Ethyl 4-methoxybenzoate | 94-30-4 |
| Benzyl propionate | 122-63-4 |
| Phenylpyruvate | 156-06-9 |
| furaneol | 3658-77-3 |
| methyl 2-methylbutanoate | 868-57-5 |
| Benzeneacetaldehyde, alpha-methyl- | 93-53-8 |
| Dimethyl anthranilate | 85-91-6 |
| 1,1-Dimethoxy-2-phenylpropane | 90-87-9 |
| 4-hexanolide | 695-06-7 |
| Dimethylbenzylcarbinyl acetate | 151-05-3 |
| Benzyl isobutyrate | 103-28-6 |
| Acetyl isoeugenol | 93-29-8 |

| Name | CAS # |
|---|---|
| 2-Acetyl-5-methyl furan | 1193-79-9 |
| Alpha-methyl-p-isopropylphenylpropanaldehyde | 103-95-7 |
| Benzylcarbinyl formate | 104-62-1 |
| p-Cresyl alpha-toluate | 101-94-0 |
| Potassium bisulfate | 7646-93-7 |
| Potassium carbonate | 584-08-7 |
| Potassium chloride | 7447-40-7 |
| Potassium hydroxide | 1310-58-3 |
| Ethyl tiglate | 5837-78-5 |
| Nerol oxide | 1786-08-9 |
| DL-Tetrahydrofurfuryl propionate | 637-65-0 |
| Benzaldehyde propylene glycol acetal | 2568-25-4 |
| 2-Methyl-3-(2-furyl) acrolein | 874-66-8 |
| vanillin | 121-33-5 |
| Cholic acid | 81-25-4 |
| R-Carvone | 6485-40-1 |
| Potassium nitrate | 7757-79-1 |
| Potassium permanganate | 7722-64-7 |
| Potassium persulfate | 7727-21-1 |
| Potassium phosphate, dibasic | 2139900 |
| Potassium Phosphate Monobasic | 7778-77-0 |
| Potassium sulfate | 7778-80-5 |
| Sodium bicarbonate | 144-55-8 |
| Sodium bisulfite | 7631-90-5 |
| Sodium carbonate | 497-19-8 |
| Sodium chloride | 7647-14-5 |
| Sodium dithionite | 7775-14-6 |
| Sodium hydroxide | 1310-73-2 |
| Sodium nitrite | 7632-00-0 |
| Sodium Pyrophosphate | 7722-88-5 |
| Sodium sulfate | 7757-82-6 |
| Sodium sulfite | 7757-83-7 |
| Sodium thiocyanate | 540-72-7 |
| Calcium Carbonate | 471-34-1 |
| Calcium chloride | 10043-52-4 |
| Calcium gluconate | 299-28-5 |
| Calcium hydroxide | 1305-62-0 |
| Calcium phosphate, dibasic | 7757-93-9 |
| Calcium sulfate | 7778-18-9 |
| N-Methyl-D-glucamine | 6284-40-8 |
| Calcium oxide | 1305-78-8 |
| Calcium Phosphate Monobasic | 7758-23-8 |
| Magnesium chloride hexahydrate | 7791-18-6 |
| Magnesium sulfate | 7487-88-9 |
| Magnesium Sulfate Heptahydrate | 10034-99-8 |
| Aluminum chloride hexahydrate | 7784-13-6 |
| aluminum nitrate nonahydrate | 7784-27-2 |
| Aluminum potassium sulfate, dodecahydrate | 7784-24-9 |
| Aluminum sulfate, octadecahydrate | 7784-31-8 |
| (S)-(−)-Cysteine | 52-90-4 |
| p-Toluenesulfonic Acid | 104-15-4 |
| Potassium bitartrate | 868-14-4 |
| DL-aspartic acid | 617-45-8 |
| p-Dimethylaminobenzaldehyde | 100-10-7 |
| Sodium salicylate | 54-21-7 |
| Benzoin | 119-53-9 |
| Sodium dodecyl sulfate | 151-21-3 |
| L-Menthol | 2216-51-5 |
| Tiron | 149-45-1 |
| Riboflavin | 83-88-5 |
| Sodium Acetate Trihydrate | 6131-90-4 |
| Disodium Succinate Hexahydrate | 6106-21-4 |
| Disodium ethylenediaminetetraacetate dihydrate | 6381-92-6 |
| sodium citrate, dihydrate | 1545801 |
| Sodium potassium tartrate, tetrahydrate | 6381-59-5 |
| L-(+)-Arginine monohydrochloride | 1119-34-2 |
| Ethylenediamine dihydrochloride | 333-18-6 |
| Sodium formate | 141-53-7 |
| Sodium acetate | 127-09-3 |
| Potassium acetate | 127-08-2 |
| Ammonium citrate | 3012-65-5 |
| Ammonium bicarbonate | 1066-33-7 |
| Ammonium chloride | 12125-02-9 |
| Ammonium nitrate | 6484-52-2 |
| Ammonium persulfate | 7727-54-0 |
| Ammonium sulfate | 7783-20-2 |
| Zinc chloride | 7646-85-7 |
| Sulfuric acid, zinc salt (1:1), heptahydrate | 7446-20-0 |
| Sodium Tripolyphosphate | 7758-29-4 |
| ammonium benzoate | 1863-63-4 |
| ammonium bisulfite | 10192-30-0 |
| 1,5-Naphthalenedisulfonic Acid Disodium Salt | 1655-29-4 |
| 4-Hydroxybenzoic Acid | 99-96-7 |
| Diphenylacetic Acid | 117-34-0 |
| Glutaric Acid | 110-94-1 |
| L-(−)-Fucose | 2438-80-4 |
| L-Cysteine Hydrochloride | 52-89-1 |
| L-Histidine Hydrochloride Monohydrate | 1880304 |
| o-Toluic Acid | 118-90-1 |
| Pivalic Acid | 75-98-9 |
| Pyruvic Acid Sodium Salt | 113-24-6 |
| Potassium bromide | 2139626 |
| Sodium Dithionate Dihydrate | 7631-94-9 |
| Sodium Malonate | 141-95-7 |
| Trisodium Citrate | 68-04-2 |
| Potassium Sodium Tartrate | 304-59-6 |
| Potassium Citrate | 866-84-2 |
| D-Maltose Monohydrate | 6363-53-7 |
| Cyclohexaamylose | 10016-20-3 |
| Dodecyl sulfate, lithium salt | 2044-56-6 |
| Manganese chloride | 2145076 |
| methyl-urea | 598-50-5 |
| beta-Cyclodextrin | 7585-39-9 |
| Triphosphoric acid, pentapotassium salt | 13845-36-8 |
| Glycine ethyl ester hydrochloride | 623-33-6 |
| L-Histidine methyl ester dihydrochloride | 7389-87-9 |
| L-Leucine methyl ester hydrochloride | 7517-19-3 |
| D-Lysine hydrochloride | 7274-88-6 |
| 2-Naphthalenesulfonic acid sodium salt | 532-02-5 |
| calcium nitrate tetrahydrate | 13477-34-4 |
| Vitamin B1 | 59-43-8 |
| Zinc Acetate Dihydrate | 5970-45-6 |
| Potassium fluoride | 7789-23-3 |
| Potassium iodate | 2139718 |
| Potassium iodide | 7681-11-0 |
| Potassium thiocyanate | 333-20-0 |
| Sodium bromide | 7647-15-6 |
| Sodium fluoride | 7681-49-4 |
| Sodium iodide | 7681-82-5 |
| Sodium nitrate | 7631-99-4 |
| Calcium acetate | 5743-26-0 |
| Trichloroacetic acid | 76-03-9 |
| Ammonium acetate | 631-61-8 |
| Ammonium fluoride | 12125-01-8 |
| DL-malic acid | 617-48-1 |
| t-Butyl Alcohol | 75-65-0 |
| beta-Alanine | 107-95-9 |
| (S)-(−)-Tryptophan | 73-22-3 |
| Malonic acid | 141-82-2 |
| Phenethylamine | 64-04-0 |
| Salicylylaldehyde | 90-02-8 |
| Sodium benzoate | 532-32-1 |
| Mandelic acid | 90-64-2 |
| Calcium pantothenate | 137-08-6 |
| Chloroacetic Acid | 79-11-8 |
| Ethanol Amine | 141-43-5 |
| Salicylic acid | 69-72-7 |
| Saccharin sodium | 128-44-9 |

| Name | CAS # |
| --- | --- |
| Thiamine hydrochloride | 67-03-8 |
| 2,2'-Oxybisethanol | 111-46-6 |
| Resorcinol | 108-46-3 |
| 2-Amino-2-(hydroxymethyl)-1,3-propanediol | 77-86-1 |
| 2,5-Dimethylphenol | 95-87-4 |
| Ammonium Phosphate Monobasic | 7722-76-1 |
| 1,3-Butanediol | 107-88-0 |
| Glycolic Acid | 79-14-1 |
| Sodium Gluconate | 527-07-1 |
| Terephthalic Acid | 100-21-0 |
| L-Ascorbic Acid Sodium Salt | 134-03-2 |
| 3-Acetyl-6-methyl-2,4-pyrandione | 520-45-6 |
| Calcium Acetate | 62-54-4 |
| Nicotinamide | 98-92-0 |
| 1-Hydroxy-2-naphthoic Acid | 86-48-6 |
| 2-Isopropylphenol | 88-69-7 |
| 4-Aminosalicylic Acid | 65-49-6 |
| Calcium Glycerophosphate | 27214-00-2 |
| Erythorbic Acid Sodium Salt | 7378-23-6 |
| Gluconic Acid Potassium Salt | 299-27-4 |
| Orotic Acid | 65-86-1 |
| p-Anise Alcohol | 105-13-5 |
| Potassium Benzoate | 582-25-2 |
| Taurine | 107-35-7 |
| Thiamine Nitrate | 532-43-4 |
| 3,3,5-Trimethyl-1-cyclohexanol | 116-02-9 |
| tert-Butylhydroquinone | 1948-33-0 |
| Sulfosalicylic acid | 97-05-2 |
| Gallic acid | 149-91-7 |
| L-borneol | 464-45-9 |
| Isoborneol | 124-76-5 |
| 2,5-Dihydroxybenzoic acid, Gentisic acid | 490-79-9 |
| 5-hydroxy-6-methyl-3,4-pyridinedimethanol | 65-23-6 |
| Naphthalene-2-sulfonic acid | 120-18-3 |
| Ethanesulfonic acid, 2-hydroxy-, monosodium salt | 1562-00-1 |
| Pamoic acid | 130-85-8 |
| 2,4-Dimethylphenol | 105-67-9 |
| 3,5-Dihydroxyacetophenone | 51863-60-6 |
| Eugenol | 97-53-0 |
| n-Butyric Acid | 107-92-6 |
| Hydroquinone | 123-31-9 |
| Propionic Acid | 79-09-4 |
| meta-Phenylenediamine | 108-45-2 |
| Oxalic Acid | 144-62-7 |
| n-Hexanoic Acid | 142-62-1 |
| 2-Furancarboxylic Acid | 88-14-2 |
| 4'-Nitroacetanilide | 104-04-1 |
| D-(−)-Tartaric Acid | 147-71-7 |
| p-Acetamidobenzoic Acid | 556-08-1 |
| Galactaric acid | 526-99-8 |
| D-glucuronate | 1700908 |
| Lactobionic acid | 96-82-2 |
| p-Formylacetanilide | 122-85-0 |
| 2-Mercaptobenzoic acid | 147-93-3 |
| Propanoic acid, 2-hydroxy-, calcium salt (2:1), (S)- | 28305-25-1 |
| D(+)-10-Camphorsulfonic acid | 3144-16-9 |
| 3-Cyclopentylpropionic acid | 140-77-2 |
| 1R-(−)-Camphorsulfonic acid | 35963-20-3 |
| DL-Lysine | 70-54-2 |
| Cinnamic acid | 621-82-9 |
| Triethanolamine | 102-71-6 |
| Acetic Acid | 64-19-7 |
| Dichloroacetic Acid | 79-43-6 |
| Diethylamine | 109-89-7 |
| Diethylaminoethanol | 100-37-8 |
| N-(2-Hydroxyethyl)Morpholine | 622-40-2 |
| Octanoic Acid | 124-07-2 |
| isobutyric acid | 79-31-2 |
| Anisic Acid | 100-09-4 |
| Betaine | 107-43-7 |
| Enanthoic Acid | 111-14-8 |
| Hippuric Acid | 495-69-2 |
| Tiglic Acid | 80-59-1 |
| Cyclohexanecarboxylic acid | 98-89-5 |
| m-Methoxybenzoic acid | 586-38-9 |
| D-(+)-Camphoric acid | 124-83-4 |
| N-(2-Hydroxyethyl)pyrrolidine | 2955-88-6 |

TABLE 4

Crystal data and structure refinement for Fluoxetine HCl:Benzoic acid (1:1).

| | |
| --- | --- |
| Identification code | Fluoxetine HCl:Benzoic acid (1:1) |
| Empirical formula | C24 H25 Cl F3 NO3 |
| Formula weight | 467.90 |
| Temperature | 100(2) K |
| Wavelength | 0.71073 Å |
| Crystal system | Monoclinic |
| Space group | P2(1)/n |
| Unit cell dimensions | a = 14.806(5) Å  α = 90°. |
| | b = 13.179(4) Å  β = 97.738(13)°. |
| | c = 24.417(7) Å  γ = 90°. |
| Volume | 4721(2) Å$^3$ |
| Z | 8 |
| Density (calculated) | 1.317 Mg/m$^3$ |
| Absorption coefficient | 0.210 mm$^{-1}$ |
| F(000) | 1952 |
| Crystal size | 0.47 × 0.15 × 0.10 mm$^3$ |
| Theta range for data collection | 1.52 to 33.07° |
| Index ranges | −22 <= h <= 22, −20 <= k <= 20, −37 <= l <= 37 |
| Reflections collected | 82494 |
| Independent reflections | 17030 [R(int) = 0.0751] |
| Completeness to theta = 33.07° | 95.0% |
| Absorption correction | None |
| Refinement method | Full-matrix least-squares on F$^2$ |
| Data/restraints/parameters | 17030/0/581 |
| Goodness-of-fit on F$^2$ | 1.053 |
| Final R indices [I > 2sigma(I)] | R1 = 0.0853, wR2 = 0.1933 |
| R indices (all data) | R1 = 0.1330, wR2 = 0.2168 |
| Largest diff. peak and hole | 2.571 and −0.689 e · Å$^{-3}$ |

TABLE 5

Crystal data and structure refinement for Fluoxetine HCl-succinic acid (2:1).

| | |
| --- | --- |
| Identification code | Fluoxetine HCl-succinic acid (2:1) |
| Empirical formula | C38 H42 Cl2 F6 N2 O6 |
| Formula weight | 807.64 |
| Temperature | 100(2) K |
| Wavelength | 0.71073 Å |
| Crystal system | Orthorhombic |
| Space group | Pbcn |
| Unit cell dimensions | a = 26.620(2) Å  α = 90°. |
| | b = 7.2147(7) Å  β = 90°. |
| | c = 20.8315(19) Å  γ = 90°. |
| Volume | 4000.8(6) Å$^3$ |
| Z | 4 |
| Density (calculated) | 1.341 Mg/m$^3$ |
| Absorption coefficient | 0.236 mm$^{-1}$ |
| F(000) | 1680 |
| Crystal size | 0.21 × 0.18 × 0.09 mm$^3$ |
| Theta range for data collection | 1.53 to 27.50°. |
| Index ranges | −34 <= h <= 34, −9 <= k <= 9, −26 <= l <= 27 |
| Reflections collected | 37123 |
| Independent reflections | 4600 [R(int) = 0.0748] |
| Completeness to theta = 27.50° | 100.0% |
| Absorption correction | Semi-empirical from equivalents |
| Max. and min. transmission | 1.000 and 0.813837 |
| Refinement method | Full-matrix least-squares on F$^2$ |
| Data/restraints/parameters | 4600/0/249 |
| Goodness-of-fit on F$^2$ | 1.156 |

TABLE 5-continued

Crystal data and structure refinement for Fluoxetine HCl-succinic acid (2:1).

| | |
|---|---|
| Final R indices [I > 2sigma(I)] | R1 = 0.0786, wR2 = 0.1782 |
| R indices (all data) | R1 = 0.0911, wR2 = 0.1852 |
| Largest diff. peak and hole | 0.682 and −0.499 e · Å$^{-3}$ |

TABLE 6

Crystal data and structure refinement for Nabumetone:2,3-naphthalenediol (1:1).

| | |
|---|---|
| Identification code | Nabumetone:2,3-naphthalenediol (1:1) |
| Empirical formula | C25 H24 O4 |
| Formula weight | 388.44 |
| Temperature | 100(2) K |
| Wavelength | 1.54178 Å |
| Crystal system | Monoclinic |
| Space group | P2(1)/n |
| Unit cell dimensions | a = 17.1585(7) Å   α = 90°. |
| | b = 5.5168(3) Å    β = 91.319(3)°. |
| | c = 20.7083(9) Å   γ = 90°. |
| Volume | 1959.73(16) Å$^3$ |
| Z | 4 |
| Density (calculated) | 1.317 Mg/m$^3$ |
| Absorption coefficient | 0.710 mm$^{-1}$ |
| F(000) | 824 |
| Crystal size | 0.21 × 0.08 × 0.025 mm$^3$ |
| Theta range for data collection | 3.31 to 66.15°. |
| Index ranges | −17 <= h <= 19, −6 <= k <= 5, −24 <= l <= 23 |
| Reflections collected | 8803 |
| Independent reflections | 3063 [R(int) = 0.0801] |
| Completeness to theta = 66.15° | 89.1% |
| Absorption correction | None |
| Refinement method | Full-matrix least-squares on F$^2$ |
| Data/restraints/parameters | 3063/2/266 |
| Goodness-of-fit on F$^2$ | 1.019 |
| Final R indices [I > 2sigma(I)] | R1 = 0.0528, wR2 = 0.1332 |
| R indices (all data) | R1 = 0.1116, wR2 = 0.1692 |
| Largest diff. peak and hole | 0.277 and −0.325 e · Å$^{-3}$ |

TABLE 7

Crystal data and structure refinement for Fluoxetine HCl-fumaric acid (2:1).

| | |
|---|---|
| Identification code | a6g41m |
| Empirical formula | C38 H42 Cl2 F6 N2 O6 |
| Formula weight | 807.64 |
| Temperature | 173(2) K |
| Wavelength | 1.54178 Å |
| Crystal system | Orthorhombic |
| Space group | Pbcn |
| Unit cell dimensions | a = 26.6914(8) Å   α = 90°. |
| | b = 7.1807(3) Å    β = 90°. |
| | c = 20.6546(7) Å   γ = 90°. |
| Volume | 3958.7(2) Å$^3$ |
| Z | 4 |
| Density (calculated) | 1.355 Mg/m$^3$ |
| Absorption coefficient | 2.130 mm$^{-1}$ |
| F(000) | 1680 |
| Crystal size | 0.20 × 0.14 × 0.08 mm$^3$ |
| Theta range for data collection | 3.31 to 58.93° |
| Index ranges | −24 <= h <= 29, −7 <= k <= 7, −21 <= l <= 22 |
| Reflections collected | 15698 |
| Independent reflections | 2823 [R(int) = 0.1693] |
| Completeness to theta = 58.93° | 99.7% |
| Absorption correction | None |
| Refinement method | Full-matrix least-squares on F$^2$ |
| Data/restraints/parameters | 2823/0/246 |
| Goodness-of-fit on F$^2$ | 1.018 |
| Final R indices [I > 2sigma(I)] | R1 = 0.0469, wR2 = 0.0927 |
| R indices (all data) | R1 = 0.0940, wR2 = 0.1197 |
| Largest diff. peak and hole | 0.583 and −0.750 e · Å$^{-3}$ |

What is claimed is:

1. A cocrystal of fluoxetine hydrochloride and a guest, wherein the guest is selected from benzoic acid, succinic acid, and fumaric acid.

2. The cocrystal of claim 1 wherein the guest is benzoic acid.

3. The cocrystal of claim 2 wherein the cocrystal is a 1:1 cocrystal of fluoxetine hydrochloride to benzoic acid.

4. The cocrystal of claim 3 having a melting point of about 134° C.

5. The cocrystal of claim 1 wherein the guest is succinic acid.

6. The cocrystal of claim 5 wherein the cocrystal is a 2:1 cocrystal of fluoxetine hydrochloride to succinic add.

7. The cocrystal of claim 6 having a melting point of about 137° C.

8. The cocrystal of claim 1 wherein the guest is fumaric acid.

9. The cocrystal of claim 8 wherein the cocrystal is a 2:1 cocrystal of fluoxetine hydrochloride to fumaric acid.

10. The cocrystal of claim 6 having a melting point of about 164° C.

11. The cocrystal of claim 6 wherein the crystal system is orthorhombic.

12. The cocrystal of claim 11 wherein the space group is Pbcn.

13. The cocrystal of claim 11 wherein the unit cell volume is about 4000 Å$^3$ at about 100 K.

14. The cocrystal of claim 12 wherein the unit cell volume is about 4000 Å$^3$ at about 100 K.

15. The cocrystal of claim 11 wherein the unit cell dimensions are: a is about 26.6 Å at about 100 K; b is about 7.2 Å at about 100 K; and c is about 20.8 Å at about 100 K.

* * * * *